US009685039B2

(12) United States Patent
Evans

(10) Patent No.: US 9,685,039 B2
(45) Date of Patent: Jun. 20, 2017

(54) GAMING SYSTEM AND METHOD WHICH PROVIDES PLAYERS AN OPPORTUNITY TO WIN A PROGRESSIVE AWARD

(71) Applicant: IGT, Las Vegas, NV (US)

(72) Inventor: Christina M. Evans, High Point, NC (US)

(73) Assignee: IGT, Las Vegas, NV (US)

( * ) Notice: Subject to any disclaimer, the term of this patent is extended or adjusted under 35 U.S.C. 154(b) by 4 days.

(21) Appl. No.: 15/058,975

(22) Filed: Mar. 2, 2016

(65) Prior Publication Data

US 2016/0180648 A1 Jun. 23, 2016

Related U.S. Application Data

(63) Continuation of application No. 11/557,869, filed on Nov. 8, 2006, now abandoned.

(51) Int. Cl.
*A61F 13/00* (2006.01)
*G07F 17/32* (2006.01)

(52) U.S. Cl.
CPC ...... *G07F 17/3258* (2013.01); *G07F 17/3246* (2013.01)

(58) Field of Classification Search
CPC .. G07F 17/32; G07F 17/3244; G07F 17/3267; G07F 17/3258
(Continued)

(56) References Cited

U.S. PATENT DOCUMENTS 1,978,395 A 10/1934 Groetchen
2,545,644 A 3/1951 Benton et al.
(Continued)

FOREIGN PATENT DOCUMENTS

AU 524709 9/1982
AU 555905 10/1986
(Continued)

OTHER PUBLICATIONS

4DU Dice Unit Advertisement written by starpoint.uk.com, printed on Sep. 3, 2002.
(Continued)

*Primary Examiner* — Allen Chan
(74) *Attorney, Agent, or Firm* — Neal, Gerber & Eisenberg LLP

(57) ABSTRACT

A gaming system is provided that includes a central server linked to a plurality of gaming machines. The gaming system includes a progressive award adapted to be provided to a designated winning player of the gaming machines in the gaming system. In one embodiment, the gaming system designates the winning player when the progressive award reaches a player threshold value. In such an embodiment, the gaming system provides the progressive award to the designated winning player when the progressive award reaches an award threshold value. In one embodiment, each player who contributes to the progressive award is eligible to win that progressive award, even if that player is not playing one of the gaming machines in the gaming system. The gaming system provides the progressive award to the designated winning player or causes a notification of being provided the progressive award to the winning player. Accordingly, the gaming system stores the progressive award until one of the players of one of the gaming machines is designated.

10 Claims, 11 Drawing Sheets

(58) Field of Classification Search
USPC .................................................... 463/25–27
See application file for complete search history.

(56) References Cited

U.S. PATENT DOCUMENTS

| | | | |
|---|---|---|---|
| 2,743,108 | A | 4/1956 | Sanders |
| 2,942,574 | A | 6/1960 | Golay |
| 3,420,525 | A | 1/1969 | Waders |
| 3,618,019 | A | 11/1971 | Nemirovsky |
| 3,642,287 | A | 2/1972 | Lally et al. |
| 3,735,987 | A | 5/1973 | Ohki |
| 3,904,207 | A | 9/1975 | Gold |
| 3,971,557 | A | 7/1976 | Breslow et al. |
| 3,975,022 | A | 8/1976 | Figueroa |
| 3,998,309 | A | 12/1976 | Mandas et al. |
| 4,072,930 | A | 2/1978 | Lucero et al. |
| 4,182,515 | A | 1/1980 | Nemeth |
| 4,198,052 | A | 4/1980 | Gauselmann |
| 4,238,127 | A | 12/1980 | Lucero et al. |
| 4,277,064 | A | 7/1981 | Newman |
| 4,283,709 | A | 8/1981 | Lucero et al. |
| 4,335,809 | A | 6/1982 | Wain |
| 4,363,485 | A | 12/1982 | Edwall |
| 4,409,656 | A | 10/1983 | Andersen et al. |
| 4,410,178 | A | 10/1983 | Partridge |
| 4,448,419 | A | 5/1984 | Telnaes |
| 4,494,197 | A | 1/1985 | Troy et al. |
| 4,560,161 | A | 12/1985 | Hamano |
| 4,573,681 | A | 3/1986 | Okada |
| 4,582,324 | A | 4/1986 | Koza et al. |
| 4,618,150 | A | 10/1986 | Kimura |
| 4,621,814 | A | 11/1986 | Stepan et al. |
| 4,624,459 | A | 11/1986 | Kaufman |
| 4,636,951 | A | 1/1987 | Harlick |
| 4,652,998 | A | 3/1987 | Koza et al. |
| 4,669,731 | A | 6/1987 | Clarke |
| 4,695,053 | A | 9/1987 | Vazquez, Jr. et al. |
| 4,721,307 | A | 1/1988 | Okada |
| 4,732,386 | A | 3/1988 | Rayfiel |
| 4,743,024 | A | 5/1988 | Helm et al. |
| 4,756,531 | A | 7/1988 | DiRe et al. |
| 4,760,527 | A | 7/1988 | Sidley |
| 4,775,155 | A | 10/1988 | Lees |
| 4,805,907 | A | 2/1989 | Hagiwara |
| 4,836,546 | A | 6/1989 | DiRe et al. |
| 4,837,728 | A | 6/1989 | Barrie et al. |
| 4,838,552 | A | 6/1989 | Hagiwara |
| 4,842,278 | A | 6/1989 | Markowicz |
| 4,844,464 | A | 7/1989 | Berge |
| 4,856,787 | A | 8/1989 | Itkis |
| 4,871,171 | A | 10/1989 | Rivero |
| 4,880,237 | A | 11/1989 | Kishishita |
| 4,926,327 | A | 5/1990 | Sidley |
| 4,964,638 | A | 10/1990 | Ishida |
| 4,991,848 | A | 2/1991 | Greenwood et al. |
| 5,019,973 | A | 5/1991 | Wilcox et al. |
| 5,033,744 | A | 7/1991 | Bridgeman et al. |
| 5,038,022 | A | 8/1991 | Lucero |
| 5,046,737 | A | 9/1991 | Fienberg |
| 5,048,833 | A | 9/1991 | Lamle |
| 5,058,893 | A | 10/1991 | Bertram et al. |
| 5,074,559 | A | 12/1991 | Okada |
| 5,092,598 | A | 3/1992 | Kamille |
| 5,116,055 | A | 5/1992 | Tracy |
| 5,123,649 | A | 6/1992 | Tiberio |
| 5,127,651 | A | 7/1992 | Okada |
| 5,152,529 | A | 10/1992 | Okada |
| 5,158,293 | A | 10/1992 | Mullins |
| 5,178,390 | A | 1/1993 | Okada |
| 5,205,555 | A | 4/1993 | Hamano |
| 5,209,479 | A | 5/1993 | Nagao |
| 5,217,224 | A | 6/1993 | Sincock |
| 5,249,800 | A | 10/1993 | Hilgendorf et al. |
| 5,259,616 | A | 11/1993 | Bergmann |
| 5,265,874 | A | 11/1993 | Dickinson et al. |
| 5,275,400 | A | 1/1994 | Weingardt et al. |
| 5,276,312 | A | 1/1994 | McCarthy |
| 5,277,424 | A | 1/1994 | Wilms |
| 5,280,909 | A | 1/1994 | Tracy |
| 5,286,023 | A | 2/1994 | Wood |
| 5,292,127 | A | 3/1994 | Kelly et al. |
| 5,308,065 | A | 5/1994 | Bridgeman et al. |
| 5,321,241 | A | 6/1994 | Craine |
| 5,324,035 | A | 6/1994 | Morris et al. |
| 5,326,104 | A | 7/1994 | Pease et al. |
| 5,332,228 | A | 7/1994 | Schultz |
| 5,342,047 | A | 8/1994 | Heidel et al. |
| 5,342,049 | A | 8/1994 | Wichinsky et al. |
| 5,344,144 | A | 9/1994 | Canon |
| 5,351,970 | A | 10/1994 | Fioretti |
| 5,364,100 | A | 11/1994 | Ludlow et al. |
| 5,377,993 | A | 1/1995 | Josephs |
| 5,380,007 | A | 1/1995 | Travis et al. |
| 5,393,057 | A | 2/1995 | Marnell, II |
| 5,393,061 | A | 2/1995 | Manship et al. |
| 5,395,111 | A | 3/1995 | Inoue |
| 5,398,932 | A | 3/1995 | Eberhardt et al. |
| 5,401,024 | A | 3/1995 | Simunek |
| 5,407,200 | A | 4/1995 | Zalabah |
| 5,411,271 | A | 5/1995 | Mirando |
| 5,417,430 | A | 5/1995 | Breeding |
| 5,423,539 | A | 6/1995 | Nagao |
| 5,429,361 | A | 7/1995 | Raven et al. |
| 5,431,408 | A | 7/1995 | Adams |
| 5,449,173 | A | 9/1995 | Thomas et al. |
| 5,456,465 | A | 10/1995 | Durham |
| 5,470,079 | A | 11/1995 | LeStrange et al. |
| 5,472,194 | A | 12/1995 | Breeding et al. |
| 5,476,259 | A | 12/1995 | Weingardt |
| 5,489,101 | A | 2/1996 | Moody |
| 5,511,781 | A | 4/1996 | Wood |
| 5,524,888 | A | 6/1996 | Heidel |
| 5,531,441 | A | 7/1996 | Dabrowski et al. |
| 5,536,016 | A | 7/1996 | Thompson |
| 5,542,669 | A | 8/1996 | Charron et al. |
| 5,544,893 | A | 8/1996 | Jones et al. |
| 5,547,192 | A | 8/1996 | Ishibashi |
| 5,560,603 | A | 10/1996 | Seelig et al. |
| 5,564,700 | A | 10/1996 | Celona |
| 5,566,337 | A | 10/1996 | Szymanski |
| 5,570,885 | A | 11/1996 | Ornstein |
| 5,580,053 | A | 12/1996 | Crouch |
| 5,580,309 | A | 12/1996 | Piechowiak et al. |
| 5,584,485 | A | 12/1996 | Jone et al. |
| 5,584,763 | A | 12/1996 | Kelly et al. |
| 5,584,764 | A | 12/1996 | Inoue |
| 5,601,487 | A | 2/1997 | Oshima et al. |
| 5,605,506 | A | 2/1997 | Hoorn et al. |
| 5,609,524 | A | 3/1997 | Inoue |
| 5,611,535 | A | 3/1997 | Tiberio |
| 5,611,730 | A | 3/1997 | Weiss |
| 5,622,366 | A | 4/1997 | Inoue |
| 5,626,341 | A | 5/1997 | Jones |
| 5,639,089 | A | 6/1997 | Matsumoto et al. |
| 5,641,050 | A | 6/1997 | Smith et al. |
| 5,641,730 | A | 6/1997 | Brown |
| 5,645,486 | A | 7/1997 | Nagao et al. |
| 5,647,798 | A | 7/1997 | Falciglia |
| 5,655,961 | A | 8/1997 | Acres et al. |
| 5,664,998 | A | 9/1997 | Seelig et al. |
| 5,674,128 | A | 10/1997 | Holch et al. |
| 5,702,304 | A | 12/1997 | Acres et al. |
| 5,707,285 | A | 1/1998 | Place et al. |
| 5,707,286 | A | 1/1998 | Carlson |
| 5,711,525 | A | 1/1998 | Breeding |
| 5,720,483 | A | 2/1998 | Trinh |
| 5,722,891 | A | 3/1998 | Inoue |
| 5,732,948 | A | 3/1998 | Yoseloff |
| 5,741,183 | A | 4/1998 | Acres et al. |
| 5,743,523 | A | 4/1998 | Kelly et al. |
| 5,743,524 | A | 4/1998 | Nannicola |
| 5,743,526 | A | 4/1998 | Inoue |
| 5,743,800 | A | 4/1998 | Huard et al. |
| 5,752,881 | A | 5/1998 | Inoue |

(56) References Cited

U.S. PATENT DOCUMENTS

| | | | |
|---|---|---|---|
| 5,752,882 | A | 5/1998 | Acres et al. |
| 5,755,619 | A | 5/1998 | Matsumoto et al. |
| 5,761,647 | A | 6/1998 | Boushy |
| 5,762,552 | A | 6/1998 | Vuong |
| 5,766,076 | A | 6/1998 | Pease et al. |
| 5,769,716 | A | 6/1998 | Saffari et al. |
| 5,772,506 | A | 6/1998 | Marks et al. |
| 5,772,509 | A | 6/1998 | Weiss |
| 5,772,511 | A | 6/1998 | Smeltzer |
| RE35,864 | E | 7/1998 | Weingardt |
| 5,775,692 | A | 7/1998 | Watts et al. |
| 5,779,544 | A | 7/1998 | Seelig et al. |
| 5,779,545 | A | 7/1998 | Berg et al. |
| 5,779,547 | A | 7/1998 | SoRelle et al. |
| 5,779,549 | A | 7/1998 | Walker et al. |
| 5,788,573 | A | 8/1998 | Baerlocher et al. |
| 5,800,269 | A | 9/1998 | Holch et al. |
| 5,806,855 | A | 9/1998 | Cherry |
| 5,807,172 | A | 9/1998 | Piechowiak |
| 5,816,918 | A | 10/1998 | Kelly et al. |
| 5,820,459 | A | 10/1998 | Acres et al. |
| 5,823,872 | A | 10/1998 | Prather et al. |
| 5,823,873 | A | 10/1998 | Moody |
| 5,823,874 | A | 10/1998 | Adams |
| D400,597 | S | 11/1998 | Hedrick et al. |
| 5,833,536 | A | 11/1998 | Davids et al. |
| 5,833,537 | A | 11/1998 | Barrie |
| 5,833,538 | A | 11/1998 | Weiss |
| 5,833,540 | A | 11/1998 | Miodunski et al. |
| 5,836,817 | A | 11/1998 | Acres et al. |
| D402,702 | S | 12/1998 | Seelig et al. |
| 5,848,932 | A | 12/1998 | Adams |
| 5,851,011 | A | 12/1998 | Lott |
| 5,851,148 | A | 12/1998 | Brune et al. |
| 5,851,149 | A | 12/1998 | Xidos et al. |
| 5,855,514 | A | 1/1999 | Kamille |
| 5,855,515 | A | 1/1999 | Pease et al. |
| 5,863,249 | A | 1/1999 | Inoue |
| 5,873,781 | A | 2/1999 | Keane |
| D406,865 | S | 3/1999 | Heidel |
| 5,876,284 | A | 3/1999 | Acres et al. |
| 5,882,261 | A | 3/1999 | Adams |
| 5,885,157 | A | 3/1999 | Harada et al. |
| 5,885,158 | A | 3/1999 | Torango et al. |
| 5,890,962 | A | 4/1999 | Takemoto |
| 5,893,718 | A | 4/1999 | O'Donnell |
| 5,902,184 | A | 5/1999 | Bennett |
| 5,902,983 | A | 5/1999 | Crevelt et al. |
| 5,910,048 | A | 6/1999 | Feinburg |
| 5,911,418 | A | 6/1999 | Adams et al. |
| 5,919,088 | A | 7/1999 | Weiss |
| 5,927,714 | A | 7/1999 | Kaplan |
| 5,934,672 | A | 8/1999 | Sines et al. |
| 5,935,002 | A | 8/1999 | Falciglia |
| 5,941,773 | A | 8/1999 | Harlick |
| 5,944,606 | A | 8/1999 | Gerow |
| 5,947,820 | A | 9/1999 | Morro et al. |
| 5,947,822 | A | 9/1999 | Weiss |
| 5,951,011 | A | 9/1999 | Potter et al. |
| 5,951,397 | A | 9/1999 | Dickinson |
| 5,964,463 | A | 10/1999 | Moore, Jr. |
| 5,967,894 | A | 10/1999 | Kinoshita et al. |
| 5,976,015 | A | 11/1999 | Seelig et al. |
| 5,976,016 | A | 11/1999 | Moody et al. |
| 5,980,384 | A | 11/1999 | Barrie |
| 5,984,779 | A | 11/1999 | Bridgeman et al. |
| 5,984,781 | A | 11/1999 | Sunaga |
| 5,984,782 | A | 11/1999 | Inoue |
| 5,989,121 | A | 11/1999 | Sakamoto |
| 5,993,316 | A | 11/1999 | Coyle et al. |
| 5,997,400 | A | 12/1999 | Seelig et al. |
| 5,997,401 | A | 12/1999 | Crawford |
| 6,001,016 | A | 12/1999 | Walker et al. |
| 6,004,207 | A | 12/1999 | Wilson, Jr. et al. |
| 6,007,066 | A | 12/1999 | Moody |
| 6,007,427 | A | 12/1999 | Wiener |
| 6,012,982 | A | 1/2000 | Piechowiak et al. |
| 6,015,346 | A | 1/2000 | Bennett |
| 6,016,338 | A | 1/2000 | Bansal et al. |
| 6,019,369 | A | 2/2000 | Nakagawa et al. |
| 6,033,307 | A | 3/2000 | Vancura |
| 6,039,648 | A | 3/2000 | Guinn et al. |
| 6,039,649 | A | 3/2000 | Schulze |
| 6,045,129 | A | 4/2000 | Cooper et al. |
| 6,047,963 | A | 4/2000 | Pierce et al. |
| 6,048,269 | A | 4/2000 | Burns et al. |
| 6,050,895 | A | 4/2000 | Luciano et al. |
| 6,056,642 | A | 5/2000 | Bennett |
| 6,059,289 | A | 5/2000 | Vancura |
| 6,059,658 | A | 5/2000 | Mangano et al. |
| 6,062,979 | A | 5/2000 | Inoue |
| 6,062,980 | A | 5/2000 | Luciano |
| 6,062,981 | A | 5/2000 | Luciano, Jr. |
| 6,068,553 | A | 5/2000 | Parker |
| 6,077,162 | A | 6/2000 | Weiss |
| 6,080,062 | A | 6/2000 | Olson |
| 6,086,066 | A | 7/2000 | Takeuchi et al. |
| 6,089,976 | A | 7/2000 | Schneider et al. |
| 6,089,977 | A | 7/2000 | Bennett |
| 6,089,978 | A | 7/2000 | Adams |
| 6,089,980 | A | 7/2000 | Gauselmann |
| 6,093,102 | A | 7/2000 | Bennett |
| 6,099,408 | A | 8/2000 | Schneier et al. |
| 6,102,400 | A | 8/2000 | Scott et al. |
| 6,102,798 | A | 8/2000 | Bennett |
| 6,105,962 | A | 8/2000 | Malavazos et al. |
| 6,110,039 | A | 8/2000 | Oh |
| 6,110,041 | A | 8/2000 | Walker et al. |
| 6,110,043 | A | 8/2000 | Olsen |
| 6,113,098 | A | 9/2000 | Adams |
| 6,117,009 | A | 9/2000 | Yoseloff |
| 6,117,013 | A | 9/2000 | Eiba |
| 6,120,031 | A | 9/2000 | Adams |
| 6,120,377 | A | 9/2000 | McGinnis, Sr. et al. |
| 6,120,378 | A | 9/2000 | Moody et al. |
| 6,126,541 | A | 10/2000 | Fuchs |
| 6,126,542 | A | 10/2000 | Fier |
| 6,126,547 | A | 10/2000 | Ishimoto |
| 6,129,355 | A | 10/2000 | Hahn et al. |
| 6,135,884 | A | 10/2000 | Hedrick et al. |
| 6,135,885 | A | 10/2000 | Lermusiaux |
| 6,139,013 | A | 10/2000 | Pierce et al. |
| 6,142,872 | A | 11/2000 | Walker et al. |
| 6,142,873 | A | 11/2000 | Weiss et al. |
| 6,142,874 | A | 11/2000 | Kodachi et al. |
| 6,142,875 | A | 11/2000 | Kodachi et al. |
| 6,146,273 | A | 11/2000 | Olsen |
| 6,149,156 | A | 11/2000 | Feola |
| 6,149,157 | A | 11/2000 | Suan |
| 6,149,521 | A | 11/2000 | Sanduski |
| 6,152,823 | A | 11/2000 | Lacoste et al. |
| 6,155,925 | A | 12/2000 | Giobbi et al. |
| 6,159,095 | A | 12/2000 | Frohm et al. |
| 6,159,096 | A | 12/2000 | Yoseloff |
| 6,159,097 | A | 12/2000 | Gura |
| 6,159,098 | A | 12/2000 | Slomiany et al. |
| 6,162,121 | A | 12/2000 | Morro et al. |
| 6,162,122 | A | 12/2000 | Acres et al. |
| 6,165,070 | A | 12/2000 | Nolte et al. |
| 6,168,520 | B1 | 1/2001 | Baerlocher et al. |
| 6,168,523 | B1 | 1/2001 | Piechowiak et al. |
| 6,173,955 | B1 | 1/2001 | Perrie et al. |
| 6,174,233 | B1 | 1/2001 | Sunaga et al. |
| 6,174,235 | B1 | 1/2001 | Walker et al. |
| 6,183,366 | B1 | 2/2001 | Goldberg et al. |
| 6,186,894 | B1 | 2/2001 | Mayeroff |
| 6,190,254 | B1 | 2/2001 | Bennett |
| 6,190,255 | B1 | 2/2001 | Thomas et al. |
| 6,193,606 | B1 | 2/2001 | Walker et al. |
| 6,203,010 | B1 | 3/2001 | Jorasch et al. |
| 6,203,429 | B1 | 3/2001 | Demar et al. |
| 6,203,430 | B1 | 3/2001 | Walker et al. |
| 6,206,374 | B1 | 3/2001 | Jones |
| D441,031 | S | 4/2001 | Seelig et al. |

(56) References Cited

U.S. PATENT DOCUMENTS

| | | | |
|---|---|---|---|
| 6,210,275 | B1 | 4/2001 | Olsen |
| 6,210,277 | B1 | 4/2001 | Stefan |
| 6,210,279 | B1 | 4/2001 | Dickinson |
| 6,213,876 | B1 | 4/2001 | Moore, Jr. |
| 6,217,448 | B1 | 4/2001 | Olsen |
| 6,220,593 | B1 | 4/2001 | Pierce et al. |
| 6,220,959 | B1 | 4/2001 | Holmes, Jr. et al. |
| 6,220,961 | B1 | 4/2001 | Keane et al. |
| 6,224,482 | B1 | 5/2001 | Bennett |
| 6,224,483 | B1 | 5/2001 | Mayeroff |
| 6,224,484 | B1 | 5/2001 | Okuda et al. |
| 6,227,970 | B1 | 5/2001 | Shimizu et al. |
| 6,227,971 | B1 | 5/2001 | Weiss |
| 6,231,442 | B1 | 5/2001 | Mayeroff |
| 6,231,445 | B1 | 5/2001 | Acres |
| 6,234,879 | B1 | 5/2001 | Hasegawa et al. |
| 6,234,897 | B1 | 5/2001 | Frohm et al. |
| 6,238,287 | B1 | 5/2001 | Komori et al. |
| 6,238,288 | B1 | 5/2001 | Walker et al. |
| D443,313 | S | 6/2001 | Brettschneider |
| 6,241,608 | B1 | 6/2001 | Torango |
| 6,244,958 | B1 | 6/2001 | Acres |
| 6,251,013 | B1 | 6/2001 | Bennett |
| 6,254,481 | B1 | 7/2001 | Jaffe |
| 6,254,483 | B1 | 7/2001 | Acres |
| 6,257,981 | B1 | 7/2001 | Acres et al. |
| 6,261,128 | B1 | 7/2001 | Heim et al. |
| 6,261,177 | B1 | 7/2001 | Bennett |
| 6,264,557 | B1 | 7/2001 | Schneier et al. |
| 6,267,669 | B1 | 7/2001 | Luciano, Jr. et al. |
| 6,270,409 | B1 | 8/2001 | Shuster |
| 6,270,411 | B1 | 8/2001 | Gura et al. |
| 6,270,412 | B1 | 8/2001 | Crawford et al. |
| 6,287,202 | B1 | 9/2001 | Pascal et al. |
| 6,293,866 | B1 | 9/2001 | Walker et al. |
| RE37,414 | E | 10/2001 | Harlick |
| 6,299,165 | B1 | 10/2001 | Nagano |
| 6,299,170 | B1 | 10/2001 | Yoseloff |
| 6,302,398 | B1 | 10/2001 | Vecchio |
| 6,302,790 | B1 | 10/2001 | Brossard |
| 6,302,793 | B1 | 10/2001 | Fertitta, III et al. |
| 6,305,686 | B1 | 10/2001 | Perrie et al. |
| 6,309,298 | B1 | 10/2001 | Gerow |
| 6,309,299 | B1 | 10/2001 | Weiss |
| 6,309,300 | B1 | 10/2001 | Glavich |
| 6,311,976 | B1 | 11/2001 | Yoseloff et al. |
| 6,312,330 | B1 | 11/2001 | Jones et al. |
| 6,312,333 | B1 | 11/2001 | Acres |
| 6,312,334 | B1 | 11/2001 | Yoseloff |
| 6,315,660 | B1 | 11/2001 | DeMar et al. |
| 6,315,662 | B1 | 11/2001 | Jorasch et al. |
| 6,315,663 | B1 | 11/2001 | Sakamoto |
| 6,315,664 | B1 | 11/2001 | Baerlocher et al. |
| 6,319,122 | B1 | 11/2001 | Packes, Jr. et al. |
| 6,319,123 | B1 | 11/2001 | Paludi |
| 6,319,124 | B1 | 11/2001 | Baerlocher et al. |
| 6,319,125 | B1 | 11/2001 | Acres |
| 6,322,078 | B1 | 11/2001 | Adams |
| 6,322,309 | B1 | 11/2001 | Thomas et al. |
| 6,328,649 | B1 | 12/2001 | Randall et al. |
| 6,334,814 | B1 | 1/2002 | Adams |
| 6,336,857 | B1 | 1/2002 | McBride |
| 6,336,860 | B1 | 1/2002 | Webb |
| 6,336,863 | B1 | 1/2002 | Baerlocher et al. |
| 6,338,678 | B1 | 1/2002 | Seelig et al. |
| 6,340,158 | B2 | 1/2002 | Pierce et al. |
| 6,343,989 | B1 | 2/2002 | Wood et al. |
| 6,346,043 | B1 | 2/2002 | Colin et al. |
| 6,347,738 | B1 | 2/2002 | Crevelt et al. |
| 6,347,996 | B1 | 2/2002 | Gilmore et al. |
| 6,358,144 | B1 | 3/2002 | Kadlic et al. |
| 6,358,149 | B1 | 3/2002 | Schneider et al. |
| 6,361,441 | B1 | 3/2002 | Walker et al. |
| 6,364,766 | B1 | 4/2002 | Anderson et al. |
| 6,364,767 | B1 | 4/2002 | Brossard et al. |
| 6,364,768 | B1 | 4/2002 | Acres et al. |
| 6,364,769 | B1 | 4/2002 | Weiss et al. |
| 6,368,216 | B1 | 4/2002 | Hedrick et al. |
| 6,368,218 | B2 | 4/2002 | Angell, Jr. |
| 6,371,852 | B1 | 4/2002 | Acres |
| 6,375,187 | B1 | 4/2002 | Baerlocher et al. |
| 6,375,567 | B1 | 4/2002 | Acres |
| 6,375,568 | B1 | 4/2002 | Roffman et al. |
| 6,375,569 | B1 | 4/2002 | Acres |
| 6,375,570 | B1 | 4/2002 | Poole |
| 6,386,974 | B1 | 5/2002 | Adams |
| 6,386,977 | B1 | 5/2002 | Hole |
| 6,398,218 | B1 | 6/2002 | Vancura |
| 6,398,220 | B1 | 6/2002 | Inoue |
| 6,398,644 | B1 | 6/2002 | Perrie et al. |
| 6,398,645 | B1 | 6/2002 | Yoseloff |
| 6,406,369 | B1 | 6/2002 | Baerlocher et al. |
| 6,413,160 | B1 | 7/2002 | Vancura |
| 6,416,408 | B2 | 7/2002 | Tracy et al. |
| 6,416,409 | B1 | 7/2002 | Jordan |
| 6,419,579 | B1 | 7/2002 | Bennett |
| 6,419,583 | B1 | 7/2002 | Crumby et al. |
| 6,428,412 | B1 | 8/2002 | Anderson et al. |
| 6,431,983 | B2 | 8/2002 | Acres |
| 6,435,500 | B2 | 8/2002 | Guimina |
| 6,435,511 | B1 | 8/2002 | Vancura et al. |
| 6,435,968 | B1 | 8/2002 | Torango |
| 6,439,993 | B1 | 8/2002 | O'Halloran |
| 6,439,995 | B1 | 8/2002 | Hughs-Baird et al. |
| 6,443,452 | B1 | 9/2002 | Brune |
| 6,443,837 | B1 | 9/2002 | Jaffe et al. |
| 6,450,884 | B1 | 9/2002 | Seelig et al. |
| 6,454,266 | B1 | 9/2002 | Breeding et al. |
| 6,454,651 | B1 | 9/2002 | Yoseloff |
| RE37,885 | E | 10/2002 | Acres et al. |
| 6,461,241 | B1 | 10/2002 | Webb et al. |
| 6,464,582 | B1 | 10/2002 | Baerlocher et al. |
| 6,471,208 | B2 | 10/2002 | Yoseloff et al. |
| 6,471,591 | B1 | 10/2002 | Crumby |
| D465,531 | S | 11/2002 | Luciano, Jr. et al. |
| 6,481,713 | B2 | 11/2002 | Perrie et al. |
| 6,482,089 | B2 | 11/2002 | Demar et al. |
| 6,491,584 | B2 | 12/2002 | Graham et al. |
| 6,494,454 | B2 | 12/2002 | Adams |
| 6,506,118 | B1 | 1/2003 | Baerlocher et al. |
| 6,508,707 | B2 | 1/2003 | DeMar et al. |
| 6,511,375 | B1 | 1/2003 | Kaminkow |
| 6,511,376 | B2 | 1/2003 | Walker et al. |
| 6,514,141 | B1 | 2/2003 | Kaminkow et al. |
| 6,533,273 | B2 | 3/2003 | Cole et al. |
| 6,533,658 | B1 | 3/2003 | Walker et al. |
| 6,533,660 | B2 | 3/2003 | Seelig et al. |
| 6,533,664 | B1 | 3/2003 | Crumby |
| 6,537,150 | B1 | 3/2003 | Luciano et al. |
| 6,537,152 | B2 | 3/2003 | Seelig et al. |
| 6,546,134 | B1 | 4/2003 | Shrairman et al. |
| 6,546,374 | B1 | 4/2003 | Esposito et al. |
| 6,547,131 | B1 | 4/2003 | Foodman et al. |
| 6,547,242 | B1 | 4/2003 | Sugiyama et al. |
| 6,554,283 | B2 | 4/2003 | Vancura et al. |
| 6,554,705 | B1 | 4/2003 | Cumbers |
| 6,561,904 | B2 | 5/2003 | Locke et al. |
| 6,565,434 | B1 | 5/2003 | Acres |
| 6,565,436 | B1 | 5/2003 | Baerlocher |
| 6,569,015 | B1 | 5/2003 | Baerlocher et al. |
| 6,572,471 | B1 | 6/2003 | Bennett |
| 6,575,830 | B2 | 6/2003 | Baerlocher et al. |
| 6,575,832 | B1 | 6/2003 | Manfredi et al. |
| 6,582,307 | B2 | 6/2003 | Webb |
| 6,589,115 | B2 | 7/2003 | Walker et al. |
| 6,592,460 | B2 | 7/2003 | Torango |
| 6,595,853 | B1 | 7/2003 | Osawa |
| 6,595,854 | B2 | 7/2003 | Hughs-Baird et al. |
| 6,599,185 | B1 | 7/2003 | Kaminkow et al. |
| 6,599,190 | B2 | 7/2003 | Osawa |
| 6,599,193 | B2 | 7/2003 | Baerlocher et al. |
| 6,602,135 | B1 | 8/2003 | Gerrard |
| 6,602,137 | B2 | 8/2003 | Kaminkow et al. |
| 6,604,740 | B1 | 8/2003 | Singer et al. |

(56) References Cited

U.S. PATENT DOCUMENTS

| | | | |
|---|---|---|---|
| 6,607,437 | B2 | 8/2003 | Casey et al. |
| 6,607,441 | B1 | 8/2003 | Acres |
| 6,609,971 | B2 | 8/2003 | Vancura |
| 6,609,972 | B2 | 8/2003 | Seelig et al. |
| 6,609,973 | B1 | 8/2003 | Weiss |
| 6,616,142 | B2 | 9/2003 | Adams |
| 6,616,531 | B1 | 9/2003 | Mullins |
| 6,620,046 | B2 | 9/2003 | Rowe |
| 6,626,758 | B1 | 9/2003 | Parham et al. |
| 6,634,944 | B2 | 10/2003 | Osawa |
| 6,637,747 | B1 | 10/2003 | Garrod |
| 6,645,073 | B2 | 11/2003 | Lemay et al. |
| 6,645,077 | B2 | 11/2003 | Rowe |
| 6,648,759 | B2 | 11/2003 | Vancura |
| 6,652,378 | B2 | 11/2003 | Cannon et al. |
| 6,656,040 | B1 | 12/2003 | Brosnan et al. |
| 6,656,043 | B2 | 12/2003 | Seelig et al. |
| 6,656,047 | B1 | 12/2003 | Tarantino et al. |
| 6,656,048 | B2 | 12/2003 | Olsen |
| 6,656,052 | B2 | 12/2003 | Abramopoulos et al. |
| 6,659,864 | B2 | 12/2003 | McGahn et al. |
| 6,666,765 | B2 | 12/2003 | Vancura |
| 6,672,959 | B2 | 1/2004 | Moody et al. |
| 6,675,152 | B1 | 1/2004 | Prasad et al. |
| 6,682,419 | B2 | 1/2004 | Webb et al. |
| 6,682,420 | B2 | 1/2004 | Webb et al. |
| 6,688,977 | B1 | 2/2004 | Baerlocher et al. |
| 6,692,355 | B2 | 2/2004 | Baerlocher et al. |
| 6,712,694 | B1 | 3/2004 | Nordman |
| 6,712,695 | B2 | 3/2004 | Mothwurf et al. |
| 6,712,697 | B2 | 3/2004 | Acres |
| 6,715,756 | B2 | 4/2004 | Inoue |
| 6,719,630 | B1 | 4/2004 | Seelig et al. |
| 6,726,204 | B2 | 4/2004 | Inoue |
| 6,726,563 | B1 | 4/2004 | Baerlocher et al. |
| 6,746,328 | B2 | 6/2004 | Cannon et al. |
| 6,749,504 | B2 | 6/2004 | Hughs-Baird |
| 6,749,510 | B2 | 6/2004 | Giobbi |
| 6,754,346 | B2 | 6/2004 | Eiserling et al. |
| 6,761,632 | B2 | 7/2004 | Nolz et al. |
| 6,776,714 | B2 | 8/2004 | Ungaro et al. |
| 6,776,715 | B2 | 8/2004 | Price |
| 6,790,141 | B2 | 9/2004 | Muir |
| 6,800,030 | B2 | 10/2004 | Acres |
| 6,805,352 | B2 | 10/2004 | Hunter |
| 6,811,483 | B1 | 11/2004 | Webb et al. |
| 6,832,956 | B1 | 12/2004 | Boyd et al. |
| 6,832,958 | B2 | 12/2004 | Acres et al. |
| 6,837,788 | B2 | 1/2005 | Cannon |
| 6,866,583 | B2 | 3/2005 | Glavich et al. |
| 6,869,361 | B2 | 3/2005 | Sharpless et al. |
| 6,884,168 | B2 | 4/2005 | Wood et al. |
| 6,887,154 | B1 | 5/2005 | Luciano, Jr. et al. |
| 6,889,849 | B2 | 5/2005 | Heidel et al. |
| 6,899,625 | B2 | 5/2005 | Luciano, Jr. et al. |
| 6,905,406 | B2 | 6/2005 | Kaminkow et al. |
| 6,908,387 | B2 | 6/2005 | Hedrick et al. |
| 6,910,964 | B2 | 6/2005 | Acres |
| 6,913,532 | B2 | 7/2005 | Baerlocher et al. |
| 6,918,832 | B2 | 7/2005 | Baerlocher et al. |
| 6,918,834 | B2 | 7/2005 | Vancura |
| 6,935,951 | B2 | 8/2005 | Paulsen et al. |
| 6,935,958 | B2 | 8/2005 | Nelson |
| 6,939,234 | B2 | 9/2005 | Beatty |
| 6,942,574 | B1 | 9/2005 | LeMay et al. |
| RE38,812 | E | 10/2005 | Acres et al. |
| 6,955,600 | B2 | 10/2005 | Glavich et al. |
| 6,966,834 | B1 | 11/2005 | Johnson |
| 7,029,395 | B1 | 4/2006 | Baerlocher |
| 7,169,042 | B2 | 1/2007 | Muir et al. |
| 2001/0024971 | A1 | 9/2001 | Brossard |
| 2001/0049303 | A1 | 12/2001 | Found |
| 2001/0055990 | A1 | 12/2001 | Acres |
| 2002/0002674 | A1 | 1/2002 | Grimes et al. |
| 2002/0045472 | A1 | 4/2002 | Adams |
| 2002/0045475 | A1 | 4/2002 | Glavich et al. |
| 2002/0071557 | A1 | 6/2002 | Nguyen |
| 2002/0094855 | A1 | 7/2002 | Berman |
| 2002/0094862 | A1 | 7/2002 | Inoue |
| 2002/0116615 | A1 | 8/2002 | Nguyen et al. |
| 2002/0138594 | A1 | 9/2002 | Rowe |
| 2002/0142822 | A1 | 10/2002 | Baerlocher et al. |
| 2002/0142829 | A1 | 10/2002 | Inoue |
| 2002/0152120 | A1 | 10/2002 | Howington |
| 2002/0155880 | A1 | 10/2002 | Glavich et al. |
| 2002/0165023 | A1 | 11/2002 | Brosnan et al. |
| 2002/0187834 | A1 | 12/2002 | Rowe et al. |
| 2002/0198036 | A1 | 12/2002 | Baerlocher et al. |
| 2003/0027625 | A1 | 2/2003 | Rowe |
| 2003/0027630 | A1 | 2/2003 | Kelly et al. |
| 2003/0040355 | A1 | 2/2003 | Baerlocher |
| 2003/0040358 | A1 | 2/2003 | Rothkranz et al. |
| 2003/0040360 | A1 | 2/2003 | Kaminkow |
| 2003/0045348 | A1 | 3/2003 | Palmer et al. |
| 2003/0045350 | A1 | 3/2003 | Baerlocher et al. |
| 2003/0045353 | A1 | 3/2003 | Paulsen et al. |
| 2003/0050111 | A1 | 3/2003 | Saffari |
| 2003/0054875 | A1 | 3/2003 | Marks et al. |
| 2003/0054878 | A1 | 3/2003 | Benoy et al. |
| 2003/0060254 | A1 | 3/2003 | Cuddy et al. |
| 2003/0060266 | A1 | 3/2003 | Baerlocher |
| 2003/0060267 | A1 | 3/2003 | Glavich et al. |
| 2003/0060269 | A1 | 3/2003 | Paulsen et al. |
| 2003/0060272 | A1 | 3/2003 | Glavich et al. |
| 2003/0060279 | A1 | 3/2003 | Torango |
| 2003/0064772 | A1 | 4/2003 | Tempest et al. |
| 2003/0064773 | A1 | 4/2003 | Baerlocher et al. |
| 2003/0064785 | A1 | 4/2003 | Stone et al. |
| 2003/0064790 | A1 | 4/2003 | Hughs-Baird et al. |
| 2003/0069056 | A1 | 4/2003 | Cormack et al. |
| 2003/0069064 | A1 | 4/2003 | Ainsworth |
| 2003/0073482 | A1 | 4/2003 | Baerlocher et al. |
| 2003/0078089 | A1 | 4/2003 | Gray et al. |
| 2003/0083943 | A1 | 5/2003 | Adams et al. |
| 2003/0092484 | A1 | 5/2003 | Schneider et al. |
| 2003/0104853 | A1 | 6/2003 | Tessmer et al. |
| 2003/0119583 | A1 | 6/2003 | Kaminkow et al. |
| 2003/0144965 | A1 | 7/2003 | Prasad et al. |
| 2003/0162584 | A1 | 8/2003 | Hughs-Baird et al. |
| 2003/0162585 | A1 | 8/2003 | Bigelow, Jr. et al. |
| 2003/0181231 | A1 | 9/2003 | Vancura et al. |
| 2003/0182574 | A1 | 9/2003 | Whitten et al. |
| 2003/0195027 | A1 | 10/2003 | Baerlocher et al. |
| 2003/0199321 | A1 | 10/2003 | Williams |
| 2003/0207709 | A1 | 11/2003 | Paotrakul |
| 2003/0207710 | A1 | 11/2003 | Rodgers et al. |
| 2003/0211879 | A1 | 11/2003 | Englman |
| 2003/0211884 | A1 | 11/2003 | Gauselmann |
| 2003/0216166 | A1 | 11/2003 | Baerlocher et al. |
| 2003/0222402 | A1 | 12/2003 | Olive |
| 2003/0223803 | A1 | 12/2003 | De Schrijver |
| 2003/0228904 | A1 | 12/2003 | Acres et al. |
| 2003/0232643 | A1 | 12/2003 | Inoue |
| 2003/0232647 | A1 | 12/2003 | Moser |
| 2003/0236116 | A1 | 12/2003 | Marks et al. |
| 2004/0000754 | A1 | 1/2004 | Inoue |
| 2004/0002372 | A1 | 1/2004 | Rodgers et al. |
| 2004/0009807 | A1 | 1/2004 | Miller et al. |
| 2004/0009811 | A1 | 1/2004 | Torango |
| 2004/0012145 | A1 | 1/2004 | Inoue |
| 2004/0014516 | A1 | 1/2004 | Inoue |
| 2004/0014517 | A1 | 1/2004 | Inoue |
| 2004/0017041 | A1 | 1/2004 | Inoue |
| 2004/0018866 | A1 | 1/2004 | Inoue |
| 2004/0026854 | A1 | 2/2004 | Inoue |
| 2004/0029631 | A1 | 2/2004 | Duhamel |
| 2004/0036218 | A1 | 2/2004 | Inoue |
| 2004/0038726 | A1 | 2/2004 | Inoue |
| 2004/0041340 | A1 | 3/2004 | Inoue |
| 2004/0048644 | A1 | 3/2004 | Gerrard et al. |
| 2004/0048649 | A1 | 3/2004 | Peterson et al. |
| 2004/0048652 | A1 | 3/2004 | Ching et al. |
| 2004/0053658 | A1 | 3/2004 | Rothranz |
| 2004/0053659 | A1 | 3/2004 | Rothkranz et al. |

(56) References Cited

U.S. PATENT DOCUMENTS

| | | | |
|---|---|---|---|
| 2004/0053670 | A1 | 3/2004 | Rothkranz et al. |
| 2004/0053671 | A1 | 3/2004 | Nordman |
| 2004/0053672 | A1 | 3/2004 | Baerlocher |
| 2004/0053673 | A1 | 3/2004 | Mishra |
| 2004/0053683 | A1 | 3/2004 | Hartl et al. |
| 2004/0053687 | A1 | 3/2004 | Nordman et al. |
| 2004/0072615 | A1 | 4/2004 | Maya et al. |
| 2004/0072619 | A1 | 4/2004 | Brosnan et al. |
| 2004/0087368 | A1 | 5/2004 | Gavselmann |
| 2004/0121840 | A1 | 6/2004 | Rosander et al. |
| 2004/0137982 | A1 | 7/2004 | Cuddy et al. |
| 2004/0147306 | A1 | 7/2004 | Randall et al. |
| 2004/0150161 | A1 | 8/2004 | Inoue |
| 2004/0152509 | A1 | 8/2004 | Hornik et al. |
| 2004/0155399 | A1 | 8/2004 | Inoue |
| 2004/0157658 | A1 | 8/2004 | Rothkranz |
| 2004/0171416 | A1 | 9/2004 | Baerlocher et al. |
| 2004/0171420 | A1 | 9/2004 | Baerlocher et al. |
| 2004/0180715 | A1 | 9/2004 | Nordman |
| 2004/0183251 | A1 | 9/2004 | Inoue |
| 2004/0235552 | A1 | 11/2004 | Gauselmann |
| 2004/0242297 | A1 | 12/2004 | Walker et al. |
| 2005/0026694 | A1 | 2/2005 | Kelly et al. |
| 2005/0032573 | A1 | 2/2005 | Acres et al. |
| 2005/0053672 | A1 | 3/2005 | West |
| 2005/0054429 | A1 | 3/2005 | Baerlocher et al. |
| 2005/0070356 | A1 | 3/2005 | Mothwurf |
| 2005/0075163 | A1 | 4/2005 | Cuddy et al. |
| 2005/0079908 | A1 | 4/2005 | Pacey |
| 2005/0079911 | A1 | 4/2005 | Nakatsu |
| 2005/0086478 | A1 | 4/2005 | Peinado et al. |
| 2005/0101374 | A1 | 5/2005 | Acres |
| 2005/0101375 | A1 | 5/2005 | Webb et al. |
| 2005/0101384 | A1 | 5/2005 | Parham |
| 2005/0119047 | A1 | 6/2005 | Olive |
| 2005/0143168 | A1 | 6/2005 | Torango |
| 2005/0143169 | A1 | 6/2005 | Nguyen et al. |
| 2005/0159211 | A1 | 7/2005 | Englman |
| 2005/0163377 | A1 | 7/2005 | Walch |
| 2005/0176488 | A1 | 8/2005 | Olive |
| 2005/0178716 | A1 | 8/2005 | Suri |
| 2005/0192083 | A1 | 9/2005 | Iwamoto |
| 2005/0192099 | A1 | 9/2005 | Nguyen et al. |
| 2005/0197180 | A1 | 9/2005 | Kaminkow et al. |
| 2005/0209004 | A1 | 9/2005 | Torango |
| 2005/0227754 | A1 | 10/2005 | Kaminkow et al. |
| 2005/0239542 | A1 | 10/2005 | Olsen |
| 2005/0267610 | A1 | 12/2005 | Shinoda |
| 2005/0282626 | A1 | 12/2005 | Manfredi et al. |
| 2006/0003829 | A1 | 1/2006 | Thomas |
| 2006/0009285 | A1 | 1/2006 | Pryzby et al. |
| 2006/0025201 | A1 | 2/2006 | Van Asdale |
| 2006/0025210 | A1 | 2/2006 | Johnson |
| 2006/0026604 | A1 | 2/2006 | Tan et al. |
| 2006/0030397 | A1 | 2/2006 | Chan |
| 2006/0035694 | A1 | 2/2006 | Fuller |
| 2006/0035706 | A1 | 2/2006 | Thomas et al. |
| 2006/0036552 | A1 | 2/2006 | Gunyakti et al. |
| 2006/0040732 | A1 | 2/2006 | Baerlocher et al. |
| 2006/0040736 | A1 | 2/2006 | Baerlocher et al. |
| 2006/0052159 | A1 | 3/2006 | Cahill et al. |
| 2006/0052161 | A1 | 3/2006 | Soukup et al. |
| 2006/0052162 | A1 | 3/2006 | Soukup et al. |
| 2006/0068897 | A1 | 3/2006 | Sanford et al. |
| 2006/0073884 | A1 | 4/2006 | Walker et al. |
| 2006/0073889 | A1 | 4/2006 | Edidin et al. |
| 2006/0073897 | A1 | 4/2006 | Englman et al. |
| 2006/0178203 | A1 | 8/2006 | Hughes et al. |
| 2007/0060319 | A1 | 3/2007 | Block et al. |

FOREIGN PATENT DOCUMENTS

| | | | |
|---|---|---|---|
| AU | 567001 | | 11/1987 |
| AU | 585160 | | 6/1989 |
| AU | 589158 | | 10/1989 |
| AU | 593059 | | 2/1990 |
| AU | 630112 | | 3/1990 |
| AU | 628330 | | 9/1992 |
| AU | 633469 | | 1/1993 |
| AU | 649009 | | 5/1994 |
| AU | 655801 | | 1/1995 |
| AU | 1996 70247 | | 4/1997 |
| AU | 680920 | | 8/1997 |
| AU | 1997 16432 | | 9/1997 |
| AU | 1997 17601 | B2 | 9/1997 |
| AU | 1996 50327 | A | 10/1997 |
| AU | 1997 47657 | B2 | 6/1998 |
| AU | 1998 63553 | A | 10/1998 |
| AU | 1998 84162 | A1 | 3/1999 |
| AU | 707687 | | 7/1999 |
| AU | 1999 17318 | A1 | 9/1999 |
| AU | 709724 | | 9/1999 |
| AU | 711501 | | 10/1999 |
| AU | 716299 | | 2/2000 |
| AU | 721968 | | 7/2000 |
| AU | 722107 | | 7/2000 |
| AU | 728788 | | 1/2001 |
| AU | 2001 1000032 | | 11/2001 |
| AU | 2001 1000033 | | 11/2001 |
| AU | 748263 | | 5/2002 |
| AU | 749222 | | 6/2002 |
| AU | 754689 | | 11/2002 |
| AU | 758306 | | 3/2003 |
| AU | 1999 43453 | C | 4/2003 |
| DE | 3415114 | | 11/1985 |
| DE | 8710757 | | 11/1987 |
| DE | 3638100 | | 11/1988 |
| DE | 3917683 | | 12/1990 |
| DE | 4200254 | | 8/1993 |
| DE | 4301855 | | 7/1994 |
| DE | 19600787 | C2 | 5/1997 |
| DE | 19613455 | C2 | 8/1997 |
| DE | 19936196 | A1 | 1/2001 |
| DE | 37008861 | A1 | 8/2004 |
| EP | 0 342 797 | | 11/1989 |
| EP | 0 444 932 | | 2/1991 |
| EP | 0 449 433 | A2 | 10/1991 |
| EP | 0 798 676 | A1 | 10/1997 |
| EP | 0 874 337 | A1 | 10/1998 |
| EP | 0 926 645 | A2 | 6/1999 |
| EP | 0 944 030 | A2 | 9/1999 |
| EP | 0 945 837 | A2 | 9/1999 |
| EP | 0 981 119 | A2 | 2/2000 |
| EP | 0 984 408 | A2 | 3/2000 |
| EP | 0 984 409 | A2 | 3/2000 |
| EP | 1 003 138 | A2 | 5/2000 |
| EP | 1 467 329 | A2 | 10/2004 |
| EP | 1 498 860 | A1 | 1/2005 |
| EP | 1 513 114 | A2 | 3/2005 |
| EP | 1 528 516 | A2 | 5/2005 |
| EP | 1 528 517 | A2 | 5/2005 |
| GB | 912 685 | | 12/1962 |
| GB | 2 083 936 | A | 3/1982 |
| GB | 2 096 376 | A | 10/1982 |
| GB | 2 097 160 | A | 10/1982 |
| GB | 2 100 905 | A | 1/1983 |
| GB | 2 117 155 | A | 10/1983 |
| GB | 2 117 952 | A | 10/1983 |
| GB | 2 118 445 | | 11/1983 |
| GB | 2 1144 644 | A | 3/1984 |
| GB | 2 137 392 | A | 10/1984 |
| GB | 2 139 390 | | 11/1984 |
| GB | 2 142 457 | A | 1/1985 |
| GB | 2 147 773 | | 5/1985 |
| GB | 2 148 135 | | 5/1985 |
| GB | 1 151 054 | A | 7/1985 |
| GB | 2 153 572 | a | 8/1985 |
| GB | 2 161 008 | A | 1/1986 |
| GB | 2 161 009 | A | 1/1986 |
| GB | 2 170 636 | A | 8/1986 |
| GB | 2 180 682 | A | 4/1987 |
| GB | 2 181 589 | A | 4/1987 |
| GB | 2 183 882 | A | 6/1987 |
| GB | 2 201 821 | A | 9/1987 |

(56) References Cited

FOREIGN PATENT DOCUMENTS

| | | | |
|---|---|---|---|
| GB | 2 191 030 | A | 12/1987 |
| GB | 2 222 712 | A | 3/1990 |
| GB | 2 226 436 | A | 6/1990 |
| GB | 2 226 907 | A | 7/1990 |
| GB | 2 231 189 | | 11/1990 |
| GB | 2 282 690 | | 4/1995 |
| GB | 2 322 217 | A | 8/1998 |
| GB | 2 333 880 | A | 9/1998 |
| GB | 2 328 311 | | 2/1999 |
| GB | 2 353 128 | A | 2/2001 |
| GB | 2 383 668 | A | 11/2001 |
| GB | 2 387 703 | | 10/2003 |
| JP | 7118307 | | 6/1995 |
| JP | 20002-320703 | | 11/2002 |
| WO | WO 94 12256 | | 6/1994 |
| WO | WO 95 22811 | | 8/1995 |
| WO | WO 95 30944 | | 11/1995 |
| WO | WO 97 12338 | | 4/1997 |
| WO | WO 97 27568 | | 7/1997 |
| WO | WO 97 32285 | | 9/1997 |
| WO | WO 98 35309 | | 8/1998 |
| WO | WO 98 47115 | | 10/1998 |
| WO | WO 98 51384 | | 11/1998 |
| WO | WO 99 03078 | | 1/1999 |
| WO | WO 99 10849 | | 3/1999 |
| WO | WO 00 12186 | | 3/2000 |
| WO | WO 00 32286 | | 6/2000 |
| WO | WO 00 66235 | | 11/2000 |
| WO | WO 00 76606 | | 12/2000 |
| WO | WO 01 10523 | | 2/2001 |
| WO | WO 01 15055 | | 3/2001 |
| WO | WO 01 15790 | | 3/2001 |
| WO | WO 01 26019 | | 4/2001 |
| WO | WO 03 030066 | | 4/2003 |
| WO | WO 03 075235 | | 9/2003 |
| WO | WO 2004 035161 | | 4/2004 |
| WO | WO 2004 066061 | | 8/2004 |
| WO | WO 2005 027058 | | 3/2005 |
| WO | WO 2005 076193 | | 8/2005 |
| WO | WO 2005 081623 | | 9/2005 |
| WO | WO 2005 083599 | | 9/2005 |
| WO | WO 2005 099425 | | 10/2005 |
| WO | WO 2005 099845 | | 10/2005 |
| WO | WO 2005 106702 | | 11/2005 |
| WO | WO 2005 113093 | | 12/2005 |
| WO | WO 2006 014770 | | 2/2006 |
| WO | WO 2006 014883 | | 2/2006 |
| WO | WO 2006 014990 | | 2/2006 |
| WO | WO 2006 039366 | | 4/2006 |

OTHER PUBLICATIONS

American Bandstand Article written by in Strictly Slots, published in 2002.
American Bandstand Brochure written by Anchor Games, published in 2001.
Aristrocrat Brochure, written by Aristocrat Gaming, published in 2004.
Atronic Systems Progressive Products at G2E, published by Atronic in 2004, printed from ForRelease.com.
Austin Powers in Goldmember™ Advertisement written by IGT, published in 2003.
Bally Slot Machines Eiectro-Mechanicals 1964-1980 Book [In Part], Revised 3rd Edition written by Marshall Fey.
Big Shot™ Advertisement published by Aristocrat Technologies, Inc., pubiished in 2002.
Big Top Keno Advertisement published by Aristocrat Technologies, Inc., published in 2000.
Bingo Game Brochure written by Casino Data System, published in 1998.
Bonus Roulette Brochure written by F. Franco, published prior to Sep. 2003.
Buck's Roulette Brochure written by R. Franco, published prior to Sep. 2003.
Cartoon Jackpots description, printed from www.ballygaming.com/home.asp on Feb. 4, 2005.
Cash Express Advertisements, written by Aristocrat, published in 2002.
Cashing in Article, written by Strictly Slots, published in Aug. 2006.
Chariot's of Fortune Brochure written by R. Franco, published prior to Sep. 2003.
Classic Pot of Gold Brochure written by Ace Coin Equipment Ltd., published prior to Sep. 2003.
Crazy Fruits Article written by Strictly Slots, published in Apr. 2001.
Cyberdyne Gaming Brochure written by Cyberdyne Gaming, published prior to Sep. 11, 2003.
Double Diamond Girls Advertisement, written by A.C, Coin and Slot Services Company, published prior to Sep. 11, 2003.
Double Spin Five Times Pay Advertisement, written by IGT, published prior to 2000.
Double up Poker Game Description written by IGT, available prior to Sep. 2000,.
Elvira® Mistress of the Dark™ Advertisement written by IGT, published in 2002.
Elvis Hits Advertisement written by IGT, published in 1999.
Fast Buck Systems Manual, written by International Game Technology, available to Mirage shift supervisors at least as early as May 30, 1990.
Fortune Cookie Brochure written by IGT, published in 2000.
Full House Brochure written by Anchor Games, published in 2000.
High Low Card Game written by Qeocities.com, printed May 3, 2001.
Holy Smoke Brochure written by Impulse Gaming Ltd., published prior to Sep. 2003.
Honeymooners Advertisement, written by AC Coin & Slot, published in 2002.
Hot Shot Progressive Article, written by Strictly Slots, published in Feb. 2006.
In Between Game Description written by IGT, available prior to Sep. 2000.
Jack and the Beanstalk™ Article written by Strictly Slots, published Jul. 2002.
Jackpot Carnival Hyperlink Advertisement, written by Aristocrat, published prior to 2002.
Jackpot Hotline Advertisement, written by AC Coin and Slot, published prior to Sep. 2003.
Jackpot Hunter Advertisement, written by IGT, available prior to Jan. 2005.
Jewel in the Crown Brochure written by Barcrest, Ltd, published date unknown.
King of the Grill™ Brochure written by AC Coin & Slot, published prior to Sep. 2003.
Lemons, Cherries and Bell-Fruit-Gum written by Richard M. Bueschel, pp. 39-41, 64, 70, 137, 149-150, 195-196 and 251, 1995.
Lemons, Cherries and Bell-Fruit-Gum, pp. 1 to 4 and 304 to 314, written by Bueschel, published in Royal Bell Books in Nov. 1995.
Line-Up Brochure written by AC Coin & Slot, published prior to Sep. 2003.
Little Green Men Jr.™ Advertisement written by AC Coin & Slot, published prior to Sep. 11, 2003.
Little Green Men Jr.™ Article written by Strictly Slots, published in Feb. 2003.
Magic 8 Ball Advertisement written by IGT, published in 2002.
Mikohn Product Catalog, Chapters 1, 2, 6, 7 and 8, written by Mikohn, published in Jan. 1993.
Mikohn Ripley's Believe It or Not Article written by Strictly Slots published in 2001.
Mikohn Supper Controller Manual, Chapters 1 to 3 and 6 to 7, written by Mikohn, published in 1989.
Millioni$er articles, written by Strictly Slots, published in Sep. 2003 and Mar. 2004.
Miss America Brochure written by AC Coin & Slot, published prior to Sep. 11, 2003.

(56) References Cited

OTHER PUBLICATIONS

Mix and Match Advertisement published by AC Coin & Slot, published prior to Sep. 2003.
Mix and Match Article written by Strictly Slots, published in Apr. 2002.
Money Grab Article written by Strictly Slots, published in Apr. 2001.
Money Time advertisement, written by Mikohn Gaming, published in 1999.
Money to Burn Brochure written by WMS Gaming, Inc., published prior to 2001.
Monster Match Advertisement by Strictly Slots, published prior to Sep. 9, 2003.
Monster Match Article, written by Strictly Slots, published in Jan. 2002.
Monte Carlo Advertisement written by Bally Gaming, published prior to Sep. 2002.
M-Slot Series Primary Reel Product description from Lemons, Cherries and Bell-Fruit-Gum, written by Richard M. Bueschel, published in 1995.
On the Money! Article written by Strictly Slots, published in Dec. 2000.
Payout!™ Advertisement written by www.csds.com/Gaming/Products_/g_Payout.htm, printed on Jan. 15, 2001.
Payout!™ Article written by Casino Data Systems, published prior to Sep. 2003.
PEM—Precision Electronic Meter, written by GRIPS Electronic GmbH, printed from website reported as archived on Feb. 20, 1997 (available at http://web.archive.org/web/19970220165753/www.grips.com/pem.htm).
Penguin Pucks article, written by Note in Gaming Marketplace, published prior to 2004.
Pick a Prize Brochure written by Acres Gaming Incorporated, published prior to 2001.
Player Tracking on Slots, written by GRIPS Electronic GmbH, printed from website reported as archived on Feb. 20, 1997 (available at http://web.archive.org/web/19970220165921/www.grips.com/playtrac.htm).
Plinko Showcase Show Down written by International Game Technology, published in 2001.
Power Slotto Brochure published by AC Coin & Slot prior to 2002.
Press Your Luck Brochure published by AC Coin & Slot prior to 2002.
Progressive Jackpot System article, printed from casinomagazine.com.managearticle.asp@c_290&a=518, on Jun. 21, 2004.
ProLINK Progressive Controller User/Reference Manual, written by Casino Data Systems, published in Apr. 1997.
Quick Pick Paytime Brochure written by Acres Gaming Incorporated, published prior to 2001.
R&B™ Brochure published by AC Coin & Slot, published prior to Sep. 2003.
Reel Dice Advertisement written by Gerber & Glass, published in 1936.
Royal Roulette Brochure written by Impulse Gaming Ltd., published prior to Sep. 2003.
Run for Your Money Game Description written by Barcrest, published prior to 2001.
Scarne, Scarne's Encyclopedia of Card Games, 1973, HarperCollins Publishers, Inc., 278-279.
Scarne's New Complete Guide to Gambiing (©1997)—John Scarne.
Silver City Roundup Brochure published by AC Coin & Siot, published prior to Sep. 2003.
Slot Line Progressive Advertisement, written by IGT, published in 1993.
Slot Line Progressive Advertisement, written by IGT, published in 1994.
Slot Line Progressive Advertisement, written by IGT, published in 1995.
Slot Line Progressive Mega Jackpots Advertisement, written by IGT, published in 1997.
Slot Line Temperature Rising Game Description, written by IGT, published in 1998.
Slot Machine Buyer's Handbook, A Consumer's Guide to Slot Machines written by David L. Saul and Daniel R. Mead, published in 1998.
Slot Machines a Pictorial History of the First 100 Years (pp. 216, 242 to 243), 5th edition, written by Marshall Fey, published in 1983-1997.
Sot Machines and Coin-Op Games written by Bill Kurtz, pp, 16, 65, 105 and 111, 1991.
Slot Machines on Parade, 1st edition written by Robert N. Geddes and illustrated by Daniel R. Mead, published in 1980.
Sphinx Brochure written by Atronic Casino Technology, Ltd., published in 1997.
Spin Til You Win Information Sheet written by IGT, published in 1996.
Spin-A-Lot Brochure written by Acres Gaming Incorporated, published prior to 2001.
Super Cherry Advertisement written by IGT in 2001.
Surprize Gaming Machine Advertisement, written by Aristocrat Leisure Industries, Australia, published prior to 2004.
Surprize Software Specification for MV2030—var 01, written by Aristocrat Leisure Industries, Australia, published prior to 2004.
Take Your Pick Article written by Strictly Slots, published in Mar. 2001.
Take Your Pick Brochure and Article written by IGT/Anchor Games, Strictly Slots, published in 1999.
The Killer List of Video Games, Soda Pop Tapper, Bally Midway, 1984, The International Arcade Museum.
Top Dollar Brochure written by IGT, published in 1998.
Wheel & Deal Brochure written by Strictly Slots, published in Dec. 2001.
Wheel of Fortune Advertisement written by IGT, published in 1998.
Wheel Poker Article, written by Strictly Slots, published prior to 2002.
*Wide Area Progressive Link System*, written by GRIPS Electronic GmbH, printed from website reported as archived on Feb. 20, 1997 (available at http://web.archive.org/web/19970220165457/www.grips.com/wap.htm).
Yahtzee Bonus Advertisement written by Mikohn, published in 1999.
Zorro Advertisement, written by Aristocrat, published in 2004.

GAMING SYSTEM AND METHOD WHICH PROVIDES PLAYERS AN OPPORTUNITY TO WIN A PROGRESSIVE AWARD

PRIORITY CLAIM

This application is a continuation of, claims priority to and the benefit of U.S. patent application Ser. No. 11/557,869, filed on Nov. 8, 2006, the entire contents of which is incorporated by reference herein.

COPYRIGHT NOTICE

A portion of the disclosure of this patent document contains or may contain material which is subject to copyright protection. The copyright owner has no objection to the photocopy reproduction by anyone of the patent document or the patent disclosure in exactly the form it appears in the Patent and Trademark Office patent file or records, but otherwise reserves all copyright rights whatsoever.

BACKGROUND

Gaming machines which provide players awards in primary or base games are well known. Gaming machines generally require the player to place or make a wager to activate the primary or base game. In many of these gaming machines, the award is based on the player obtaining a winning symbol or symbol combination and on the amount of the wager (e.g., the higher the wager, the higher the award). Symbols or symbol combinations which are less likely to occur usually provide higher awards.

In such known gaming machines, the amount of the wager made on the base game by the player may vary. For instance, the gaming machine may enable the player to wager a minimum number of credits, such as one credit (e.g., one penny, nickel, dime, quarter or dollar) up to a maximum number of credits, such as five credits. This wager may be made by the player a single time or multiple times in a single play of the primary game. For instance, a slot game may have one or more paylines and the slot game may enable the player to make a wager on each payline in a single play of the primary game. Thus, it is known that a gaming machine, such as a slot game, may enable players to make wagers of substantially different amounts on each play of the primary or base game ranging, for example, from 1 credit up to 125 credits (e.g., 5 credits on each of 25 separate paylines). This is also true for other wagering games, such as video draw poker, where players can wager one or more credits on each hand and where multiple hands can be played simultaneously. Accordingly, it should be appreciated that different players play at substantially different wagering amounts or levels and at substantially different rates of play.

Secondary or bonus games are also known in gaming machines. The secondary or bonus games usually provide an additional award to the player. Secondary or bonus games usually do not require an additional wager by the player to be activated. Secondary or bonus games are generally activated or triggered upon an occurrence of a designated triggering symbol or triggering symbol combination in the primary or base game. For instance, a bonus symbol occurring on the payline on the third reel of a three reel slot machine may trigger the secondary bonus game. Part of the enjoyment and excitement of playing certain gaming machines is the occurrence or triggering of the secondary or bonus game (even before the player knows how much the bonus award will be). In other words, obtaining a bonus event and a bonus award in the bonus event is part of the enjoyment and excitement for players.

Player tracking systems are also known. Player tracking systems enable gaming establishments to recognize the value of customer loyalty through identifying frequent customers and rewarding them for their patronage. The cumulative history of a particular player's gaming activity, which is included in a player profile, enables gaming establishments to target individual players with direct marketing promotions or customized compensation plans. In existing player tracking systems, a player is issued a player identification card which has an encoded player identification number that uniquely identifies the player. Player tracking on gaming devices such as slot machines, is typically accomplished with a card reader mounted to the gaming device. When the player first sits down at a gaming device, the player inserts the card into the card reader. The card reader reads the player identification number off the player tracking card and communicates information through a network to a central computer regarding the player's subsequent gaming activity. Based on this communicated information or data, the gaming establishment classifies each player and provides one or more of such players certain benefits based on these classifications.

One known player tracking system provides an award provided to a designated player if that player's player tracking card is inserted into a gaming device. The award is provided at a randomly determined time and/or a randomly determined amount. The designated player is randomly chosen from all of the carded players (i.e., those players who have inserted their player tracking cards into a gaming device). Although rewarding carded players encourages participation in such a player tracking system, this also may discourage certain players because a player becomes ineligible for the benefit once the player removes their player tracking card from the gaming machine.

Progressive awards associated with gaming machines are also known. In one form, a progressive award is an award amount which includes an initial amount funded by a casino and an additional amount funded through a portion of each wager made on the progressive gaming machine. For example, 0.1% of each wager placed on the primary game of the gaming machine associated with the progressive award may be allocated to the progressive award or progressive award fund or pool. The progressive award grows in value as more players play the gaming machines and more portions of these players' wagers are allocated to the progressive award. When a player obtains a winning symbol or symbol combination associated with the progressive award, the accumulated progressive award is provided to the player. After the progressive award is provided to the player, the amount of the next progressive award is reset to the initial value and a portion of each subsequent wager on a gaming machine associated with a progressive award is allocated to the next progressive award.

A progressive award may be associated with or otherwise dedicated to a single or stand-alone gaming machine. Alternatively, a progressive award may be associated with or otherwise dedicated to multiple gaming machines which each contribute a portion of wagers placed at such gaming machine(s) to the progressive award. The multiple gaming machines may be in the same bank of gaming machines, in the same casino or gaming establishment (usually through a local area network ("LAN")) or in two or more different casinos or gaming establishments (usually through a wide area network ("WAN")). Such progressive awards are played for by one or more gaming devices in the same gaming establishment sometimes called local area progressives ("LAP") and such progressive awards played for by a plurality of gaming devices at a plurality of different gaming establishments are sometimes called wide area progressives ("WAP").

U.S. Pat. No. 6,241,608 B1 entitled "Progressive Wagering System" discloses a linked progressive wagering system specifying a boundary criteria, such as a maximum value or an expiration date and time, for a progressive award prize. If a gaming device has not randomly generated a prize award event when the specified boundary criteria is met, a progressive award prize is forced by the system upon one or more randomly selected participating players.

While such progressive awards are popular amongst players, a number of issues exist with these known progressive award systems. First, only players currently playing gaming devices in the progressive award gaming system are eligible to win the progressive award. Typically, in such systems, the player who places the wager that caused the system to meet the specified criteria (such as time or amount of coin-in) is awarded the progressive award. Thus, if a player stops playing for the progressive award, the player sacrifices their opportunity to win the progressive award and the progressive award may be provided to another player. This may discourage certain players from playing a gaming device if they have a limited amount of time to play.

Additionally, if a player wagers large amounts for a long period of time at a gaming device in a progressive award system, that player contributes to or funds a relatively large portion of the progressive award pool. Certain players may be hesitant to wager such large amounts for a long period of time when those players lose their chance to win the progressive award upon walking away from the gaming device. That is, certain players may be reluctant to contribute or invest large amounts of wagers and time try to win a progressive award that the players have no chance of winning if the players leave the gaming device.

In one instance, certain players leave the gaming devices after realizing that the progressive award has been provided to another player. Such players may walk away from the gaming devices feeling discouraged. Such discouragement can lead to certain players walking away with jackpot fatigue. By walking away, even if the player has spent long periods of time playing for the progressive award, the player sacrifices or forfeits any opportunity to win the progressive award. This may lead to certain players feeling pessimistic about their chances to win the progressive award.

Other players may believe that a significant amount of time and money are required to win the progressive award. This may discourage certain players from playing a gaming device, especially if those players have a limited amount of money to play with or a limited amount of time to play.

There is a continuing need to provide new and different gaming machines and gaming systems as well as new and different ways to provide awards to players including progressive or other bonus awards.

SUMMARY

The present disclosure enables a plurality of players to play for one or more progressive awards, such as accumulated value progressive awards, at gaming machines or gaming devices of a gaming system. In one embodiment, the gaming system enables any player who contributed to an accrual of a designated progressive award to win that progressive award regardless of when those contributions were made. That is, any player who contributed to the accumulated value progressive award is eligible to win that progressive award regardless of whether that player is playing at one of the gaming machines in the gaming system. In another embodiment, the gaming system enables any player who contributed to an accrual of a designated progressive award during a designated time period to win that progressive award. It should be appreciated that the players may include players who are currently playing at one of the gaming machines in the gaming system or players who have played at one of the gaming machines in the gaming system during a designated time period.

In one embodiment, the gaming system has at least two independent and separate triggering events for each progressive award. Upon the occurrence of a first triggering event, such as a player triggering event, the gaming system designates a winning player for the progressive award. That is, the gaming system selects one of the players who has played one of the gaming devices in the gaming system and contributed to the progressive award. Upon the occurrence of a second, subsequently occurring triggering event, such as an award triggering event, the gaming system determines the value of the progressive award to be provided to the designated player. That is, independent of which player is designated as the winning player, the system determines the value of the progressive award to be provided to the designated player. Thus, the gaming system independently and separately determines which player will win a progressive award (i.e., selected as a winning player) and when that progressive award will be provided to the winning player (i.e., the amount of the progressive award). Such a configuration enables players who leave the gaming machine and/or the gaming system to remain eligible to win the progressive award. This configuration also enables players currently playing and players not currently playing one of the gaming devices in the gaming system to be eligible to win the progressive award, provided that these players have contributed to the progressive award, such as during a designated time period. For example, if a player leaves a gaming device in the progressive gaming system without having won a progressive award, the player may not be aware that they were selected as the winning player. Such players may be selected while playing one of the gaming devices of the gaming system and sent notification of the amount of the progressive award won subsequent to leaving the gaming device.

In a first embodiment, the progressive award is an accumulated value progressive award or $N^{th}$ coin progressive award provided to the designated winning player based on the occurrence of the player triggering event and the award triggering event. In one such embodiment, the player triggering event occurs when the accumulated value progressive award increments to a first progressive hit value or player threshold value. Upon the occurrence of the player triggering event, the central controller selects a currently playing player who contributed to the accumulated value progressive award and designates that player as the winning player. In this embodiment, the award triggering event occurs subsequent to the player triggering event. The award triggering event occurs when the accumulated value progressive award increments to a second progressive hit value or award threshold value. Upon the occurrence of the award triggering event, the amount of the designated progressive award is determined and the designated progressive award is provided to the designated winning player. The gaming system utilizes a designated coin-in value to select when the accumulated progressive award will increment to the player threshold value and the award threshold value. Such a coin-in value is determined by using the wager value and the percentage of each wager applied to the accumulated value progressive award. For example, the player threshold may be set at the $500,000^{th}$ coin and the award threshold may be set at the $1,000,000^{th}$ coin. In this example, the designated progressive award accumulates based on a predetermined percentage (such as 1%) of coin-in or wagered amounts. For a contribution rate of 1%, one penny or $0.01 will be contributed to the progressive award for each $1.00 wagered. Based on a contribution rate of 1%, wherein a winning player is thus designated when the progressive award reaches $5,000 (e.g., if each coin is one dollar and the designated progressive award starts at a default value equal to $0). Accordingly, the accumulated progressive award is thus provided to a winning player when the progressive award reaches $10,000 (e.g., if each coin is one dollar and the designated progressive award starts at a default value equal to $0). In other alternative embodiments, the designated coin-in value is randomly determined, predetermined or otherwise determined in another suitable manner. It should be appreciated that the progressive award may start at any suitable start up value, which may be funded by a portion of coin-in or by one or more departments of the gaming establishment.

In a second embodiment, the award triggering event occurs prior to the player triggering event. In such an embodiment, the accumulated value progressive award is stored or escrowed when the award triggering event occurs. Upon the occurrence of the player triggering event, a winning player is designated and the stored or escrowed progressive award is provided to the designated winning player. That is, if the accumulated value progressive award reaches the award threshold value prior to reaching the player threshold value, the progressive award is stored or escrowed. Accordingly, when the gaming system designates a winning player, the winning player is provided with the stored progressive award.

In one embodiment, as players play for a designated progressive award, a portion of each player's wager contributes to an accumulated value of the designated progressive award. In one embodiment, each player who contributed to the designated progressive award is eligible to win that designated progressive award, even if that player is no longer playing for that designated progressive award or playing at a gaming machine in the gaming system. In one embodiment, the gaming system stores the contributions from players who are not currently playing (or any eligible players). In this embodiment, when a winning player is selected, the gaming system selects the winning player from a group including all of the players who contributed to the progressive award. In one embodiment, the eligibility of each player for the designated progressive award is tracked by a suitable player tracking system, such as in conjunction with a player tracking card system or in another suitable manner. In one embodiment, each eligible player gains eligibility into one, a plurality or each progressive award level of a multi-level progressive ("MLP") configuration.

In one embodiment, the gaming system independently and separately determines when a progressive award will be hit and stores or escrows the hit progressive award until a winning player is determined. When the gaming system designates a winning player, the winning player is provided with the stored progressive award. This enables players who contribute to one, more or each progressive award to be eligible for one of those progressive awards.

In one embodiment, the gaming system independently and separately determines when a winning player will be selected and stores or escrows the winning player until a progressive award is hit. When the gaming system determines that the progressive award is hit, the gaming system provides the hit progressive award to the stored winning player. This enables players who contribute to one, more or each progressive award while currently playing at one of the gaming devices in the gaming system and to be eligible for one of those progressive awards (e.g., regardless of whether the player is playing or has stopped playing at one of the gaming machines in the gaming system).

In one embodiment, the gaming system disclosed herein causes a suitable notification to be sent to the players of the gaming devices. This notification informs the players which player was selected as the winning player and/or the amount of the progressive award. In one embodiment, the notification includes information relating to a stored progressive award or information relating to the winning player. In this embodiment, the notification may be provided in the form of a message sent to the gaming device at which the winning player is playing. If the winning player is not playing in the gaming system or cannot be located at another gaming device, the notification may be sent in any other manner, such as through telephone, e-mail or any other suitable medium. In one embodiment, a electronic kiosk at the gaming establishment may be used to provide such notification and enable the winning players to claim the progressive award. Alternatively, such notification is displayed on a website accessible to the players which provides instructions for the winning player to claim the award at the gaming establishment. In one instance, the winning player must return to the gaming establishment to claim the award.

In one embodiment, the gaming device or gaming system selects the winning player during an accumulation period for the designated progressive award (i.e., before the progressive award is hit or awarded). For example, if the designated progressive award is set to hit after 1,750,000 coins (e.g., $17,500 if each coin is one dollar and the designated progressive award starts at a default value equal to $0) are accumulated, player who are playing at one of the gaming machines in the gaming system when the $1,750,000^{th}$ coin is wagered are eligible to win the designated progressive award. The gaming system tracks or groups the coin-in of these players and enables these players to be eligible to win the designated progressive award. In an alternate embodiment, players who contribute any of coins 1 to 1,750,000 are eligible to win the designated progressive award. For example, a winning player for a designated progressive award may be selected after the $1,700,000^{th}$ coin is inserted and the designated progressive award accumulates to $17,000 (i.e., based on a contribution rate of 1% if each coin is one dollar and the designated progressive award starts at a default value equal to $0). When the designated progressive award accumulates to $17,500 (i.e., after 1,750,000 coins based on a contribution rate of 1% if each coin is one dollar and the designated progressive award starts at a default value equal to $0), the progressive award is awarded to the winning player as described above. Since the winning player is independently determined before the designated progressive award is hit or determined to be provided to a player, the winning player may be sent a notification or announcement after the designated progressive award reaches $17,500. Such a configuration reduces jackpot fatigue in one sense because a value of the designated progressive award when the winning player is designated (i.e., $17,000) has no bearing on the value of the progressive award provided to the winning player (i.e., $17,500).

Alternatively, in another embodiment, the gaming system selects the winning player after one or more progressive awards have been hit or awarded. In this case, the gaming system disclosed herein stores the designated progressive award until the gaming system designates a player to win that designated progressive award. In one embodiment, the designated progressive award reaches the award threshold at a predetermined time prior to a designation of the winning player. In such embodiments, the gaming system causes a notification to be sent to players of gaming machines in the gaming system that the designated progressive award may be won shortly, e.g., in the next 15 minutes. For example, such notification may be displayed on an overhead display to inform players and non-players of the gaming devices of the progressive award. This generates great excitement and anticipation amongst the current players and enables non-players to begin playing one of the gaming devices for the progressive award.

Accordingly, an advantage of the gaming system disclosed herein is to include a plurality of progressive awards wherein the gaming device provides a player an opportunity to win one, more or each progressive award that the player has contributed to, regardless of whether that player is currently playing one of the gaming machines in the gaming system. Such a configuration provides increased excitement and enjoyment for players because the players are provided a chance to win a plurality of progressive awards regardless of whether those players continue or stop playing at one of the gaming machines in the gaming system and regardless of whether one or more progressive awards are hit. This configuration also encourages players to join a loyalty program or player tracking system.

Additional features and advantages are described in, and will be apparent from, the following Detailed Description and the figures.

DETAILED DESCRIPTION

The present disclosure may be implemented in various configurations for gaming machines or gaming devices, including but not limited to: (1) a dedicated gaming machine or gaming device, wherein the computerized instructions for controlling any games (which are provided by the gaming machine or gaming device) are provided with the gaming machine or gaming device prior to delivery to a gaming establishment; and (2) a changeable gaming machine or gaming device, where the computerized instructions for controlling any games (which are provided by the gaming machine or gaming device) are downloadable to the gaming machine or gaming device through a data network when the gaming machine or gaming device is in a gaming establishment. In one embodiment, the computerized instructions for controlling any games are executed by a central server, central controller or remote host. In such a "thin client" embodiment, the central server remotely controls any games (or other suitable interfaces) and the gaming device is utilized to display such games (or suitable interfaces) and receive one or more inputs or commands from a player. In another embodiment, the computerized instructions for controlling any games are communicated from the central server, central controller or remote host to a gaming device local processor and memory devices. In such a "thick client" embodiment, the gaming device local processor executes the communicated computerized instructions to control any games (or other suitable interfaces) provided to a player.

In one embodiment, one or more gaming devices in a gaming system may be thin client gaming devices and one or more gaming devices in the gaming system may be thick client gaming devices. In another embodiment, certain functions of the gaming device are implemented in a thin client environment and certain other functions of the gaming device are implemented in a thick client environment. In one such embodiment, computerized instructions for controlling any primary games are communicated from the central server to the gaming device in a thick client configuration and computerized instructions for controlling any secondary games or bonus functions are executed by a central server in a thin client configuration.

Figure 1A:
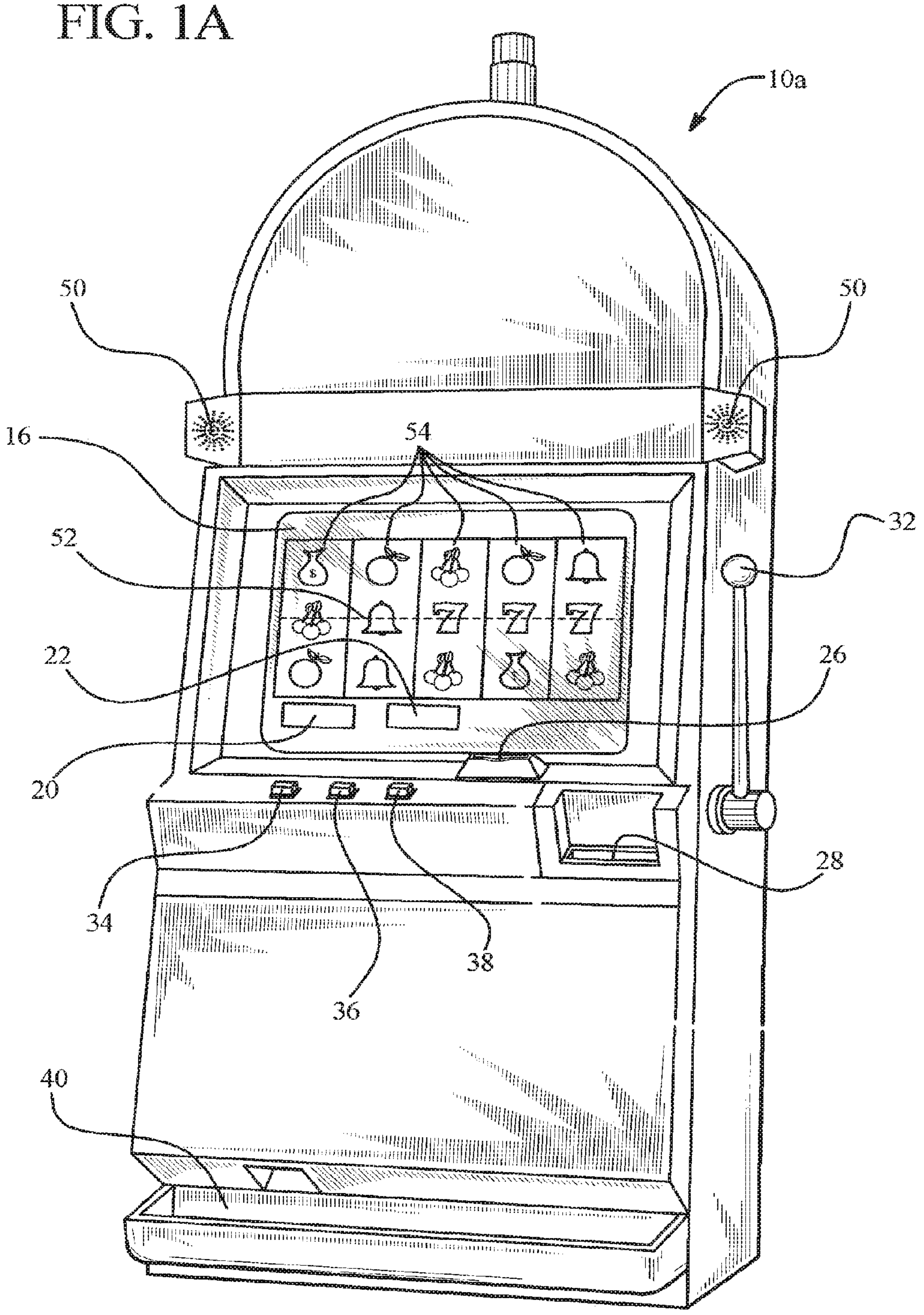
FIG. 1A is a front-side perspective view of one embodiment of the gaming device disclosed herein.
Figure 1B:
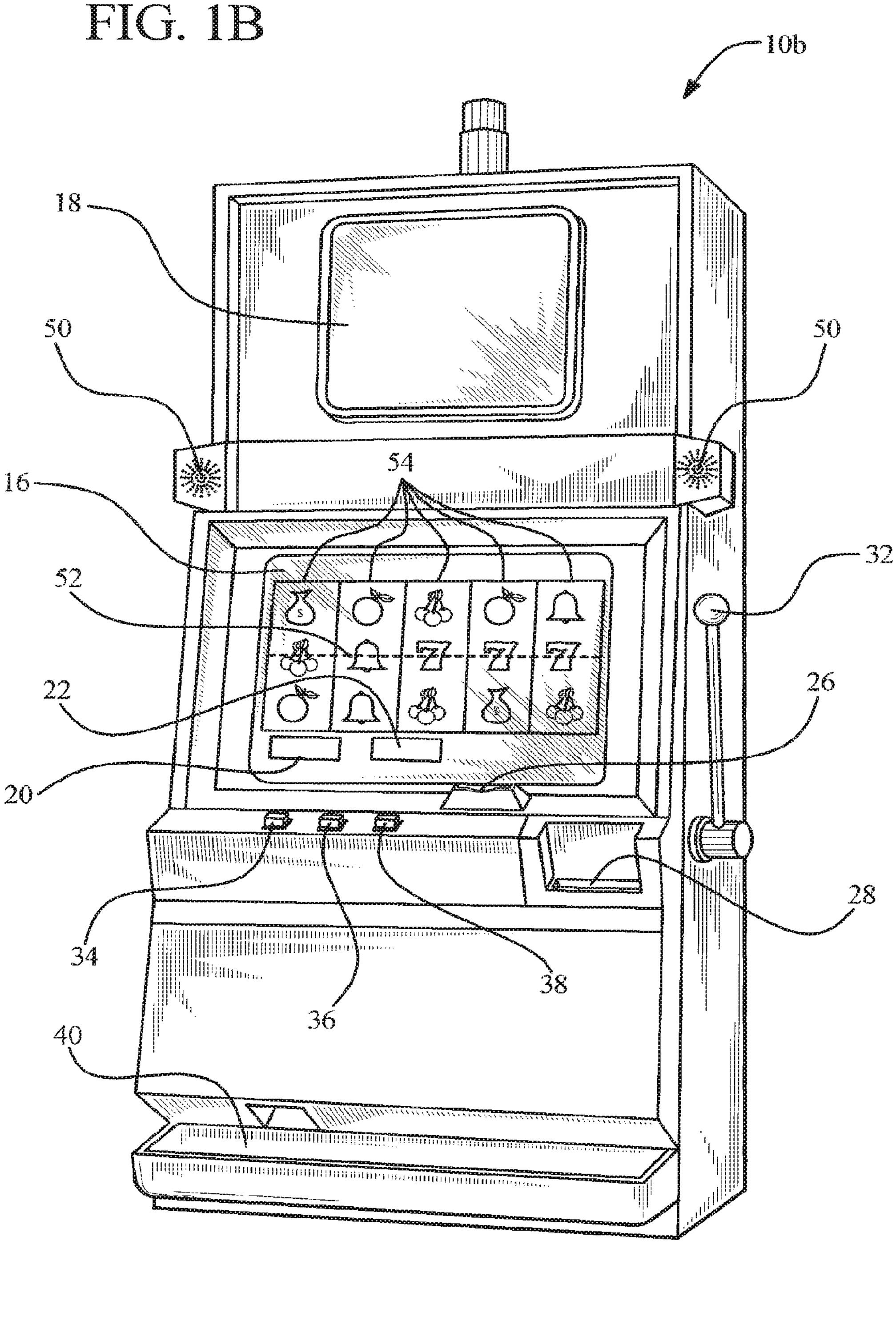
FIG. 1B is a front-side perspective view of another embodiment of the gaming device disclosed herein.

Referring now to the drawings, two example alternative embodiments of the gaming device of the gaming system disclosed herein are illustrated in FIGS. 1A and 1B as gaming device 10*a* and gaming device 10*b*, respectively. Gaming device 108 and/or gaming device 10*b* are generally referred to herein as gaming device 10.

In the embodiments illustrated in FIGS. 1A and 1B, gaming device 10 has a support structure, housing or cabinet which provides support for a plurality of displays, inputs, controls and other features of a conventional gaming machine. It is configured so that a player can operate it while standing or sitting. The gaming device may be positioned on a base or stand or can be configured as a pub-style table-top game (not shown) which a player can operate preferably while sitting. As illustrated by the different configurations shown in FIGS. 1A and 1B, the gaming device may have varying cabinet and display configurations.

Figure 2A:
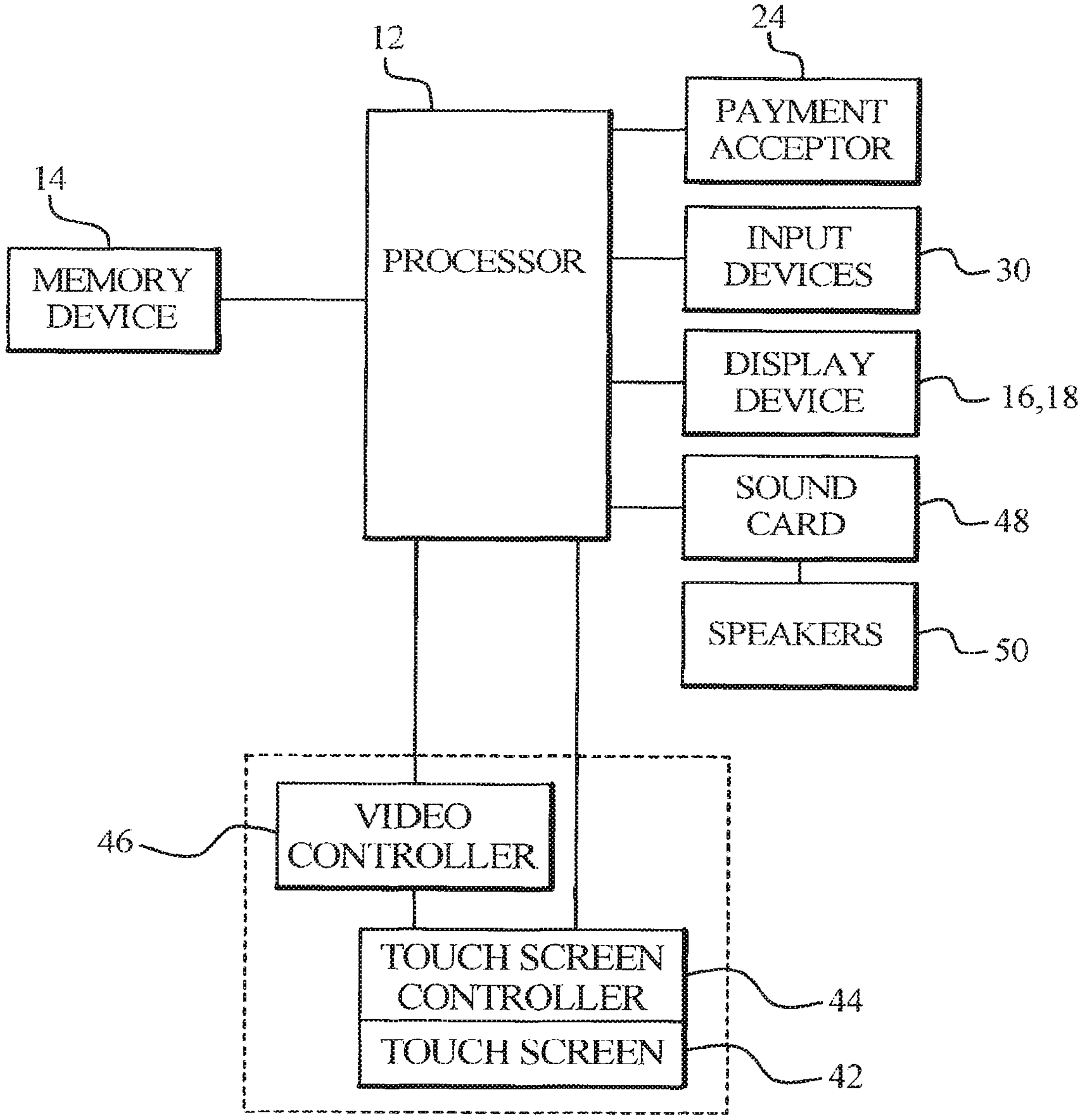
FIG. 2A is a schematic block diagram of the electronic configuration of one embodiment of the gaming device disclosed herein.

In one embodiment, as illustrated in FIG. 2A, the gaming device preferably includes at least one processor 12, such as a microprocessor, a microcontroller-based platform, a suitable integrated circuit or one or more application-specific integrated circuits (ASIC's). The processor is in communication with or operable to access or to exchange signals with at least one data storage or memory device 14. In one embodiment, the processor and the memory device reside within the cabinet of the gaming device. The memory device stores program code and instructions, executable by the processor, to control the gaming device. The memory device also stores other data such as image data, event data, player input data, random or pseudo-random number generators, pay-table data or information and applicable game rules that relate to the play of the gaming device. In one embodiment, the memory device includes random access memory (RAM), which can include non-volatile RAM (NVRAM), magnetic RAM (MRAM), ferroelectric RAM (FeRAM) and other forms as commonly understood in the gaming industry. In one embodiment, the memory device includes read only memory (ROM). In one embodiment, the memory device includes flash memory and/or EEPROM (electrically erasable programmable read only memory). Any other suitable magnetic, optical and/or semiconductor memory may operate in conjunction with the gaming device disclosed herein.

In one embodiment, part or all of the program code and/or operating data described above can be stored in a detachable or removable memory device, including, but not limited to, a suitable cartridge, disk, CD ROM, DVD or USB memory device. In other embodiments, part or all of the program code and/or operating data described above can be downloaded to the memory device through a suitable network.

In one embodiment, an operator or a player can use such a removable memory device in a desktop computer, a laptop personal computer, a personal digital assistant (FDA), portable computing device, or other computerized platform to implement the present disclosure. In one embodiment, the gaming device or gaming machine disclosed herein is operable over a wireless network, such as part of a wireless gaming system. In this embodiment, the gaming machine may be a hand held device, a mobile device or any other suitable wireless device that enables a player to play any suitable game at a variety of different locations. It should be appreciated that a gaming device or gaming machine as disclosed herein may be a device that has obtained approval from a regulatory gaming commission or a device that has not obtained approval from a regulatory gaming commission. It should be appreciated that the processor and memory device may be collectively referred to herein as a "computer" or "controller."

In one embodiment, as discussed in more detail below, the gaming device randomly generates awards and/or other game outcomes based on probability data. In one such embodiment, this random determination is provided through utilization of a random number generator (RNG), such as a true random number generator, a pseudo random number generator or other suitable randomization process. In one embodiment, each award or other game outcome is associated with a probability and the gaming device generates the award or other game outcome to be provided to the player based on the associated probabilities. In this embodiment, since the gaming device generates outcomes randomly or based upon one or more probability calculations, there is no certainty that the gaming device will ever provide the player with any specific award or other game outcome.

In another embodiment, as discussed in more detail below, the gaming device employs a predetermined or finite set or pool of awards or other game outcomes. In this embodiment, as each award or other game outcome is provided to the player, the gaming device flags or removes the provided award or other game outcome from the predetermined set or pool. Once flagged or removed from the set or pool, the specific provided award or other game outcome from that specific pool cannot be provided to the player again. This type of gaming device provides players with all of the available awards or other game outcomes over the course of the play cycle and guarantees the amount of actual wins and losses.

In another embodiment, as discussed below, upon a player initiating game play at the gaming device, the gaming device enrolls in a bingo game. In this embodiment, a bingo server calls the bingo balls that result in a specific bingo game outcome. The resultant game outcome is communicated to the individual gaming device to be provided to a player. In one embodiment, this bingo outcome is displayed to the player as a bingo game and/or in any form in accordance with the present disclosure.

In one embodiment, as illustrated in FIG. 2A, the gaming device includes one or more display devices controlled by the processor. The display devices are preferably connected to or mounted to the cabinet of the gaming device. The embodiment shown in FIG. 1A includes a central display device 16 which displays a primary game. This display device may also display any suitable secondary game associated with the primary game as well as information relating to the primary or secondary game. The alternative embodiment shown in FIG. 1B includes a central display device 16 and an upper display device 18. The upper display device may display the primary game, any suitable secondary game associated or not associated with the primary game and/or information relating to the primary or secondary game. These display devices may also serve as digital glass operable to advertise games or other aspects of the gaming establishment. As seen in FIGS. 1A and 1B, in one embodiment, the gaming device includes a credit display 20 which displays a player's current number of credits, cash, account balance or the equivalent. In one embodiment, gaming device includes a bet display 22 which displays a player's amount wagered.

In another embodiment, at least one display device may be a mobile display device, such as a FDA or tablet PC, that enables play of at least a portion of the primary or secondary game at a location remote from the gaming device.

The display devices may include, without limitation, a monitor, a television display, a plasma display, a liquid crystal display (LCD) a display based on light emitting diodes (LED), a display based on a plurality of organic light-emitting diodes (OLEDs), a display based on polymer light-emitting diodes (PLEDs), a display based on a plurality of surface-conduction electron-emitters (SEDs), a display including a projected and/or reflected image or any other suitable electronic device or display mechanism. In one embodiment, as described in more detail below, the display device includes a touch-screen with an associated touch-screen controller. The display devices may be of any suitable size and configuration, such as a square, a rectangle or an elongated rectangle.

The display devices of the gaming device are configured to display at least one and preferably a plurality of game or other suitable images, symbols and indicia such as any visual representation or exhibition of the movement of objects such as mechanical, virtual or video reels and wheels, dynamic lighting, video images, images of people, characters, places, things and faces of cards, and the like.

In one alternative embodiment, the symbols, images and indicia displayed on or of the display device may be in mechanical form. That is, the display device may include any electromechanical device, such as one or more mechanical objects, such as one or more rotatable wheels, reels or dice, configured to display at least one or a plurality of game or other suitable images, symbols or indicia.

As illustrated in FIG. 2A, in one embodiment, the gaming device includes at least one payment acceptor 24 in communication with the processor. As seen in FIGS. 1A and 1B, the payment acceptor may include a coin slot 26 and a payment, note or bill acceptor 28, where the player inserts money, coins or tokens. The player can place coins in the coin slot or paper money, a ticket or voucher into the payment, note or bill acceptor. In other embodiments, devices such as readers or validators for credit cards, debit cards or credit slips may accept payment. In one embodiment, a player may insert an identification card into a card reader of the gaming device. In one embodiment, the identification card is a smart card having a programmed microchip or a magnetic strip coded with a player's identification, credit totals (or related data) and other relevant information. In another embodiment, a player may carry a portable device, such as a cell phone, a radio frequency identification tag or any other suitable wireless device, which communicates a player's identification, credit totals (or related data) and other relevant information to the gaming device. In one embodiment, money may be transferred to a gaming device through electronic funds transfer. When a player funds the gaming device, the processor determines the amount of funds entered and displays the corresponding amount on the credit or other suitable display as described above.

As seen in FIGS. 1A, 1B and 2A, in one embodiment the gaming device includes at least one and preferably a plurality of input devices 30 in communication with the processor. The input devices can include any suitable device which enables the player to produce an input signal which is received by the processor. In one embodiment, after appropriate funding of the gaming device, the input device is a game activation device, such as a pull arm 32 or a play button 34 which is used by the player to start any primary game or sequence of events in the gaming device. The play button can be any suitable play activator such as a bet one button, a max bet button or a repeat the bet button. In one embodiment, upon appropriate funding, the gaming device begins the game play automatically. In another embodiment, upon the player engaging one of the play buttons, the gaming device automatically activates game play.

In one embodiment, as shown in FIGS. 1A and 1B, one input device is a bet one button 36. The player places a bet by pushing the bet one button. The player can increase the bet by one credit each time the player pushes the bet one button. When the player pushes the bet one button, the number of credits shown in the credit display preferably decreases by one, and the number of credits shown in the bet display preferably increases by one. In another embodiment, one input device is a bet max button (not shown) which enables the player to bet the maximum wager permitted for a game of the gaming device.

In one embodiment, one input device is a cash out button 38. The player may push the cash out button and cash out to receive a cash payment or other suitable form of payment corresponding to the number of remaining credits. In one embodiment, when the player cashes out, the player receives the coins or tokens in a coin payout tray 40. In one embodiment, when the player cashes out, the player may receive other payout mechanisms such as tickets or credit slips redeemable by a cashier (or other suitable redemption system) or funding to the player's electronically recordable identification card.

In one embodiment, as mentioned above and seen in FIG. 2A, one input device is a touch-screen 42 coupled with a touch-screen controller 44, or some other touch-sensitive display overlay to allow for player interaction with the images on the display. The touch-screen and the touch-screen controller are connected to a video controller 46. A player can make decisions and input signals into the gaming device by touching the touch-screen at the appropriate places. One such input device is a conventional touch-screen button panel.

The gaming device may further include a plurality of communication ports for enabling communication of the processor with external peripherals, such as external video sources, expansion buses, game or other displays, an SCSI port or a key pad.

In one embodiment, as seen in FIG. 2A, the gaming device includes a sound generating device controlled by one or more sounds cards 48 which function in conjunction with the processor. In one embodiment, the sound generating device includes at least one and preferably a plurality of speakers 50 or other sound generating hardware and/or software for generating sounds, such as playing music for the primary and/or secondary game or for other modes of the gaming device, such as an attract mode. In one embodiment, the gaming device provides dynamic sounds coupled with attractive multimedia images displayed on one or more of the display devices to provide an audio-visual representation or to otherwise display full-motion video with sound to attract players to the gaming device. During idle periods, the gaming device may display a sequence of audio and/or visual attraction messages to attract potential players to the gaming device. The videos may also be customized for or to provide any appropriate information.

In one embodiment, the gaming machine may include a sensor, such as a camera in communication with the processor (and possibly controlled by the processor) that is selectively positioned to acquire an image of a player actively using the gaming device and/or the surrounding area of the gaming device. In one embodiment, the camera may be configured to selectively acquire still or moving (e.g., video) images and may be configured to acquire the images in either an analog, digital or other suitable format. The display devices may be configured to display the image acquired by the camera as well as display the visible manifestation of the game in split screen or picture-in-picture fashion. For example, the camera may acquire an image of the player and the processor may incorporate that image into the primary and/or secondary game as a game image, symbol or indicia.

Gaming device 10 can incorporate any suitable wagering primary or base game. The gaming machine or device may include some or all of the features of conventional gaming machines or devices. The primary or base game may comprise any suitable reel-type game, card game, cascading or falling symbol game, number game or other game of chance susceptible to representation in an electronic or electromechanical form, which in one embodiment produces a random outcome based on probability data at the time of or after placement of a wager. That is, different primary wagering games, such as video poker games, video blackjack games, video keno, video bingo or any other suitable primary or base game may be implemented.

In one embodiment, as illustrated in FIGS. 1A and 1B, a base or primary game may be a slot game with one or more paylines 52. The paylines may be horizontal, vertical, circular, diagonal, angled or any combination thereof. In this embodiment, the gaming device includes at least one and preferably a plurality of reels 54, such as three to five reels 54, in either electromechanical form with mechanical rotating reels or video form with simulated reels and movement thereof. In one embodiment, an electromechanical slot machine includes a plurality of adjacent, rotatable reels which may be combined and operably coupled with an electronic display of any suitable type. In another embodiment, if the reels 54 are in video form, one or more of the display devices, as described above, display the plurality of simulated video reels 54. Each reel 54 displays a plurality of indicia or symbols, such as bells, hearts, fruits, numbers, letters, bars or other images which preferably correspond to a theme associated with the gaming device. In another embodiment, one or more reels are independent reels or unisymbol reels. In this embodiment, each independent or unisymbol reel generates and displays one symbol to the player. In one embodiment, the gaming device awards prizes after the reels of the primary game stop spinning if specified types and/or configurations of indicia or symbols occur on an active payline or otherwise occur in a winning pattern, occur on the requisite number of adjacent reels and/or occur in a scatter pay arrangement.

In an alternative embodiment, rather than determining any outcome to provide to the player by analyzing the symbols generated on any wagered upon paylines as described above, the gaming device determines any outcome to provide to the player based on the number of associated symbols which are generated in active symbol positions on the requisite number of adjacent reels (i.e., not on paylines passing through any displayed winning symbol combinations). In this embodiment, if a winning symbol combination is generated on the reels, the gaming device provides the player one award for that occurrence of the generated winning symbol combination. For example, if one winning symbol combination is generated on the reels, the gaming device will provide a single award to the player for that winning symbol combination (i.e., not based on the number of paylines that would have passed through that winning symbol combination). It should be appreciated that because a gaming device with wagering on ways to win provides the player one award for a single occurrence of a winning symbol combination and a gaming device with paylines may provide the player more than one award for the same occurrence of a single winning symbol combination (i.e., if a plurality of paylines each pass through the same winning symbol combination), it is possible to provide a player at a ways to win gaming device with more ways to win for an equivalent bet or wager on a traditional slot gaming device with paylines.

In one embodiment, the total number of ways to win is determined by multiplying the number of symbols generated in active symbol positions on a first reel by the number of symbols generated in active symbol positions on a second reel by the number of symbols generated in active symbol positions on a third reel and so on for each reel of the gaming device with at least one symbol generated in an active symbol position. For example, a three reel gaming device with three symbols generated in active symbol positions on each reel includes 27 ways to win (i.e., 3 symbols on the first reel×3 symbols on the second reel×3 symbols on the third reel). A four reel gaming device with three symbols generated in active symbol positions on each reel includes 81 ways to win (i.e., 3 symbols on the first reel×3 symbols on the second reel×3 symbols on the third reel×3 symbols on the fourth reel). A five reel gaming device with three symbols generated in active symbol positions on each reel includes 243 ways to win (i.e., 3 symbols on the first reel×3 symbols on the second reel×3 symbols on the third reel×3 symbols on the fourth reel×3 symbols on the fifth reel). It should be appreciated that modifying the number of generated symbols by either modifying the number of reels or modifying the number of symbols generated in active symbol positions by one or more of the reels, modifies the number of ways to win.

In another embodiment, the gaming device enables a player to wager on and thus activate symbol positions. In one such embodiment, the symbol positions are on the reels. In this embodiment, if based on the player's wager, a reel is activated, then each of the symbol positions of that reel will be activated and each of the active symbol positions will be part of one or more of the ways to win. In one embodiment, if based on the player's wager, a reel is not activated, then a designated number of default symbol positions, such as a single symbol position of the middle row of the reel, will be activated and the default symbol position(s) will be part of one or more of the ways to win. This type of gaming machine enables a player to wager on one, more or each of the reels and the processor of the gaming device uses the number of wagered on reels to determine the active symbol positions and the number of possible ways to win. In alternative embodiments, (1) no symbols are displayed as generated at any of the inactive symbol positions, or (2) any symbols generated at any inactive symbol positions may be displayed to the player but suitably shaded or otherwise designated as inactive.

In one embodiment wherein a player wagers on one or more reels, a player's wager of one credit may activate each of the three symbol positions on a first reel, wherein one default symbol position is activated on each of the remaining four reels. In this example, as described above, the gaming device provides the player three ways to win (i.e., 3 symbols on the first reel×1 symbol on the second reel×1 symbol on the third reel×1 symbol on the fourth reel×1 symbol on the fifth reel). In another example, a player's wager of nine credits may activate each of the three symbol positions on a first reel, each of the three symbol positions on a second reel and each of the three symbol positions on a third reel wherein one default symbol position is activated on each of the remaining two reels. In this example, as described above, the gaming device provides the player twenty-seven ways to win i.e., 3 symbols on the first reel×3 symbols on the second reel×3 symbols on the third reel×1 symbol on the fourth reel×1 symbol on the fifth reel).

In one embodiment, to determine any award(S) to provide to the player based on the generated symbols, the gaming device individually determines if a symbol generated in an active symbol position on a first reel forms part of a winning symbol combination with or is otherwise suitably related to a symbol generated in an active symbol position on a second reel. In this embodiment, the gaming device classifies each pair of symbols which form part of a winning symbol combination (i.e., each pair of related symbols) as a string of related symbols. For example, if active symbol positions include a first cherry symbol generated in the top row of a first reel and a second cherry symbol generated in the bottom row of a second reel, the gaming device classifies the two cherry symbols as a string of related symbols because the two cherry symbols form part of a winning symbol combination.

After determining if any strings of related symbols are formed between the symbols on the first reel and the symbols on the second reel, the gaming device determines if any of the symbols from the next adjacent reel should be added to any of the formed strings of related symbols. In this embodiment, for a first of the classified strings of related symbols, the gaming device determines if any of the symbols generated by the next adjacent reel form part of a winning symbol combination or are otherwise related to the symbols of the first string of related symbols. If the gaming device determines that a symbol generated on the next adjacent reel is related to the symbols of the first string of related symbols, that symbol is subsequently added to the first string of related symbols. For example, if the first string of related symbols is the string of related cherry symbols and a related cherry symbol is generated in the middle row of the third reel, the gaming device adds the related cherry symbol generated on the third reel to the previously classified string of cherry symbols.

On the other hand, if the gaming device determines that no symbols generated on the next adjacent reel are related to the symbols of the first string of related symbols, the gaming device marks or flags such string of related symbols as complete. For example, if the first string of related symbols is the string of related cherry symbols and none of the symbols of the third reel are related to the cherry symbols of the previously classified string of cherry symbols, the gaming device marks or flags the string of cherry symbols as complete.

After either adding a related symbol to the first string of related symbols or marking the first string of related symbols as complete, the gaming device proceeds as described above for each of the remaining classified strings of related symbols which were previously classified or formed from related symbols on the first and second reels.

After analyzing each of the remaining strings of related symbols, the gaming device determines, for each remaining pending or incomplete string of related symbols, if any of the symbols from the next adjacent reel, if any, should be added to any of the previously classified strings of related symbols. This process continues until either each string of related symbols is complete or there are no more adjacent reels of symbols to analyze. In this embodiment, where there are no more adjacent reels of symbols to analyze, the gaming device marks each of the remaining pending strings of related symbols as complete.

When each of the strings of related symbols is marked complete, the gaming device compares each of the strings of related symbols to an appropriate paytable and provides the player any award associated with each of the completed strings of symbols. It should be appreciated that the player is provided one award, if any, for each string of related symbols generated in active symbol positions (i.e., as opposed to being based on how many paylines that would have passed through each of the strings of related symbols in active symbol positions).

In one embodiment, a base or primary game may be a poker game wherein the gaming device enables the player to play a conventional game of video draw poker and initially deals five cards all face up from a virtual deck of fifty-two card deck. Cards may be dealt as in a traditional game of cards or in the case of the gaming device, may also include that the cards are randomly selected from a predetermined number of cards. If the player wishes to draw, the player selects the cards to hold via one or more input device, such as pressing related hold buttons or via the touch screen. The player then presses the deal button and the unwanted or discarded cards are removed from the display and the gaming machine deals the replacement cards from the remaining cards in the deck. This results in a final five-card hand. The gaming device compares the final five-card hand to a payout table which utilizes conventional poker hand rankings to determine the winning hands. The gaming device provides the player with an award based on a winning hand and the credits the player wagered.

In another embodiment, the base or primary game may be a multi-hand version of video poker. In this embodiment, the gaming device deals the player at least two hands of cards. In one such embodiment, the cards are the same cards. In one embodiment each hand of cards is associated with its own deck of cards. The player chooses the cards to hold in a primary hand. The held cards in the primary hand are also held in the other hands of cards. The remaining non-held cards are removed from each hand displayed and for each hand replacement cards are randomly dealt into that hand. Since the replacement cards are randomly dealt independently for each hand, the replacement cards for each hand will usually be different. The poker hand rankings are then determined hand by hand and awards are provided to the player.

In one embodiment, a base or primary game may be a keno game wherein the gaming device displays a plurality of selectable indicia or numbers on at least one of the display devices. In this embodiment, the player selects at least one or a plurality of the selectable indicia or numbers via an input device such as the touch screen. The gaming device then displays a series of drawn numbers to determine an amount of matches, if any, between the player's selected numbers and the gaming device's drawn numbers. The player is provided an award based on the amount of matches, if any, based on the amount of determined matches.

In one embodiment, in addition to winning credits or other awards in a base or primary game, the gaming device may also give players the opportunity to win credits in a bonus or secondary game or bonus or secondary round. The bonus or secondary game enables the player to obtain a prize or payout in addition to the prize or payout, if any, obtained from the base or primary game. In general, a bonus or secondary game produces a significantly higher level of player excitement than the base or primary game because it provides a greater expectation of winning than the base or primary game and is accompanied with more attractive or unusual features than the base or primary game. In one embodiment, the bonus or secondary game may be any type of suitable game, either similar to or completely different from the base or primary game.

In one embodiment, the triggering event or qualifying condition may be a selected outcome in the primary game or a particular arrangement of one or more indicia on a display device in the primary game, such as the number seven appearing on three adjacent reels along a payline in the primary slot game embodiment seen in FIGS. 1A and 1B. In other embodiments, the triggering event or qualifying condition may be by exceeding a certain amount of game play (such as number of games, number of credits, amount of time), or reaching a specified number of points earned during game play.

In another embodiment, the gaming device processor 12 or central server 56 randomly provides the player one or more plays of one or more secondary games. In one such embodiment, the gaming device does not provide any apparent reasons to the player for qualifying to play a secondary or bonus game. In this embodiment, qualifying for a bonus game is not triggered by an event in or based specifically on any of the plays of any primary game. That is, the gaming device may simply qualify a player to play a secondary game without any explanation or alternatively with simple explanations. In another embodiment, the gaming device (or central server) qualifies a player for a secondary game at least partially based on a game triggered or symbol triggered event, such as at least partially based on the play of a primary game.

In one embodiment, the gaming device includes a program which will automatically begin a bonus round after the player has achieved a triggering event or qualifying condition in the base or primary game. In another embodiment, after a player has qualified for a bonus game, the player may subsequently enhance his/her bonus game participation through continued play on the base or primary game. Thus, for each bonus qualifying event, such as a bonus symbol, that the player obtains, a given number of bonus game wagering points or credits may be accumulated in a "bonus meter" programmed to accrue the bonus wagering credits or entries toward eventual participation in a bonus game. The occurrence of multiple such bonus qualifying events in the primary game may result in an arithmetic or exponential increase in the number of bonus wagering credits awarded. In one embodiment, the player may redeem extra bonus wagering credits during the bonus game to extend play of the bonus game.

In one embodiment, no separate entry fee or buy in for a bonus game need be employed. That is, a player may not purchase an entry into a bonus game, rather they must win or earn entry through play of the primary game thus, encouraging play of the primary game. In another embodiment, qualification of the bonus or secondary game is accomplished through a simple "buy in" by the player, for example, if the player has been unsuccessful at qualifying through other specified activities. In another embodiment, the player must make a separate side-wager on the bonus game or wager a designated amount in the primary game to qualify for the secondary game. In this embodiment, the secondary game triggering event must occur and the side-wager (or designated primary game wager amount) must have been placed to trigger the secondary game.

Figure 2B:
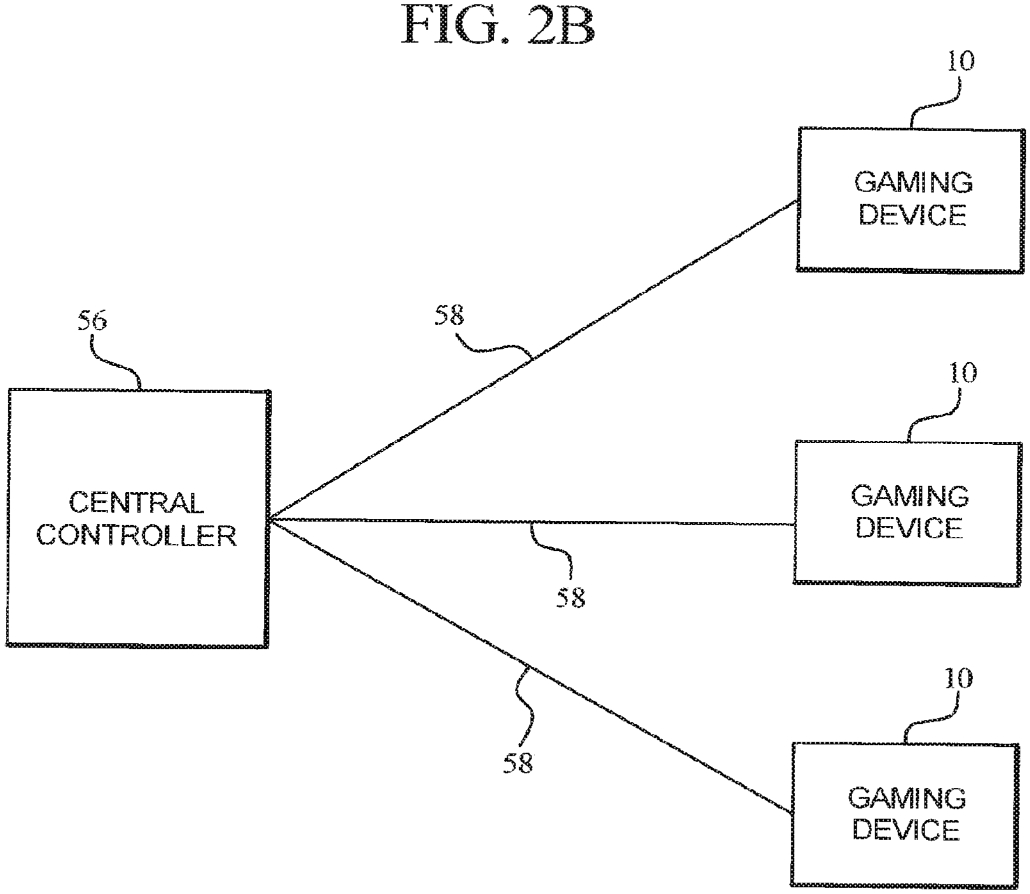
FIG. 2B is a schematic block diagram illustrating a plurality of gaming terminals in communication with a central controller.

In one embodiment, as illustrated in FIG. 2B, one or more of the gaming devices 10 are in communication with each other and/or at least one central server, central controller or remote host 56 through a data network or remote communication link 58. In this embodiment, the central server, central controller or remote host is any suitable server or computing device which includes at least one processor and at least one memory or storage device. In different such embodiments, the central server is a progressive controller or a processor of one of the gaming devices in the gaming system. In these embodiments, the processor of each gaming device is designed to transmit and receive events, messages, commands or any other suitable data or signal between the individual gaming device and the central server. The gaming device processor is operable to execute such communicated events, messages or commands in conjunction with the operation of the gaming device. Moreover, the processor of the central server is designed to transmit and receive events, messages, commands or any other suitable data or signal between the central server and each of the individual gaming devices. The central server processor is operable to execute such communicated events, messages or commands in conjunction with the operation of the central server. It should be appreciated that one, more or each of the functions of the central controller as disclosed herein may be performed by one or more gaming device processors. It should be further appreciated that one, more or each of the functions of one or more gaming device processors as disclosed herein may be performed by the central controller.

In one embodiment, the game outcome provided to the player is determined by a central server or controller and provided to the player at the gaming device. In this embodiment, each of a plurality of such gaming devices are in communication with the central server or controller. Upon a player initiating game play at one of the gaming devices, the initiated gaming device communicates a game outcome request to the central server or controller.

In one embodiment, the central server or controller receives the game outcome request and randomly generates a game outcome for the primary game based on probability data. In another embodiment, the central server or controller randomly generates a game outcome for the secondary game based on probability data. In another embodiment, the central server or controller randomly generates a game outcome for both the primary game and the secondary game based on probability data. In this embodiment, the central server or controller is capable of storing and utilizing program code or other data similar to the processor and memory device of the gaming device.

In an alternative embodiment, the central server or controller maintains one or more predetermined pools or sets of predetermined game outcomes. In this embodiment, the central server or controller receives the game outcome request and independently selects a predetermined game outcome from a set or pool of game outcomes. The central server or controller flags or marks the selected game outcome as used. Once a game outcome is flagged as used, it is prevented from further selection from the set or pool and cannot be selected by the central controller or server upon another wager. The provided game outcome can include a primary game outcome, a secondary game outcome, primary and secondary game outcomes, or a series of game outcomes such as free games.

The central server or controller communicates the generated or selected game outcome to the initiated gaming device. The gaming device receives the generated or selected game outcome and provides the game outcome to the player. In an alternative embodiment, how the generated or selected game outcome is to be presented or displayed to the player, such as a reel symbol combination of a slot machine or a hand of cards dealt in a card game, is also determined by the central server or controller and communicated to the initiated gaming device to be presented or displayed to the player. Central production or control can assist a gaming establishment or other entity in maintaining appropriate records, controlling gaming, reducing and preventing cheating or electronic or other errors, reducing or eliminating win-loss volatility and the like.

In another embodiment, a predetermined game outcome value is determined for each of a plurality of linked or networked gaming devices based on the results of a bingo or keno game. In this embodiment, each individual gaming device utilizes one or more bingo or keno games to determine the predetermined game outcome value provided to the player for the interactive game played at that gaming device. In one embodiment, the bingo or keno game is displayed to the player. In another embodiment, the bingo or keno game is not displayed to the player, but the results of the bingo or keno game determine the predetermined game outcome value for the primary or secondary game.

In the various bingo embodiments, as each gaming device is enrolled in the bingo game, such as upon an appropriate wager or engaging an input device, the enrolled gaming device is provided or associated with a different bingo card. Each bingo card consists of a matrix or array of elements, wherein each element is designated with a separate indicia, such as a number. It should be appreciated that each different bingo card includes a different combination of elements. For example, if four bingo cards are provided to four enrolled gaming devices, the same element may be present on all four of the bingo cards while another element may solely be present on one of the bingo cards.

In operation of these embodiments, upon providing or associating a different bingo card to each of a plurality of enrolled gaming devices, the central controller randomly selects or draws, one at a time, a plurality of the elements. As each element is selected, a determination is made for each gaming device as to whether the selected element is present on the bingo card provided to that enrolled gaming device. This determination can be made by the central controller, the gaming device, a combination of the two, or in any other suitable manner. If the selected element is present on the bingo card provided to that enrolled gaming device, that selected element on the provided bingo card is marked or flagged. This process of selecting elements and marking any selected elements on the provided bingo cards continues until one or more predetermined patterns are marked on one or more of the provided bingo cards. It should be appreciated that in one embodiment, the gaming device requires the player to engage a daub button (not shown) to initiate the process of the gaming device marking or flagging any selected elements.

After one or more predetermined patterns are marked on one or more of the provided bingo cards, a game outcome is determined for each of the enrolled gaming devices based, at least in part, on the selected elements on the provided bingo cards. As described above, the game outcome determined for each gaming device enrolled in the bingo game is utilized by that gaming device to determine the predetermined game outcome provided to the player. For example, a first gaming device to have selected elements marked in a predetermined pattern is provided a first outcome of win $10 which will be provided to a first player regardless of how the first player plays in a first game and a second gaming device to have selected elements marked in a different predetermined pattern is provided a second outcome of win $2 which will be provided to a second player regardless of how the second player plays a second game. It should be appreciated that as the process of marking selected elements continues until one or more predetermined patterns are marked, this embodiment ensures that at least one bingo card will win the bingo game and thus at least one enrolled gaming device will provide a predetermined winning game outcome to a player. It should be appreciated that other suitable methods for selecting or determining one or more predetermined game outcomes may be employed.

In one example of the above-described embodiment, the predetermined game outcome may be based on a supplemental award in addition to any award provided for winning the bingo game as described above. In this embodiment, if one or more elements are marked in supplemental patterns within a designated number of drawn elements, a supplemental or intermittent award or value associated with the marked supplemental pattern is provided to the player as part of the predetermined game outcome. For example, if the four corners of a bingo card are marked within the first twenty selected elements, a supplemental award of $10 is provided to the player as part of the predetermined game outcome. It should be appreciated that in this embodiment, the player of a gaming device may be provided a supplemental or intermittent award regardless of if the enrolled gaming device's provided bingo card wins or does not win the bingo game as described above.

In another embodiment, one or more of the gaming devices are in communication with a central server or controller for monitoring purposes only. That is, each individual gaming device randomly generates the game outcomes to be provided to the player and the central server or controller monitors the activities and events occurring on the plurality of gaming devices. In one embodiment, the gaming network includes a real-time or on-line accounting and gaming information system operably coupled to the central server or controller. The accounting and gaming information system of this embodiment includes a player database for storing player profiles, a player tracking module for tracking players and a credit system for providing automated casino transactions.

In one embodiment, the gaming device disclosed herein is associated with or otherwise integrated with one or more player tracking systems. In this embodiment, the gaming device and/or player tracking system tracks any players gaming activity at the gaming device. In one such embodiment, the gaming device and/or associated player tracking system timely tracks when a player inserts their playing tracking card to begin a gaming session and also timely tracks when a player removes their player tracking card when concluding play for that gaming session. In another embodiment, rather than requiring a player to insert a player tracking card, the gaming device utilizes one or more portable devices carried by a player, such as a cell phone, a radio frequency identification tag or any other suitable wireless device to track when a player begins and ends a gaming session. In another embodiment, the gaming device utilizes any suitable biometric technology or ticket technology to track when a player begins and ends a gaming session.

During one or more gaming sessions, the gaming device and/or player tracking system tracks any suitable information, such as any amounts wagered, average wager amounts and/or the time these wagers are placed. In different embodiments, for one or more players, the player tracking system includes the player's account number, the player's card number, the player's first name, the player's surname, the player's preferred name, the player's player tracking ranking, any promotion status associated with the player's player tracking card, the player's address, the player's birthday, the player's anniversary, the player's recent gaming sessions, or any other suitable data.

In one embodiment, a plurality of the gaming devices are capable of being connected together through a data network. In one embodiment, the data network is a local area network (LAN), in which one or more of the gaming devices are substantially proximate to each other and an on-site central server or controller as in, for example, a gaming establishment or a portion of a gaming establishment. In another embodiment, the data network is a wide area network (WAN) in which one or more of the gaming devices are in communication with at least one off-site central server or controller. In this embodiment, the plurality of gaming devices may be located in a different part of the gaming establishment or within a different gaming establishment than the off-site central server or controller. Thus, the WAN may include an off-site central server or controller and an off-site gaming device located within gaming establishments in the same geographic area, such as a city or state. The WAN gaming system may be substantially identical to the LAN gaming system described above, although the number of gaming devices in each system may vary relative to each other.

In another embodiment, the data network is an internet or intranet. In this embodiment, the operation of the gaming device can be viewed at the gaming device with at least one internet browser. In this embodiment, operation of the gaming device and accumulation of credits may be accomplished with only a connection to the central server or controller (the internet/intranet server) through a conventional phone or other data transmission line, digital subscriber line (DSL). T-1 line, coaxial cable, fiber optic cable, or other suitable connection. In this embodiment, players may access an internet game page from any location where an internet connection and computer, or other internet facilitator is available. The expansion in the number of computers and number and speed of internet connections in recent years increases opportunities for players to play from an ever-increasing number of remote sites. It should be appreciated that enhanced bandwidth of digital wireless communications may render such technology suitable for some or all communications, particularly if such communications are encrypted. Higher data transmission speeds may be useful for enhancing the sophistication and response of the display and interaction with the player.

As mentioned above, in one embodiment, the present disclosure may be employed in a server based gaming system. In one such embodiment, as described above, one or more gaming devices are in communication with a central server or controller. The central server or controller may be any suitable server or computing device which includes at least one processor and a memory or storage device. In alternative embodiments, the central server is a progressive controller or another gaming machine in the gaming system. In one embodiment, the memory device of the central server stores different game programs and instructions, executable by a gaming device processor, to control the gaming device. Each executable game program represents a different game or type of game which may be played on one or more of the gaming devices in the gaming system. Such different games may include the same or substantially the same game play with different pay tables. In different embodiments, the executable game program is for a primary game, a secondary game or both. In another embodiment, the game program may be executable as a secondary game to be played simultaneous with the play of a primary game (which may be downloaded to or fixed on the gaming device) or vice versa.

In this embodiment, each gaming device at least includes one or more display devices and/or one or more input devices for interaction with a player. A local processor, such as the above-described gaming device processor or a processor of a local server, is operable with the display device(s) and/or the input device(s) of one or more of the gaming devices.

In operation, the central controller is operable to communicate one or more of the stored game programs to at least one local processor. In different embodiments, the stored game programs are communicated or delivered by embedding the communicated game program in a device or a component (e.g., a microchip to be inserted in a gaming device), writing the game program on a disc or other media, downloading or streaming the game program over a dedicated data network, internet or a telephone line. After the stored game programs are communicated from the central server, the local processor executes the communicated program to facilitate play of the communicated program by a player through the display device(s) and/or input device(s) of the gaming device. That is, when a game program is communicated to a local processor, the local processor changes the game or type of game played at the gaming device.

In another embodiment, a plurality of players at a plurality of linked gaming devices in a gaming system participate in a group gaming environment. In one embodiment, a plurality of players at a plurality of linked gaming devices work in conjunction with one another, such as playing together as a team or group, to win one or more awards. In one such embodiment, any award won by the group is shared, either equally or based on any suitable criteria, amongst the different players of the group. In another embodiment, a plurality of players at a plurality of linked gaming devices compete against one another for one or more awards. In one such embodiment, a plurality of players at a plurality of linked gaming devices participate in a gaming tournament for one or more awards. In another embodiment, a plurality of players at a plurality of linked gaming devices play for one or more awards wherein an outcome generated by one gaming device affects the outcomes generated by one or more linked gaming devices.

Progressive Awards

In one embodiment, one or more of the gaming devices disclosed herein are in communication with or linked to a central server or controller to form a gaming system. In one such embodiment, the gaming system includes a plurality of linked gaming machines wherein one of the gaming machines functions as the central server or controller. In one embodiment, one, more or each of the progressive awards are maintained by the central controller of the gaming system. In one such embodiment, the central controller enables a player at any gaming device in the gaming system to contribute coin-in or a portion of each wager to one or more of the progressive awards maintained by the central controller. In this embodiment, the winning player and the amount of the progressive award are based, at least in part, on the player's contribution. That is, the gaming system selects a winning player independently from the amount of the progressive award provided to the winning player.

In one embodiment, a master host site computer is coupled to a plurality of the central servers at a variety of mutually remote gaming sites for providing a multi-site linked progressive automated gaming system. In one embodiment, a master host site computer may serve gaming devices distributed throughout a number of properties at different geographical locations including, for example, different locations within a city or different cities within a state. In one embodiment, the master host site computer is maintained for the overall operation and control of the system. In this embodiment, a master host site computer oversees all or part of the progressive gaming system and is the master for computing all or part of the progressive jackpots. All participating gaming sites report to, and receive information from, the master host site computer. Each central server computer is responsible for all data communication between the gaming device hardware and software and the master host site computer.

In one embodiment, one or more of the progressive awards start at different levels such as $10, $100. $1000 and $10,000 and increment or increase until provided to a player. The progressive awards accumulate based on a small percentage (such as 1%) of coin-in or wagered amounts in a conventional manner. In one embodiment, the percentage that goes to each progressive award is equal (such as 1% to each of four progressive awards). At this accrual rate, player wagers totaling $100,000 are required for the progressive to reach $1000 (e.g., if each coin is one dollar and the start up value of the progressive award is $0). For example, based on an accrual or contribution rate of 1%, a player who wagers $10,000 at one of the gaming machines contributes or funds $100 to the progressive award and a player who wagers $5,000 at one of the gaming machines contributes or funds $500 to the progressive award. At least a fraction of this amount may be funded by the casino by using a starting value higher than zero to make the progressive awards attractive even after they are reset. In other embodiments, two or more of the progressive awards may be funded by different percentages. In these embodiments, the central server and/or individual gaming device processor continues to increase the progressive levels until a progressive award is provided to a player (upon the occurrence of a progressive award triggering event), at which point the progressive is reset and another progressive award starts incrementing from the appropriate default progressive award level. In another embodiment, two or more of the progressive awards may be funded at different temporal rates. In this embodiment, the different progressive awards are incremented or funded in different increments of time wherein until the progressive hits, a set amount is added to the progressive at each determined time increment. In another embodiment, two or more of the progressive awards may each be incremented or funded based on different incrementing factors or incriminators. In this embodiment, a first of the progressive awards may increment each time a first incrementing factor occurs and a second of the progressive awards may increment each time a second incrementing factor occurs, wherein the first incrementing factor and the second incrementing factor are different. Examples of incrementing factors could be a symbol-driven trigger in the base game, the occurrence of one or more events in a bonus game, the player betting a maximum amount, a percentage of possible gaming machines being actively played or in active status, or any other suitable method for defining an incriminator.

In one embodiment, one or more of the progressive awards are each funded via a side bet or side wager. In this embodiment, a player must place or wager a side bet to be eligible to win the progressive award associated with the side bet. In one embodiment, the player must place the maximum bet and the side bet to be eligible to win one of the progressive awards. In another embodiment, if the player places or wagers the required side bet, the player may wager at any credit amount on any payline (i.e., the player need not place the maximum bet and the side bet to be eligible to win one of the progressive awards). In one such embodiment, the greater the player's wager (in addition to the placed side bet), the greater the odds or probability that the player will win one of the progressive awards. It should be appreciated that one or more of the progressive awards may each be funded, at least in part, based on the wagers placed on the primary games of the gaming machines in the gaming system, via a gaming establishment or via any suitable manner.

In another embodiment, one or more of the progressive awards are partially funded via a side-bet or side-wager which the player may make (and which may be tracked via a side-bet meter). In one embodiment, one or more of the progressive awards are funded with only side-bets or side-wagers placed. In another embodiment, one or more of the progressive awards are funded based on player's wagers as described above as well as any side-bets or side-wagers placed.

In one alternative embodiment, a minimum wager level is required for a gaming machine or a player to qualify to be selected to obtain one of the progressive awards. In one embodiment, this minimum wager level is the maximum wager level for the primary game in the gaming machine. In another embodiment, this minimum wager level is placing a wager on all available paylines in a slot primary game or alternatively placing a wager on all available poker hands in a multi-hand poker primary game. In another embodiment, no minimum wager level is required for a gaming machine or a player to qualify to be selected to obtain one of the progressive awards.

In another embodiment, one or more progressive awards are funded, at least partially, via an amount provided by one or more marketing and/or advertising departments, such as a casino's marketing department. In this embodiment, when a progressive award increments to the amount of money provided by the marketing or advertising department (or any other designated amount), the progressive award is triggered and provided to one or more players.

In one embodiment, a plurality of gaming machines at one or more gaming sites are networked to the central server in a progressive configuration, wherein a portion of each wager placed is allocated to one or more progressive awards. As described below in greater detail, this progressive configuration enables the gaming system to provide one or more players with an opportunity to win a progressive award. In one embodiment, the progressive awards are associated with the gaming machines in the gaming system which each contribute portions of the progressive awards. In one such embodiment, as players of the gaming machines play for one or more of the progressive awards, a portion of each player's wager contributes to an accumulated value of a designated progressive award.

In one embodiment, each player who contributed to the designated progressive award is eligible to win that designated progressive award regardless of whether the player is playing for that designated progressive award (e.g., the player switched gaming machines with different progressive awards) or has stopped playing at one of the gaming machines in the gaming system (e.g., the player left the casino or gaming establishment). It should be appreciated that the players currently playing at one of the gaming machines in the gaming system when the designated progressive award hits (i.e., is triggered) or players who have played at one of the gaming machines in the gaming system during a designated time period may be eligible to win the designated progressive award. For example, a progressive award valued at $10,000 may be maintained by the gaming system and provided to one or more designated players. Player A plays at one of the gaming machines in the gaming system and contributes $20.00 coin-in to the progressive award before stopping play. Player B plays at another of the gaming machines in the gaming system and contributes $5.00 coin-in to the progressive award. In contrast to Player A, Player B continues to play for the progressive award. In this example, both Player A and Player B are eligible to win the progressive award value of $10,000. Thus, if a player changes games, changes gaming machines or even quits playing one of the gaming machines in the gaming system, the player does not sacrifice their opportunity to win one or more of the progressive awards.

In one embodiment, the amount of coin-in contributed to a designated progressive award by a given player is limited or capped. For example, a player is only able to contribute a predetermined maximum amount or percentage of a designated progressive award. In one embodiment, after a player contributes the maximum amount or percentage, any coin-in contributed to the designated progressive award is applied to a different designated progressive award (e.g., a designated progressive award at a subsequent time). Such a configuration enables a player to qualify for a plurality of progressive awards at the same time (e.g., during a single gaming session). It should be appreciated that once a player contributes the maximum amount or percentage to a designated progressive award, that player may qualify for one or more available progressive awards or one or more future progressive awards with subsequent coin-in.

In one embodiment, other eligibility conditions are used to determine whether the player qualifies for one of the progressive awards. The eligibility conditions may supplement or replace the condition that the player currently plays at one of the gaming machines in the gaming system. As described above, a side-bet and a minimum wager level constitute different eligibility conditions for a player to qualify to be selected to obtain one of the progressive awards. In various embodiments, different eligibility conditions are predetermined, randomly determined, determined or weighted based on the player's wager, determined or weighted based on the status of one or more players (such as determined through a player tracking system), determined based on time, or determined based on any other suitable parameter or function.

In one embodiment, the gaming system keeps track of and stores the coin-in of all players who have contributed to each designated progressive award. In such an embodiment, the gaming system selects the winning player based on the stored coin-in of current and past players. That is, the gaming system selects a winning player from a group including each player who contributed to the progressive award regardless of when that contribution was made. This encourages players to join a loyalty program and/or a player tracking system to remain eligible to win one or more progressive awards regardless of whether the players are currently playing at one of the gaming machines in the gaming system. In another embodiment, the winning player is selected based on the coin-in for players currently playing at one of the gaming machines in the gaming system. In one embodiment, the winning player is selected based on the coin-in for current players in addition to the coin in for past players. For example, all current players and a number of past players (e.g., which may be selected based on player status as determined through a suitable player tracking system or some other suitable factor) may be eligible to be selected as the winning player.

In another embodiment, a player's eligibility is determined based, at least in part, on whether the player is registered with or identified by the gaming system. Players may register with the gaming system at any of the gaming machines in the gaming system or at a remote location, such as at an electronic kiosk. Players enter identifying information, such as the player's name and address, and a suitable security code, such as a PIN number, via an input device associated with the gaming machine or kiosk. Such identifying information may be stored in a module of a suitable player tracking system or may be stored in any suitable storage device in communication with the central controller. In one embodiment, once a player is registered and identified, that player becomes eligible to win one of the progressive awards in the gaming system.

In one embodiment, the gaming system provides a game, such as a primary game, on each of a plurality of gaming machines. The games are operable upon a wager placed by at least one player. The central controller maintains a progressive award, such as an accumulated value progressive award. The central controller determines which player to provide with the progressive award. This determination is based on a first value of the progressive award. For example, the central controller determines the winning player of the progressive award when the progressive award reaches a first predetermined or qualifying value, such as a player threshold value. In this embodiment, the central controller subsequently determines when to provide the progressive award to the winning player regardless of whether the winning player is currently playing one of the games of one of the gaming machines. This determination is based on a second value of the progressive award. For example, the central controller determines to provide the designated progressive award to the winning player when the progressive award reaches a second predetermined or qualifying value, such as an award threshold value. In one embodiment, the central controller also provides a secondary or bonus award to the player responsible for (i.e., who placed the wager that caused) the progressive award reaching the player threshold value and/or the award threshold value).

In one embodiment, the determination of when to provide the designated progressive award occurs prior to the determination of which player to provide with the designated progressive award. In this embodiment, the designated progressive award is stored or escrowed until the winning player is determined. In one embodiment, the gaming system displays information regarding the stored or escrowed progressive award. This information may be displayed in audio, text or video format to inform the player that the stored or escrowed progressive award will be provided shortly, the amount of the progressive award available to be won by the player or any other suitable information.

In one embodiment, each progressive award of the gaming system is an accumulated value progressive award funded by a designated portion of each wager from each player. In this embodiment, if a first triggering event (i.e., a player triggering event) and a second triggering event (i.e., an award triggering event) occur, a designated progressive award is provided to a designated player. The accumulated value progressive award is provided to a winning player designated via the first triggering event (e.g., the generation of a first designated amount of coin-in) when the second, different triggering event (e.g., the generation of a second designated amount of coin-in) occurs. In one embodiment, the second triggering event determines the value of the designated progressive award. That is, the value determined by the second triggering event constitutes the progressive award provided to the designated player determined by the first triggering event.

In one embodiment, a player is designated as the winning player when that player's coin-in causes the accumulated value progressive award to increment to a first predetermined progressive hit value, such as a progressive hit value of $72.60. This first progressive hit value corresponds to the player threshold value. For example, on a $1 wager with 1% allocated to the accumulated value progressive award, the 7,260$^{th}$ coin wagered (if the progressive award starts at a default value equal to $0) results in the accumulated value progressive award reaching the player threshold value (and thus designating that player as the winning player). Accordingly, the player triggering event occurs when the 7,260$^{th}$ coin is wagered.

In one embodiment, the accumulated progressive award is provided to the designated winning player when any player's coin-in causes the accumulated value progressive award to increment to a second predetermined progressive hit value, such as a progressive hit value of $92.13. This second progressive hit value corresponds to the award threshold value. For example, on a $1 wager with 1% allocated to the accumulated value progressive award, the 9,213$^{th}$ coin wagered (if the progressive award starts at a default value equal to $0) results in the accumulated value progressive award reaching the award threshold value (and thus providing the accumulated value progressive award to the designated winning player). Accordingly, the award triggering event occurs when the 9,213$^{th}$ coin is wagered and the designated winning player is provided with the accumulated value progressive award. In this embodiment, the accumulated value progressive award is valued at $92.13.

In different embodiments, the coin-in is determined in any suitable manner, such as by calculating which coin-in will cause the player threshold and award threshold values to change to $72.60 or $92.13, respectively, by monitoring the coin-in versus the progressive award value or by calculating the coin-in value in advance based on the wagers, the player threshold and award threshold values, and the percentage of the wagers allocated to the progressive award. In one embodiment, the central controller keeps track of the play on each gaming machine including at least the amount wagered by the player(s) for each play of the primary game for each gaming machine (i.e., via a total or partial coin-in or wager meter which tracks the total or partial coin-in wagers placed on all of the primary games for all of the gaming machines in the gaming system). In another embodiment, the central controller is operable with a suitable player tracking system to keep track of the play of each player at gaming machines in the gaming system including at least the amount wagered for each player for each play of the primary game.

In one embodiment, once a first progressive award is hit, a second, subsequent progressive award is started. In one such embodiment, after the first progressive award is hit, players playing at one of the gaming machines in the gaming system are more likely to win the second, subsequent progressive award than players who are no longer playing at one of the gaming machines in the gaming system. In another such embodiment, players who contributed coin-in to the first progressive award are more likely to win the second, subsequent progressive award than players who did not contribute coin-in to the first designated progressive award. (i.e., players who started contributing to the second progressive award after the first progressive award was hit or provided). In one embodiment, the central controller counts each coin wagered by each player as 1 coin for the first progressive award. For the second progressive award, the central controller counts each coin wagered by each player who played for the first progressive award as 2 coins and counts each coin wagered by each player who did not play for the first progressive award as 1 coin. In this embodiment, players who contribute more coin-in are more likely to win the designated progressive award than players who contribute less coin-in. Counting each coin as 1 coin, 2 coins or any other suitable number of coins affects each player's chance to win the designated progressive award. Accordingly, players are rewarded or credited for more coin-in when those players play for a number of progressive awards. In one embodiment, the players are required to play for consecutive progressive awards to have their coin-in counted in this manner.

Alternatively, a point system could be used wherein players receive one point for the first progressive award and two points for the second progressive award instead of receiving credit for one coin and two coins, respectively, as described above. In this embodiment, the points correspond to coin-in so that players who have a high number of points have a greater chance to win the progressive award than players who have lower numbers of points.

In one embodiment, the central controller counts each coin wagered by each player as 5 coins for their first progressive award. When those players play for their second progressive award, the central controller counts each coin wagered by those players as 4 coins and counts each coin wagered by each player who is playing for their first progressive award as 5 coins. As described above, players who contribute more coin-in are more likely to win the designated progressive award than players who contribute less coin-in. In this manner, the central controller entices new players to play for the progressive award by increasing those players' chance to win one of the progressive awards (e.g., by weighting their coin-in greater than the coin-in of existing players). Counting each coin as 1 coin, 2 coins or any other suitable number of coins affects each player's chance to win the designated progressive award. In this embodiment, new players are rewarded or credited for more coin-in during when playing for their first progressive award. The central controller may weight the coin-in for any existing players (e.g., those who have played for at least one progressive award) but may do so at a lower level than new players. Accordingly, in this embodiment, new players for a designated progressive award (e.g., those players who have not played for another progressive award) have a greater chance of winning than existing players when their coin-in is counted or weighted in this manner.

In the above embodiments, the central controller weights each coin of coin-in wagered by each player. By weighting the coin-in, the central controller can reward players who play for a number of progressive awards (e.g., by increasing those players' chance to win one of the progressive awards) or the central controller can entice new players to play for the progressive award (e.g., by increasing those players' chance to win one of the progressive awards).

In another embodiment, the gaming system chooses an appropriate coin-in hit value associated with the player threshold value and the award threshold value in any suitable manner. For example, the system randomly chooses the coin-in values, chooses the coin-in values based on a weighted parameter, chooses the coin-in values based upon a determined subset range, or chooses the coin-in values based on any other suitable manner. In one embodiment, the player threshold value and the award threshold value are based on time or some other metric or parameter other than coin-in. For example, the player triggering event occurs at 9:00 pm on a certain day and the award triggering event occurs at 9:15 pm on that day.

Figure 3:
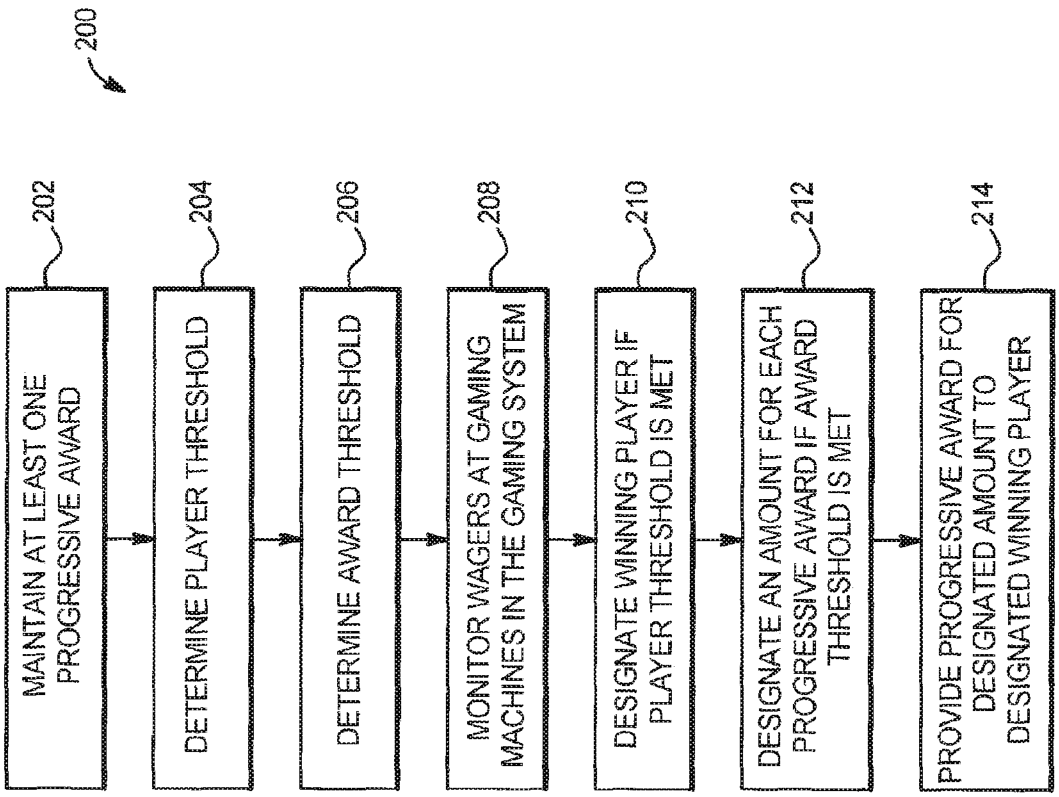
FIG. 3 is a flowchart of one embodiment of the gaming system disclosed herein illustrating an opportunity for one or more players to win a progressive award.

A flowchart of an example process 200 for providing one or more players with an opportunity to win one or more progressive awards is illustrated in FIG. 3. In one embodiment, the process 200 is embodied in one or more software programs storable in one or more memories and executable by one or more processors. Although the process 200 is described with reference to the flowchart illustrated in FIG. 3, it should be appreciated that many other methods of performing the acts associated with process 200 may be used. For example, the order of many of the blocks may be changed, and many of the blocks described may be optional.

The process 200 enables a central controller to independently and separately determine which player will win a progressive award (i.e., a winning player) and when that progressive award will be provided to the winning player. The process 200 begins by maintaining at least one and preferably a plurality of progressive awards as indicated by block 202. The progressive award may be an accumulated value progressive award, which starts at an initial or default value, such as zero. The accumulated value progressive award increments from the initial or default value or is funded from wagers placed on one game or a plurality of different games by a player on one or more gaming machines of the gaming system. The game or games of each gaming machine in the gaming system may be the same games or different games.

In one embodiment, the accumulated value progressive award is associated with a player threshold value and an award threshold value. The accumulated value progressive award accumulates in value or is funded based on the wagers placed on the games of the gaming machines. A portion of each wager contributes to the accrual of the accumulated value progressive award. The player threshold value is a predetermined condition or value established by the central controller at which the accumulated value progressive award reaches a first determined amount or value. The award threshold is a predetermined condition or value established by the central controller at which the accumulated value progressive award reaches a second determined amount or value. These predetermined amounts are randomly selected and based on the coin-in of the gaming machines. As indicated by blocks 204 and 206, respectively, the central controller determines the player threshold and the award threshold independently and separately. In one embodiment, the player threshold and the award threshold values may be different types (e.g., based on coin-in or based on time).

For example, if the player threshold and the award threshold are based on coin-in, the central controller may determine the player threshold to be the 5,000$^{th}$ coin and the award threshold to be the 12,500$^{th}$ coin. If the contribution rate is 1% for each $1.00 wagered, one penny or $0.01 will be contributed to the progressive award for each $1.00 wagered. In this example, the player threshold value is the 5,000$^{th}$ coin wagered or when the accumulated value progressive award reaches a first value of $50.00 (i.e., based on a contribution rate of 1% if each coin is one dollar and the accumulated value progressive award starts at a default value equal to $0) and the award threshold value is the 12,500$^{th}$ coin wagered or when the accumulated value progressive award reaches a second value of $125.00 (i.e., based on a contribution rate of 1% if each coin is one dollar and the accumulated value progressive award starts at a default value equal to $0).

The central controller monitors the wagers at the gaming machines in the gaming system as indicated by block 208. In one embodiment, the central controller keeps track of the play on each gaming machine including at least the amount wagered by the player(s) for each play of the primary game for each gaming machine (i.e., via a total or partial coin-in or wager meter which tracks the total or partial coin-in wagers placed on all of the primary games for all of the gaming machines in the gaming system). It should be appreciated that the player of a gaming machine may change during this tracking and that this tracking can be independent of the specific player playing the gaming machine. In another embodiment, the central controller is operable with a suitable player tracking system to keep track of the play of each player at gaming machines in the gaming system including at least the amount wagered for each player for each play of the primary game. In this embodiment, the player tracking system includes a rules module that is configured to keep track of the amount wagered for each player for each play of the primary game. The central controller communicates with the rules module of the player tracking system to monitor the wagers at the gaming machines in the gaming system.

The central controller compares the amount of coin-in associated with the progressive award from the gaming machines to the player threshold value and the award threshold value determined as indicated by blocks 204 and 206. When the accumulated value progressive award reaches the player threshold value, the central controller designates a winning player as indicated by block 210. That is, the winning player is chosen when the accumulated value progressive award accumulates to a first designated amount of coin-in (i.e., the player threshold value). For example, when a player at one of the gaming machines in the gaming system who wagers the 5,000$^{th}$ coin associated with the accumulated value progressive award, the central controller designates that player as the winning player and determines that the accumulated value progressive award has reached the player threshold value. If the accumulated value progressive award does not reach the player threshold value, the central controller continues to monitor the wagers at the gaming machines in the gaming system as indicated by block 208.

As indicated by block 212, when the accumulated value progressive award reaches or increments to the award threshold value, the central controller designates an amount for each progressive award. When the player threshold value and the award threshold value are met, the central controller provides the progressive award for the designated amount to the designated winning player as indicated by block 214. For example, when a player at one of the gaming machines in the gaming system wagers the 12,500$^{th}$ coin associated with the accumulated value progressive award, the central controller determines that the accumulated value progressive award has reached the award threshold value and designates the accumulated value for the progressive award (e.g., to $125 if each coin is $1, if the progressive award starts at a $0 value and if the contribution rate is 1% of each wager). It should be appreciated that the award threshold value determines, at least in part, the amount of the accumulated value progressive award. Once the accumulated value progressive award reaches the award threshold value, the amount of the accumulated value progressive award is set and a new progressive award begins to accumulate. If the accumulated value progressive award does not reach the player threshold value, the central controller continues to monitor the wagers at the gaming machines in the gaming system as indicated by block 208.

After the accumulated value progressive award reaches the player threshold value and the award threshold value, the central controller provides the progressive award to the winning player. As described in greater detail below, if the winning player has not been designated (i.e., the player threshold value has not been met), the central controller stores the progressive award (or causes the progressive award to be stored) until the winning player is designated. In one embodiment, when the winning player is designated, the central controller causes the accumulated value progressive award to be provided to the winning player when the award threshold value is met. In another embodiment, the central controller causes a notification to be sent to the winning player of the won progressive award and provides the winning player with the won progressive award at a later time, such as in a subsequent gaming session.

It should be appreciated that after the central controller causes the accumulated value progressive award to be provided to the winning player, the central controller resets the progressive award and another progressive award starts incrementing from a second progressive award value or level. In one embodiment, if the award threshold value is less than the player threshold value (i.e., the progressive award is determined to be provided or stored prior to a winning player being designated), the second progressive award is displayed to the player in association with appropriate messaging to inform the players that the accumulated value progressive award has been determined, but not yet provided to a winning player.

Figure 4:
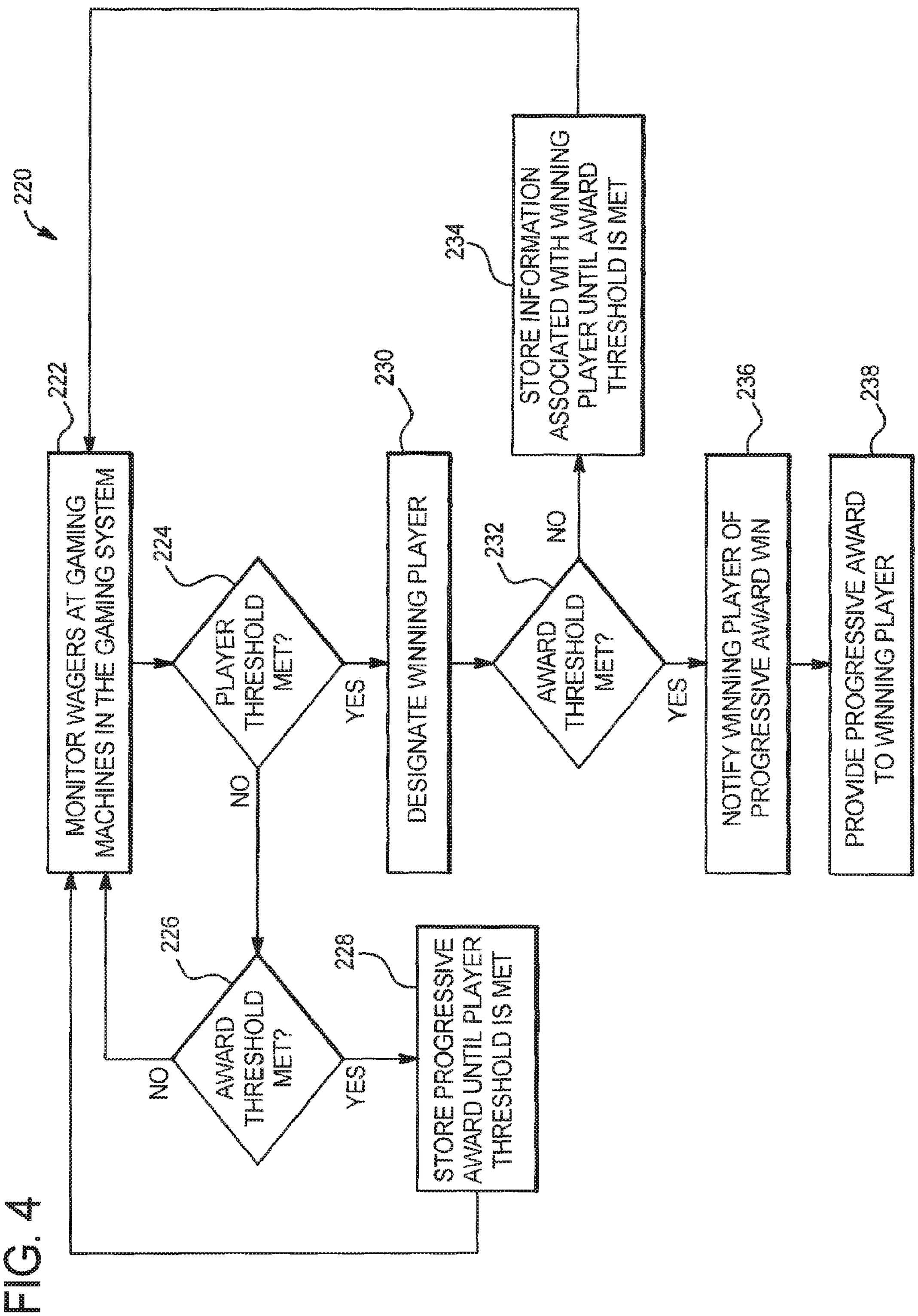
FIG. 4 is a flowchart of one embodiment of the gaming system disclosed herein illustrating an opportunity for one or more players to win a progressive award, wherein the progressive award is stored until a winning player for that progressive award is designated.

FIG. 4 illustrates a flowchart of an example process 220 to store or escrow the progressive award and/or information associated with the winning player. As described above, the central controller monitors the wagers at the gaming machines in the gaming system and determines whether the player threshold value and/or the award threshold value is met. In this embodiment, the central controller determines whether the player threshold value is met as indicated by block 224 prior to determining whether the award threshold value is met as indicated by block 226. It should be appreciated that these determinations may be made sequentially in any order, simultaneously or substantially simultaneously.

As illustrated, if the accumulated value progressive award has not reached the player threshold value, the central controller determines whether the award threshold value is met as indicated by block 226. If the award threshold value is met, i.e., the accumulated value progressive award reaches the award threshold value, the central controller stores the progressive award (or causes the progressive award to be stored) until the player threshold value is met (i.e., the accumulated value progressive award reaches the player threshold value) as indicated by block 228. If the award threshold value is not met, the central controller continues to monitor the wagers at the gaming machines in the gaming system as indicated by block 208.

If the central controller determines that the player threshold value is met, the central controller designates the winning player as indicated by block 230. In one embodiment, the central controller causes no notification of this designation to be sent to the winning player until the award triggering event occurs. Alternatively, the central controller causes a notification to be sent to the winning player of this designation. Such notification may include appropriate messaging sent to the gaming machine at which the winning player is playing, such as any suitable audio, text or visual message.

After the winning player is designated, the central controller determines whether the award threshold value is met as indicated by block 232. If the central controller determines that the award threshold value is not met, the central controller stores information, such as a contact information including a name, a physical address, a phone number and an e-mail address, associated with the winning player, until the award threshold value is met as indicated by block 234. In one embodiment, the central controller in conjunction with a player tracking system (i.e., the rules module) stores the information associated with the designated winning player. In such an embodiment, the player's profile or player tracking card is enabled to access this stored information from the player tracking system. Alternatively, the central controller may request the player to input such information through one of the input devices associated with the gaming machine.

After storing the information associated with the winning player, the central controller continues to monitor the wagers at the gaming machines in the gaming system and determine whether the award threshold value is met as indicated by blocks 208 and 232.

If the central controller determines that the award threshold value is met, the central controller causes a notification to be sent to the winning player of the progressive award win as indicated by block 234. In one embodiment, the winning player is notified of the progressive award win through appropriate messaging sent to the gaming machine at which the winning player is playing. If the player is no longer playing at a gaming machine in the gaming system, the winning player is notified in another manner, such as through contact information in association with the player tracking system or via an internet website. The internet website may be associated with the casino or gaming establishment at which the winning player was playing the gaming machine. Alternatively, the internet website may be associated with the manufacturer of the gaming machine or another suitable third-party. Such notification may include the amount of the progressive award won by the winning player, the date on which the progressive award was won and the casino or gaming establishment where the winning player won the progressive award as well as any promotional information, advertisements or other suitable information. In one embodiment, the notification includes an expiration of the progressive award, such as how many days the progressive award is available to be claimed. It should be appreciated that the expiration may be any suitable length of time and may occur at any suitable time.

As indicated by block 238, the central controller causes the progressive award to be provided to the winning player. As illustrated, the winning player is sent notification of the progressive award win as indicated by block 236 prior to being provided the progressive award. In different embodiments, the winning player is not sent such notification and/or the progressive award is provided to the winning player prior to such notification, if any.

Figure 5:
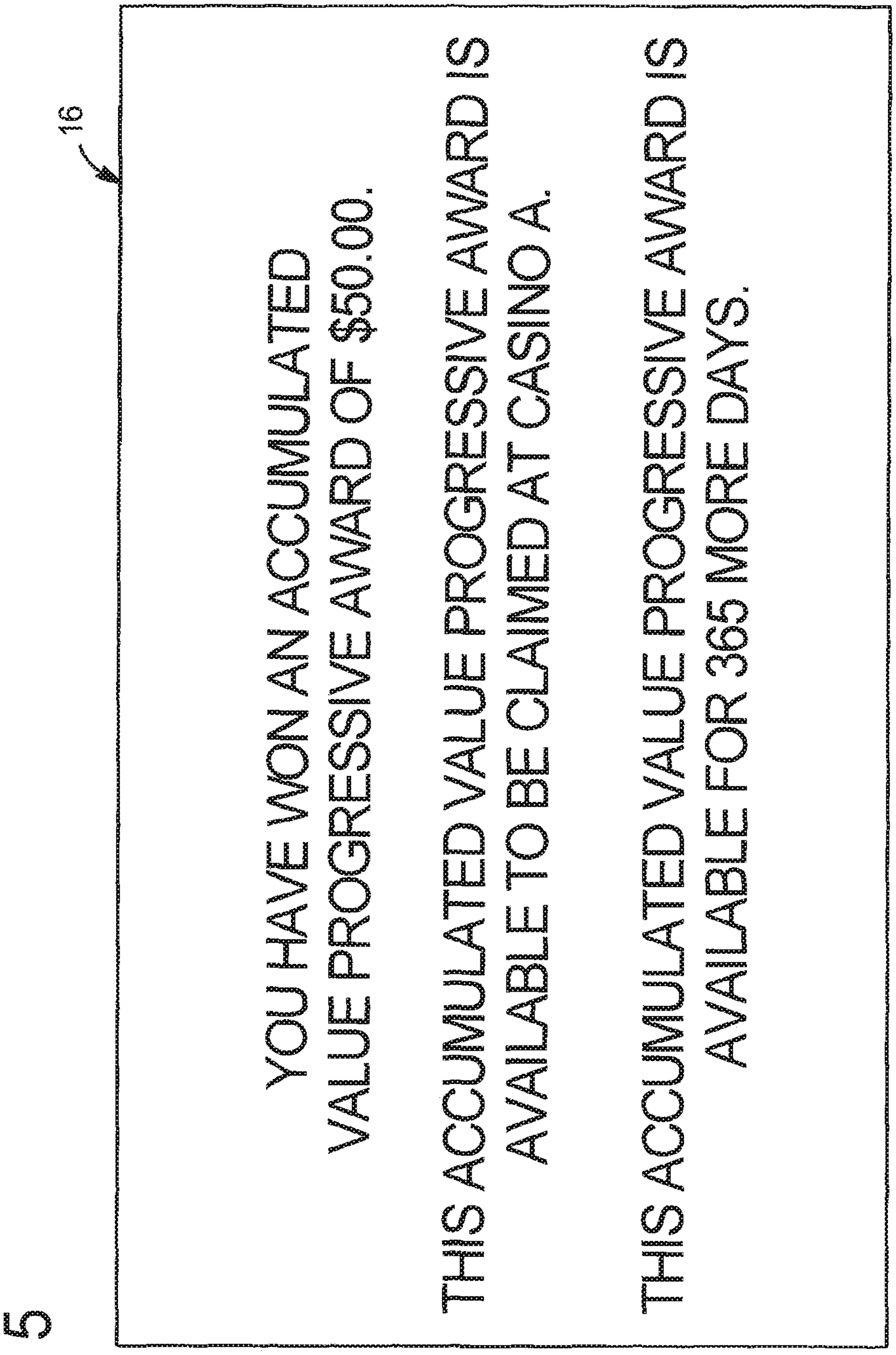
FIG. 5 is a top plan view of a display device of one embodiment of the gaming device disclosed herein illustrating information relating to the gaming system storing one progressive award for a designated period of time.

As illustrated in FIG. 5, appropriate notification messages such as "YOU HAVE WON AN ACCUMULATED VALUE PROGRESSIVE AWARD OF $1000.00! THIS ACCUMULATED VALUE PROGRESSIVE AWARD IS AVAILABLE TO BE CLAIMED AT CASINO A. THIS ACCUMULATED VALUE PROGRESSIVE AWARD IS AVAILABLE FOR 365 MORE DAYS." may be provided to the player. Such notification messages may be audio, text and/or visual messages sent to the winning player.

After the winning player is notified, the central controller provides the progressive award to the winning player as indicated by block 238. In one embodiment, if the player is playing at one of the gaming machines in the gaming system, the central controller causes that gaming machine to provide the winning player with the progressive award. In another embodiment, if the player is not playing at one of the gaming machines in the gaming system, the central controller may provide the progressive award to the winning player in conjunction with a player tracking system, such as via a player tracking card or other suitable manner. Alternatively, the central controller provides the progressive award to the winning player in conjunction with the casino or gaming establishment, such as through a cashier or any other suitable department of the casino.

In one embodiment, if the designated progressive award is not claimed by the winning player, the central controller may pick another winning player to win that designated progressive award. In one embodiment, the central controller causes a second player threshold value to be determined. In one such embodiment, another winning player is selected upon the designated progressive award reaching the second player threshold value. Alternatively, an unclaimed progressive award could be added to one or more designated progressive awards. For example, a previously designated progressive award may remain unclaimed by one or more winning players for a designated amount of time. If the designated amount of time expires, the central controller either provides the unclaimed progressive award to a different player (e.g., the player who contributes the coin which caused the second player threshold to be met) or adds the unclaimed progressive award to a different designated progressive award to increase that different designated progressive award.

In another embodiment, at least one designated progressive award is associated with a plurality of player threshold values and/or award threshold values. The player threshold values and/or award threshold values may be based on coin-in, time or another suitable metric. In one such embodiment, a designated progressive award is associated with a plurality of player threshold values based on coin-in. If a player contributes a coin that causes the designated progressive award to reach one of the player threshold values, that player is qualified to participate in a group gaming environment. In one embodiment, a plurality of players at a plurality of the gaming machines in the gaming system work in conjunction with one another, such as playing together as a learn or group, to win the designated progressive award. For example, once a plurality of the players are separated into teams or groups, the central controller monitors subsequent wagers by each player of each team or group at the gaming machines in the gaming system. If one of the wagers causes the designated progressive award to reach an associated award threshold value, the team or group of the player who placed that wager wins the designated progressive award. In one such embodiment, any designated progressive award won by the group is shared, either equally or based on any suitable criteria, amongst the different players of the group. Alternatively, if a player contributes the coin that causes the designated progressive award to reach one of the player threshold values, that player competes against at least one other player (i.e., another player who contributed a coin that caused the designated progressive award to reach one of the player threshold values) for the designated progressive award.

Figure 6:
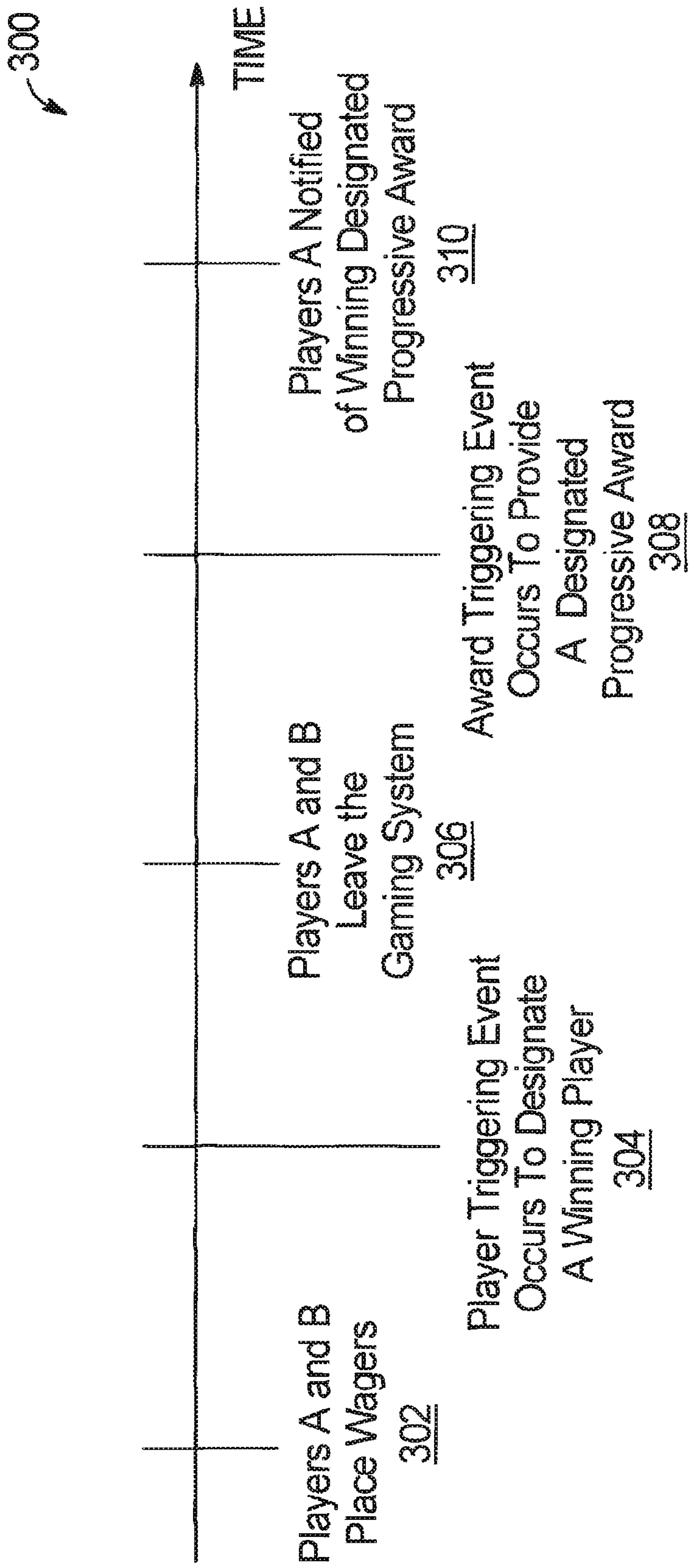
FIG. 6 is a timeline of one embodiment of different and independent triggering events for a progressive award available to be provided to a player in the gaming system.

FIG. 6 illustrates a timeline 300 showing one embodiment of different and independent triggering events for a progressive award available to be provided to a player in the gaming system. In this embodiment, a first triggering event 304, such as a player triggering event, occurs when the progressive award reaches a player threshold or player trigger value and a second triggering event 308, such as an award triggering event, occurs when the progressive award reaches an award threshold or award trigger value. The central controller monitors the wagers at the gaming machines in the gaming system during an accumulation period for the progressive award and determines whether the player triggering event and/or the award triggering event occurs.

The gaming system maintains at least one progressive award, which may be an accumulated value progressive award. The progressive award starts at an initial or default value, such as zero, and increments from the initial or default value or is funded based on wagers made by the players at the gaming machines in the gaming system. The accumulated value progressive award continues to increment during an accumulated value progressive award accumulation period, which may be set to any length determined by the gaming system operator. To be eligible to win the accumulated value progressive award, in this embodiment, one of the players at one of the gaming machines places a wager during the accumulation period. As illustrated, Players A and B place wagers at respective gaming machines 302. A determined amount, such as an amount ranging from 0.001% to 10%, of the wager is contributed to the accumulated value progressive award. For example, if the contribution rate is 1% for each $1.00 wagered, one penny or $0.01 will be contributed to the progressive award for each $1.00 wagered. In this example, the player threshold value is the 5,000$^{th}$ coin or when the accumulated value progressive award reaches $50.00 (i.e., based on a contribution rate of 1% if each coin is one dollar and the accumulated value progressive award starts at a default value equal to $0) and the award threshold value is the 12,500$^{th}$ coin or when the accumulated value progressive award reaches $125.00 (i.e., based on a contribution rate of 1% if each coin is one dollar and the accumulated value progressive award starts at a default value equal to $0).

In one embodiment, if either Player A or Player B leaves the gaming system (e.g., stops playing at one of the gaming devices, changes gaming devices or cannot be located at another gaming machine in the gaming system) prior to the accumulated value progressive award reaching the player threshold value, that player remains eligible for the accumulated value progressive award since Players A and B contributed to the accrual of the accumulated value progressive award. As illustrated, the player triggering event 304 occurs when the accumulated value progressive award increments to or reaches the player threshold value, such as 5,000 coins or $50.00. For example, on a $1 wager with 1% allocated to the accumulated value progressive award which hits at $50.00, the 5,000$^{th}$ coin wagered (i.e., based on a contribution rate of 1% if each coin is one dollar and the accumulated value progressive award starts at a default value equal to $0) results in the accumulated value progressive award reaching the player threshold (and thus designating a winning player).

In one embodiment, Player A and Player B are sent notification of which player the central controller designated as the winning player. Alternatively, no such notification is sent to the players. For example, the central controller determined to designate Player A as the winning player. As illustrated, Players A and B left the gaming system after this designation. Accordingly, Players A and B may or may not be aware that a winning player has been designated.

After the player triggering event 304 occurs, the accumulated value progressive award continues to increment or increase based on coin-in. In one embodiment, only players currently playing at one of the gaming devices when the player triggering event 304 occurs are eligible for the accumulated value progressive award. That is, the eligibility is closed to players who were not playing at one of the gaming devices when the player triggering event 304 occurs. As illustrated, Players A and B leave the gaming system 306 (or cannot be located at a gaming machine in the gaming system) after the player triggering event 304 occurs and prior to the award triggering event 308. Although the winning player has been designated, it should be appreciated that Player B is eligible for the accumulated value progressive award since Player B contributed to the accrual of the accumulated value progressive award.

When a player of one of the gaming machines of the gaming system contributes the coin that causes the accumulated value progressive award to increment to $125.00 or the 12,500$^{th}$ coin, the award triggering event 308 occurs. Upon the occurrence of the award triggering event 308, the central controller determines the amount of the accumulated value progressive award (e.g., $125.00) and provides the accumulated value progressive award to the winning player. Since the progressive award accumulated to 12,500 coins, the central controller provides the winning player with the progressive award of $125.00.

Player A either left the gaming system or cannot be located at another gaming machine in the gaming system 306. The accumulated value progressive award, such as a progressive award amount of $125.00, is provided to Player A (i.e., the designated winning player). After the award triggering event, the designated winning player is sent notification of winning the designated progressive award 310. Accordingly, Player A is sent notification of winning the designated progressive award in any suitable format, such as through e-mail or via an internet website. In one embodiment, Player A is required to return to the gaming establishment or casino where the accumulated value progressive award was won to claim the won accumulated value progressive award.

In this embodiment, the occurrence of the player triggering event 304 is prior to the occurrence of the award triggering event 308 and the progressive award is provided to the designated winning player. It should be appreciated that selecting a winning player for a progressive award that is still being contributed to or accumulated reduces jackpot fatigue because the value of the progressive award when the winning player is designated (e.g., after the 5,000$^{th}$ coin is wagered) has no bearing on a final value of that progressive award when that same progressive award is provided to the winning player (e.g., after the 12,500$^{th}$ coin is wagered).

Figure 7:
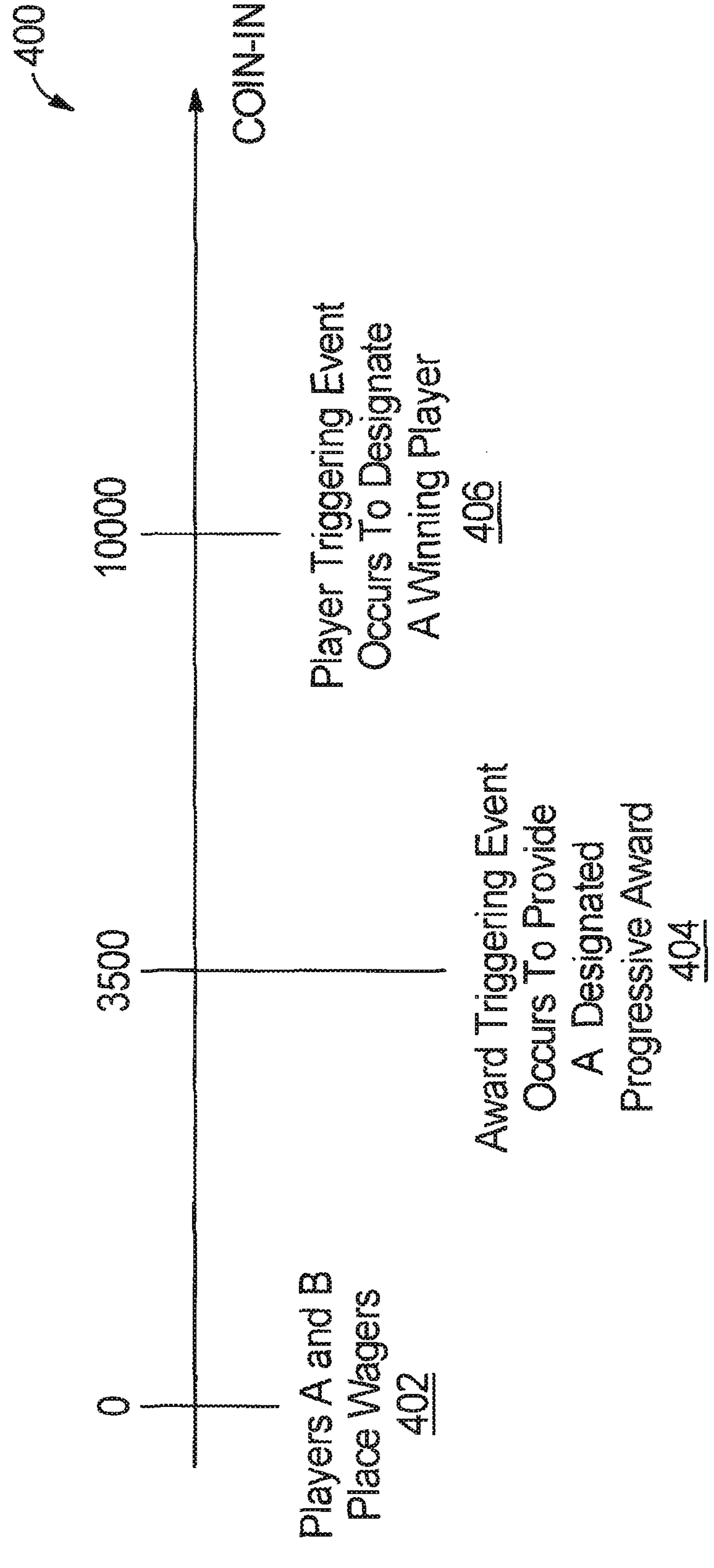
FIG. 7 is a chart of one embodiment of different and independent triggering events for a progressive award available to be provided to a player in the gaming system.

FIG. 7 illustrates a chart 400 showing different and independent triggering events for a progressive award available to be provided to a winning player. As illustrated in FIG. 7, chart 400 shows that Players A and B place wagers at gaming machines in the gaming system 402. Chart 400 also shows that an award triggering event 404 can occur before a player triggering event 406. The player threshold value of 10,000 coins is greater than the award threshold value of 3,500 coins. Accordingly, the occurrence of the award triggering event 404 is prior to the occurrence of the player triggering event 406 and the central controller designates the winning player after determining to provide the accumulated value progressive award.

In one embodiment, the central controller stores or escrows the accumulated value progressive award until a winning player is determined. The accumulated value progressive award may be stored for a predetermined length of time or until the winning player claims the award. Alternatively, the accumulated value progressive award is stored for a predetermined length of time before being provided to the winning player. In one embodiment, any progressive award not claimed in a predetermined amount of time are provided back to the gaming system to be awarded as a new progressive award to a new winning player.

In one alternative embodiment, the central controller randomly determines a plurality of different player and/or award triggering events for each accumulated value progressive award. For example, a first player threshold value is determined to be 5,000 coins and a second player threshold value is determined to be 10,000 coins. In this example, an award threshold value is determined to be 15,000 coins. The award threshold value of 15,000 coins is greater than the first and second player threshold values of 5,000 and 10,000, respectively. Accordingly, the award triggering event occurs after the occurrence of both player triggering events. In this embodiment, if the player who wagered the 5,000$^{th}$ coin is unable or does not claim the accumulated value progressive award, the central controller offers the accumulated value progressive award to the player who wagered the 10,000$^{th}$ coin. In one embodiment, if the player who wagered the 5,000$^{th}$ coin claims or is provided with the accumulated value progressive award, the central controller provides a secondary award to the player who wagered the 10,000$^{th}$ coin. In various embodiments, the players who wagered the 5,000$^{th}$ and 10,000$^{th}$ coins are provided a group gaming event, wherein the players either cooperate to play for a designated progressive award or compete for a designated progressive award.

Figure 8:
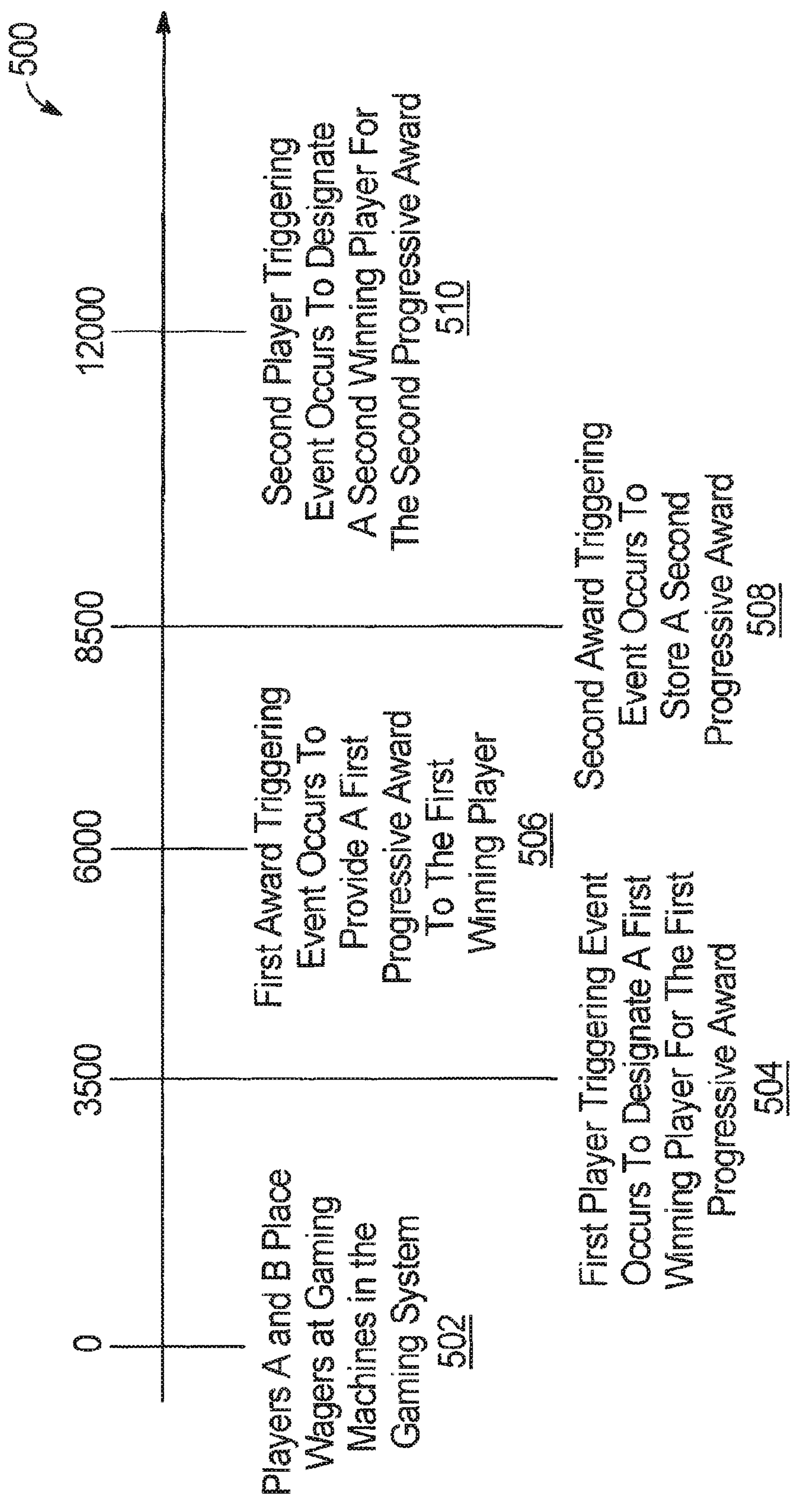
FIG. 8 is a chart of one embodiment of different and independent triggering events for a progressive award available to be provided to a player in the gaming system.

FIG. 8 illustrates a chart 500 showing different and independent triggering events for a plurality of progressive awards available to be provided to a player in the gaming system. In this embodiment, each progressive award is associated with a player triggering event and an award triggering event. Players A and B place wagers at gaming machines in the gaming system 502. For a first progressive award, a first player triggering event 504 occurs when a first progressive award increments to or reaches a first player threshold or player trigger value of 3,500 coins. A first award triggering event 506 associated with the first progressive award occurs when the first progressive award increments to or reaches a first award threshold or award trigger value of 6,000 coins. As described above, the winning player is designated prior to the determination to provide the first progressive award. Accordingly, when the first progressive award increments to $60.00 (i.e., based on a contribution rate of 1% if each coin is one dollar and the first progressive award starts at a default value equal to $0), the first progressive award is provided to the winning player who wagered or contributed the 3,500$^{th}$ coin associated with the first progressive award. For a second progressive award, a second player triggering event 510 occurs when the second progressive award increments to or reaches a second player threshold or player trigger value of 12,000 coins. A second award triggering event 508 associated with the second progressive award occurs when the second progressive award increments to or reaches a second award threshold or award trigger value of 8,500 coins. As described above, the progressive award is determined to be provided prior to the winning player being designated. Accordingly, when the second progressive award increments to $120.00 (i.e., based on a contribution rate of 1% if each coin is one dollar and the second progressive award starts at a default value equal to $0), the second progressive award having a value of $85.00 (i.e., based on a contribution rate of 1% if each coin is one dollar and the second progressive award starts at a default value equal to $0) is provided to the designated winning player. The central controller monitors the wagers at the gaming machines in the gaming system during an accumulation period for each progressive award and determines whether the player triggering event and/or award triggering event occurs for each progressive award.

In one embodiment, the player triggering event and the award triggering event are each associated with a separate range of values. The range of values defines the minimum value and the maximum value of the accumulated value progressive award associated with the player triggering event and the award triggering event. In this embodiment, when an accumulated value progressive award increments or increases to a first accumulated value progressive award hit value, such as a player threshold value, within the range of values associated with the player triggering event, the gaming system designates the player whose coin-in matched the accumulated value progressive award hit value or the player threshold value as the selected winning player. For example, the player triggering event is associated with a range of $10 to $100 for the accumulated value progressive award. In this example, the player triggering event will occur and a winning player is designated when the value of the accumulated value progressive award increments to a player threshold value between $10 and $100.

When an accumulated value progressive award increments or increases to a second accumulated value progressive award hit value, such as an award threshold value, within the range of values associated with the award triggering event, the gaming system determines to provide the accumulated value progressive award to the designated winning player or causes the accumulated value progressive award to be stored until the winning player is designated. For example, the award triggering event is associated with a range of $200 to $300 of the accumulated value progressive award. In this example, the award triggering event will occur when the value of the accumulated value progressive award increments to an award threshold value between $200 and $300.

Based on the above examples, the accumulated value progressive award starts at a default value, such as $0 or other higher designated start up value, and increments based on wagers made by players at the gaming machines in the gaming system. The player triggering event is associated with a range of $10 to $100 and the award triggering event is associated with a range of $200 to $300 for the accumulated value progressive award. The player threshold value may be any value in the range associated with the player triggering event (e.g., $10 and $100). Similarly, the award threshold value may be any value in the range associated with the award triggering event (e.g., $200 and $300). The accumulated value progressive award continues to increment. If the player threshold value is $75, a winning player is designated when the value of the accumulated value progressive award increments to $75. The central controller stores the winning player (e.g., in association with a player tracking system) until the accumulated value progressive award increments to the award threshold value. If the award threshold value is $225, the winning player is provided the accumulated value progressive award when the value of the accumulated value progressive award increments to $225. In one embodiment, after the winning player is provided the accumulated value progressive award, a new accumulated value progressive award is started.

It should be appreciated that the ranges of the player and award threshold values may overlap. In such cases, when an accumulated value progressive award increments or increases to an accumulated value progressive award hit value within the range of values associated with the player triggering event and the award triggering event, the gaming system designates a winning player and, at a subsequent time, provides the accumulated value progressive award to the designated winning player. The designated winning player may be notified of the win via audio, text or visual based messages.

In one embodiment, the player and award triggering events are associated with different value ranges. In another embodiment, the player and award triggering events are associated with the same value range. In different embodiments, the player threshold value and the award threshold value (and/or the respective value ranges) are predetermined, randomly determined, determined based on the wagers placed in the gaming system, determined based on the status of one or more players (such as determined through a player tracking system), determined based on time, or determined based on any other suitable method.

Figure 9:
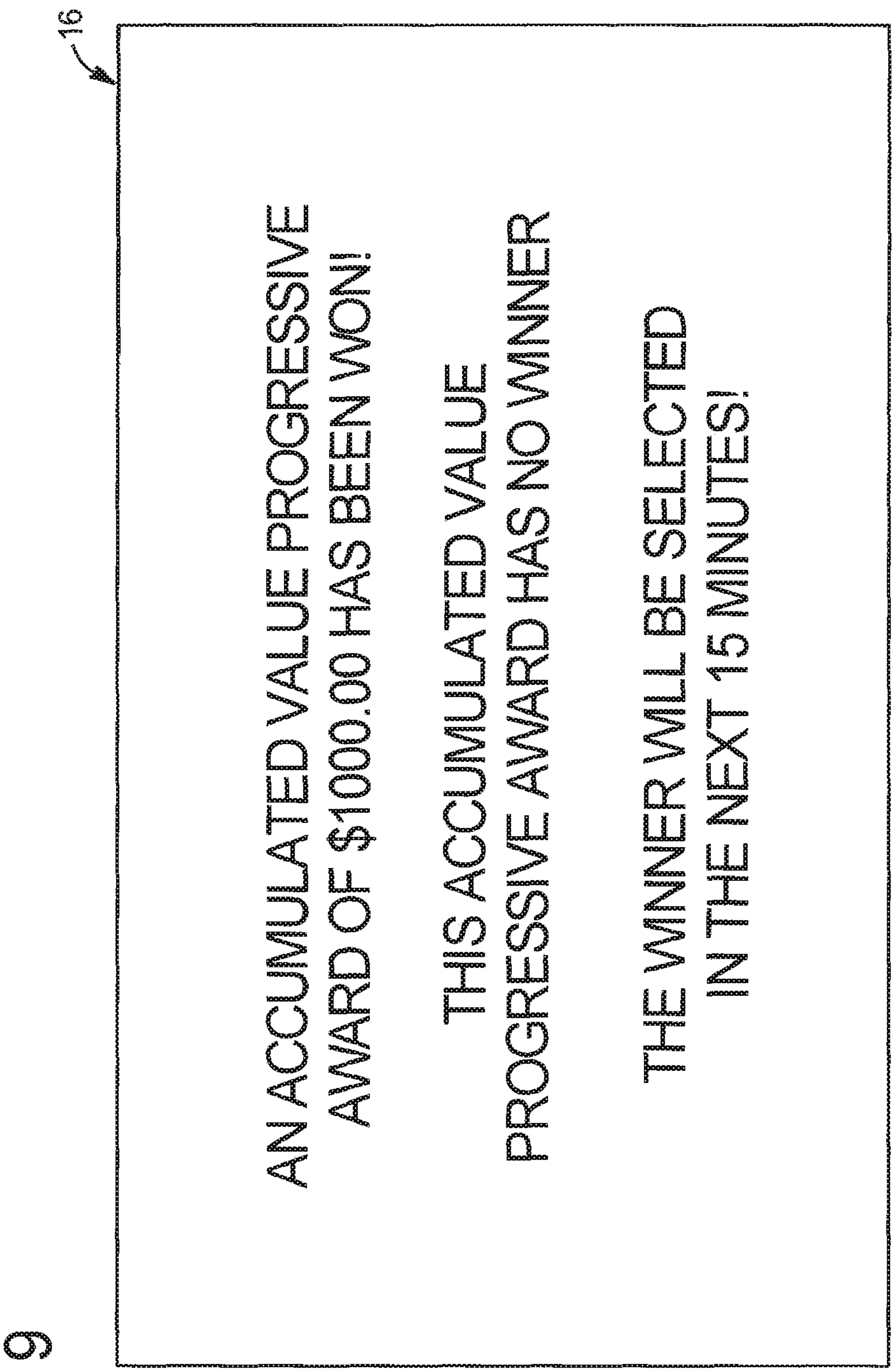
FIG. 9 is a top plan view of a display device of one embodiment of the gaming device disclosed herein illustrating information relating to the gaming system providing one progressive award within a designated period of time.

For example, if the award triggering event occurs after the $5{,}000^{th}$ coin, the player triggering event may occur at a predetermined time, such as 15 minutes, after the award triggering event occurs. In this example, the winning player is designated 15 minutes before the amount of the accumulated value progressive award is determined. After this determination, the accumulated value progressive award is provided to the designated winning player. The value of the accumulated value progressive award is reset to a default value and starts incrementing from the default progressive award level. It should be appreciated that although the accumulated value progressive award is reset to an appropriate progressive award level, other remaining progressive awards are not reset or otherwise affected by the triggering of the accumulated value progressive award. As illustrated in FIG. 9, appropriate messages such as "AN ACCUMULATED VALUE PROGRESSIVE AWARD OF $1000.00 HAS BEEN WON! THIS ACCUMULATED VALUE PROGRESSIVE AWARD HAS NO WINNER! THE WINNER WILL BE SELECTED IN THE NEXT 15 MINUTES!" may be provided to the player visually on the display device 16 of one of the gaming machines in the gaming system. Such messages may also be provided to the player through another display device, such as display device 18 or an overhead display shared by a plurality of gaming machines, or through suitable audio or audiovisual outputs.

By informing the player that a progressive award has hit or has been determined to be provided to a winning player, as well as other pertinent statistics, players will be more likely to feverishly play in hopes of winning the prize. If the player does not know what this maximum is, they may have no motivation to stay or play at a faster rate. Accordingly, in one embodiment, a metering and/or information display device may be used to display information regarding the different accumulated value progressive awards and/or the different player and award threshold values.

In additional embodiments wherein the controller knows when the progressive award is going to hit based on the selected parameters, such as coin-in, time or any other suitable predetermined metric, the gaming device/gaming system displays additional information to the player regarding the potential, upcoming accumulated value progressive award. By giving the player clues or hints as to when the progressive will hit, the player is encouraged to play the gaming device at a faster pace if the player knows that the selected winner is based on the coin-in.

In one embodiment, the gaming device displays information relating to one, more or each of the accumulated value progressive awards disclosed herein. Such displayed information provides the player with the ability to make decisions as to the rate they wish to play. With a plurality of displayed meters offering information to the current status of a plurality of accumulated value progressive awards, the player is provided an increased feeling of excitement about their chances of winning one or more of the progressive awards.

In one alternative embodiment, the central controller provides at least one game, such as a primary game, that is operable upon a wager placed by at least one player. The central controller maintains at least one progressive award, such as one or more accumulated value progressive awards. The central controller determines which player to provide with a designated one of the progressive awards (i.e., a player triggering event). This determination is based on a first time value, such as 9:01 am (i.e., at a player threshold value). For example, the central controller determines the winning player of the designated progressive award when time reaches 9:01 am. In this embodiment, the central controller also determines when to provide the progressive award to a winning player (i.e., an award triggering event). This determination is based on a second time value, such as 9:10 am (i.e., an award threshold value). For example, the central controller determines to provide the designated progressive award to a winning player when time reaches 9:10 am.

It should be appreciated that triggering events based on coin-in values, such as a Nth coin, and triggering events based on time, such as a Nth time, constitute different types of triggering events. In different embodiments disclosed herein, the same type of or different types of triggering events may be used to determine the winning player and when to provide the progressive award to the winning player. For example, the determination of a winning player is associated with a first type of triggering event (e.g., based on coin-in) and the determination of when to provide the progressive award to a winning player is associated with a second type of triggering event (e.g., based on time).

In one embodiment, a plurality of the gaming devices are connected together through a wide area network (WAN). The WAN may include an off-site central server or controller and an off-site gaming device located within gaming establishments in the same geographic area, such as a city or state. In this embodiment, the central controller determines a designated progressive award, a designated location where the designated progressive award will be won, which player at the designated location to provide with the designated progressive award. In this embodiment, the location is determined when the progressive award reaches a first value, such as a designated coin-in value (e.g., 7,200$^{th}$ coin) or a designated time value (e.g., 3:00 pm). The winning player is determined when the progressive award reaches a second value, such as a designated coin-in value (e.g., 7.600$^{th}$ coin) or a designated time value (e.g., 3:20 pm). The progressive award is provided or stored when the progressive award reaches a third value, such as a designated coin-in value (e.g., 8,000$^{th}$ coin) or a designated time value (e.g., 3:40 pm). For example, the central controller determines the designated location and subsequently determines the designated winning player and when to provide the designated progressive award. The central controller may determine the designated winning player and when to provide the designated progressive award in any order.

In one embodiment, the gaming system enables any player who contributed to an accrual of a designated progressive award during a designated time period to win that progressive award. For example, the designated progressive award is accrued or accumulated during a seven day period (i.e., the designated progressive award has a seven day accumulation period). In this example, the designated progressive award is determined to be provided to a designated winning player on the seventh day (i.e., the award triggering event occurs on the seventh day of the accumulation period). If a player arrives at a gaming establishment on the second day of the accumulation period. The player wagers on one or more games of one or more of the gaming machines of the gaming system in an attempt to win the designated progressive award. The player leaves the gaming establishment on the fifth day of the accumulation period. In this example, if the player triggering event occurs sometime between the second day and the fifth day, the player is eligible to win the designated progressive award. Since the amount of the designated progressive award is determined after the player leaves the gaming establishment, the gaming system causes a notification to be sent to the player. This notification informs the player of which designated progressive award won and the amount of that progressive award. As disclosed herein, the notification may be provided in any suitable format, such as via e-mail, via an electronic kiosk or via an internet website. It should be appreciated that the player triggering event and/or the award triggering event may occur at any time during the accumulation period and that one or more players may contribute to the accrual of the designated progressive award during any portion of the designated time period to be eligible to win that progressive award.

In one embodiment, the central controller selects the winning player from a group of players based, at least in part, on coin-in or time as described above, and based on at least one other factor, such as the status of a player. In such an embodiment, players who contribute to a designated progressive award may be grouped based on the amount of coin-in contributed to the progressive award and the winning player may be selected from the group based on status (as determined by a player tracking system). It should be appreciated that the gaming system selects the winning player based on a random determination, based on a weighted parameter, based upon a designated group, or based on any other suitable factor.

In one embodiment, different gaming devices in the gaming system have different progressive awards available to the player. In one such embodiment, different gaming devices are associated with different progressive awards based on a current configuration of the gaming system. In one embodiment, zero, one or more progressive awards may be associated with each of the gaming devices in the gaming system while zero, one or more different progressive awards may be associated with a plurality of, but not all of the gaming devices in the gaming system. For example, both a first set of gaming devices and a second, different set of gaming devices may be associated with a first accumulated progressive award, but the first set of gaming devices is also associated with a second accumulated value progressive award (which the second set of gaming devices is not).

In one embodiment, a gaming machine or bank of gaming machines may be simultaneously associated with a plurality of progressive awards. In these multi-level progressive ("MLP") configurations, a plurality of progressive awards start at different award or value levels, such as $10, $100, $1000 and $10,000 and each individually increment or increase until provided to a player. Upon a suitable triggering event at one of more of the gaming devices associated with the MLP, one or more of the progressive awards which form the MLP are provided to one or more of the players at such gaming devices. In one embodiment, each eligible player is eligible for one, a plurality of or each progressive award level of the MLP. Alternatively, separate eligibility conditions are associated with each progressive award level of the MLP.

In one embodiment, at least two of the progressive awards that form the MLP are associated with different types of triggering events (e.g., triggering events based on coin-in or triggering events based on time). In another embodiment, at least two of the progressive awards that form the MLP are associated with different triggering events (e.g., different coin-in values or time values). In one such embodiment, a first progressive award in the MLP is associated with a short term triggering event and a second progressive award in the MLP is associated with a long term triggering event. The short term triggering event occurs more frequently than the long term triggering event. Thus, one or more of the progressive awards in the MLP may be provided frequently (e.g., such as those with a low value) while one or more of the progressive awards in the MLP may be provided infrequently (e.g., such as those with a high value).

In one embodiment, different progressive awards are associated with different gaming machines or different numbers of gaming machines. For example, a progressive award valued at $10,000 may be associated with ten gaming devices while another progressive award valued at $500,000 may be associated with one-hundred gaming devices. In one embodiment, the multiple gaming machines may be in the same bank of machines, in the same casino or gaming establishment (such as through LAN), or in two or more different casinos or gaming establishments (such as through a WAN). For example, players from the multiple gaming machines may play for the same progressive award, wherein the determination of the winning player and when to provide the progressive award can occur in association with any of the gaming machines. In such an embodiment, the central controller considers the coin-in from the multiple gaming machines from the same or the different casinos or gaming establishments to determine whether the progressive award reaches the player threshold value and the award threshold value.

In another embodiment, each individual gaming machine maintains one or more progressive awards wherein a portion of the wagers placed at that respective gaming machine is allocated to one or more progressive awards maintained by such individual gaming machine. For example, a winning player is designated from an individual gaming machine to win a progressive award associated with that gaming machine. In such an embodiment, the central controller only considers the coin-in from the individual gaming machine to determine whether the progressive award reaches the player threshold value and the award threshold value. For example, the individual gaming machine processor and/or the central controller records the wagers for each player who played at a gaming machine during a designated period of time, such as during a bonus qualification period. The individual gaming machine processor and/or the central controller is operable to designate which of the players to provide with the progressive award when the progressive award reaches the player threshold value. The individual gaming machine processor and/or the central controller is operable to determine when to provide the progressive award to one of the players who played the primary game of the gaming device when the progressive award reaches the award threshold value. In one embodiment, the player threshold value is less than the award threshold value so that a winning player is designated prior to the progressive award being provided. In an alternative embodiment, each individual gaming machine maintains one or more progressive awards and the central server simultaneously or substantially simultaneously maintains one or more progressive awards. It should be appreciated that any suitable configuration of maintaining one, more or each of the progressive awards may be implemented in accordance with the gaming device and/or gaming system disclosed herein.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A gaming system comprising:
at least one gaming machine including:
a housing;
at least one display device supported by the housing;
a plurality of input devices supported by the housing, said plurality of input devices including
an acceptor, and
a cashout device;
at least one processor; and
at least one memory device which stores a plurality of instructions, which when executed by the at least one processor, cause the at least one processor to:
if a physical item is received via the acceptor, establish a credit balance based, at least in part, on a monetary value associated with the received physical item,
receive a placement of a wager on a play of a game,
for the play of the game:
determine a game outcome,
cause the at least one display device to display the determined game outcome,
determine any award associated with the determined game outcome, and
cause the at least one display device to display any determined award associated with the determined game outcome, and
if a cashout input is received via the cashout device, cause an initiation of any payout associated with the credit balance, and
a controller configured to communicate with the at least one gaming machine, the controller programmed to:
maintain an accumulated value progressive award, said accumulated value progressive award associated with a player selection hit value and a selected player winning hit value, said selected player winning hit value being greater than the player selection hit value,
increment the maintained accumulated value progressive award based on at least one wager placed on at least one of the plays of the game,
when the maintained accumulated value progressive award increments to the player selection hit value, select a player associated with the placement of the wager which caused the accumulated value progressive award to increment to the player selection hit value, and
when the accumulated value progressive award subsequently increments to the selected player winning hit value, regardless of whether the selected player is playing any games at any of the at least one gaming machine, designate the accumulated value progressive award to be provided to the selected player.

2. The gaming system of claim 1, wherein the selected player winning hit value is associated with a range of values which define a minimum value and a maximum value of the accumulated value progressive award.

3. A gaming system comprising:
at least one gaming machine including:
a housing;
at least one display device supported by the housing;
a plurality of input devices supported by the housing, said plurality of input devices including
an acceptor, and
a cashout device;
at least one processor; and at least one memory device which stores a plurality of instructions, which when executed by the at least one processor, cause the at least one processor to:
if a physical item is received via the acceptor, establish a credit balance based, at least in part, on a monetary value associated with the received physical item,
receive a placement of a wager on a play of a game,
for the play of the game:
determine a game outcome,
cause the at least one display device to display the determined game outcome,
determine any award associated with the determined game outcome, and
cause the at least one display device to display any determined award associated with the determined game outcome, and
if a cashout input is received via the cashout device, cause an initiation of any payout associated with the credit balance, and
a controller configured to communicate with the at least one gaming machine, the controller programmed to:
maintain an accumulated value progressive award, said accumulated value progressive award associated with a player selection hit value and a winning hit value, said player selection hit value being greater than the winning hit value,
increment the maintained accumulated value progressive award based on at least one wager placed on at least one of the plays of the game,
when the accumulated value progressive award increments to the winning hit value, designate a value of the accumulated value progressive award to be provided, and
when the maintained accumulated value progressive award subsequently increments to the player selection hit value:
select a player associated with the placement of the wager which caused the accumulated value progressive award to increment to the player selection hit value, and
cause the designated value of the accumulated value progressive award to be provided to the selected player.

4. The gaming system of claim 3, wherein the designated value of the accumulated value progressive award is different from a value displayed in association with the accumulated value progressive award when the maintained accumulated value progressive award increments to the player selection hit value.

5. The gaming system of claim 3, wherein the winning hit value is associated with a range of values which define a minimum value and a maximum value of the accumulated value progressive award.

6. A gaming system server comprising:
at least one processor; and
at least one memory device which stores a plurality of instructions, which when executed by the at least one processor, cause the at least one processor to:
maintain an accumulated value progressive award, said accumulated value progressive award associated with a player selection hit value and a selected player winning hit value, said selected player winning hit value being greater than the player selection hit value,
receive data associated with a placement of a wager on a play of a game, wherein a credit balance is decreasable based on the placed wager, said credit balance being increasable via an acceptor of a physical item associated with a monetary value, and said credit balance being decreasable via a cashout device,
for the play of the game:
determine a game outcome,
cause a display of the determined game outcome,
determine any award associated with the determined game outcome, and
cause a display of any determined award associated with the determined game outcome, wherein the credit balance is increasable based on any determined award associated with the determined game outcome,
increment the maintained accumulated value progressive award based on at least one wager placed on at least one of the plays of the game,
when the maintained accumulated value progressive award increments to the player selection hit value, select a player associated with the placement of the wager which caused the accumulated value progressive award to increment to the player selection hit value, and
when the accumulated value progressive award subsequently increments to the selected player winning hit value, regardless of whether the selected player is playing any games, designate the accumulated value progressive award to be provided to the selected player.

7. The gaming system server of claim 6, wherein the selected player winning hit value is associated with a range of values which define a minimum value and a maximum value of the accumulated value progressive award.

8. A gaming system server comprising:
at least one processor; and
at least one memory device which stores a plurality of instructions, which when executed by the at least one processor, cause the at least one processor to:
maintain an accumulated value progressive award, said accumulated value progressive award associated with a player selection hit value and a winning hit value, said player selection hit value being greater than the winning hit value,
receive data associated with a placement of a wager on a play of a game, wherein a credit balance is decreasable based on the placed wager, said credit balance being increasable via an acceptor of a physical item associated with a monetary value, and said credit balance being decreasable via a cashout device,
for the play of the game:
determine a game outcome,
cause a display of the determined game outcome,
determine any award associated with the determined game outcome, and
cause a display of any determined award associated with the determined game outcome, wherein the credit balance is increasable based on any determined award associated with the determined game outcome,
increment the maintained accumulated value progressive award based on at least one wager placed on at least one of the plays of the game,
when the accumulated value progressive award increments to the winning hit value, designate a value of the accumulated value progressive award to be provided, and when the maintained accumulated value progressive award subsequently increments to the player selection hit value:

select a player associated with the placement of the wager which caused the accumulated value progressive award to increment to the player selection hit value, and cause the designated value of the accumulated value progressive award to be provided to the selected player.

9. The gaming system server of claim 8, wherein the designated value of the accumulated value progressive award is different from a value displayed in association with the accumulated value progressive award when the maintained accumulated value progressive award increments to the player selection hit value.

10. The gaming system server of claim 8, wherein the winning hit value is associated with a range of values which define a minimum value and a maximum value of the accumulated value progressive award.

* * * * *